(12) United States Patent
Predick et al.

(10) Patent No.: US 10,245,015 B2
(45) Date of Patent: Apr. 2, 2019

(54) RETRACTOR WITH MODULAR TAP ASSEMBLIES

(71) Applicant: Life Spine, Inc., Huntley, IL (US)

(72) Inventors: Daniel Predick, Chicago, IL (US); Michael S. Butler, St. Charles, IL (US); Paul Christopher Zakelj, Chicago, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/448,010

(22) Filed: Mar. 2, 2017

(65) Prior Publication Data
US 2017/0238918 A1 Aug. 24, 2017

Related U.S. Application Data

(63) Continuation-in-part of application No. 15/207,026, filed on Jul. 11, 2016, which is a continuation-in-part of application No. 14/874,073, filed on Oct. 2, 2015, which is a continuation-in-part of application No. 13/720,800, filed on Dec. 19, 2012, now Pat. No. 9,386,916.

(60) Provisional application No. 61/577,857, filed on Dec. 20, 2011.

(51) Int. Cl.
*A61B 17/02* (2006.01)
*A61B 17/88* (2006.01)
*A61B 17/00* (2006.01)

(52) U.S. Cl.
CPC .......... *A61B 17/0206* (2013.01); *A61B 17/88* (2013.01); *A61B 2017/0046* (2013.01)

(58) Field of Classification Search
None
See application file for complete search history.

(56) References Cited

U.S. PATENT DOCUMENTS

| | | | |
|---|---|---|---|
| 530,728 A | 12/1894 | Sherbrook | |
| 3,509,873 A | 5/1970 | Karlin | |
| 4,065,941 A | 1/1978 | Aoki | |
| 7,335,207 B1 | 2/2008 | Smith | |
| 2004/0049101 A1* | 3/2004 | Phillips | A61B 17/0206 600/219 |
| 2005/0215866 A1 | 9/2005 | Kim | |
| 2007/0049930 A1 | 3/2007 | Hearn et al. | |
| 2007/0203399 A1 | 8/2007 | Gephart et al. | |

(Continued)

FOREIGN PATENT DOCUMENTS

| | | | | |
|---|---|---|---|---|
| WO | WO 2015134367 | * | 2/2015 | ............ A61B 17/02 |
| WO | WO 2015/160343 | | 10/2015 | |

*Primary Examiner* — Samuel Hanna
(74) *Attorney, Agent, or Firm* — Foley & Lardner LLP

(57) ABSTRACT

A retractor assembly includes a base, a first side assembly coupled to a first side of the base and configured to translate relative to the base along a first direction, a first tap assembly coupled to the first side assembly and configured to threadingly engage bone, a second side assembly coupled to a second side of the base and configured to translate relative to the base along the first direction independent from the first side assembly, a second tap assembly coupled to the second side assembly and configured to threadingly engage bone, and a center assembly coupled to a center portion of the base. At least a portion of the center assembly is configured to translate relative to the base along a second direction different from the first direction.

3 Claims, 45 Drawing Sheets

(56) References Cited

U.S. PATENT DOCUMENTS

| | | |
|---|---|---|
| 2007/0238932 A1 | 10/2007 | Jones et al. |
| 2010/0154604 A1 | 6/2010 | Su |
| 2010/0222644 A1 | 9/2010 | Sebastian et al. |
| 2011/0130793 A1* | 6/2011 | Woolley ............. A61B 17/0206 606/279 |
| 2011/0301423 A1 | 12/2011 | Koros et al. |
| 2014/0024900 A1 | 1/2014 | Capote et al. |
| 2015/0230787 A1* | 8/2015 | Friedrich ........... A61B 17/0206 600/213 |
| 2015/0250467 A1 | 9/2015 | Higgins |
| 2015/0305731 A1* | 10/2015 | Friedrich ............... A61B 90/30 600/216 |
| 2015/0313585 A1* | 11/2015 | Abidin ............... A61B 17/0206 600/213 |

\* cited by examiner

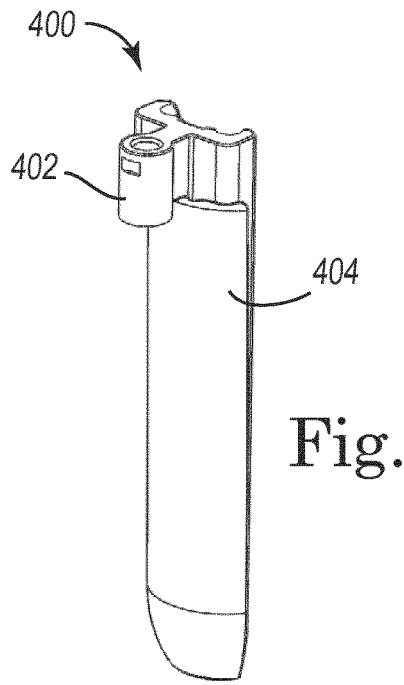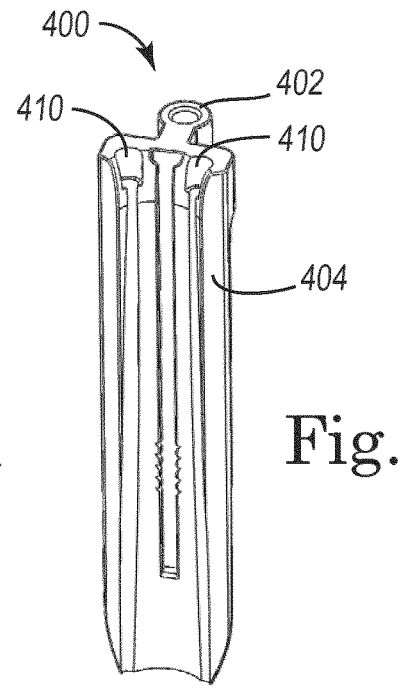
Fig. 20A  Fig. 20B
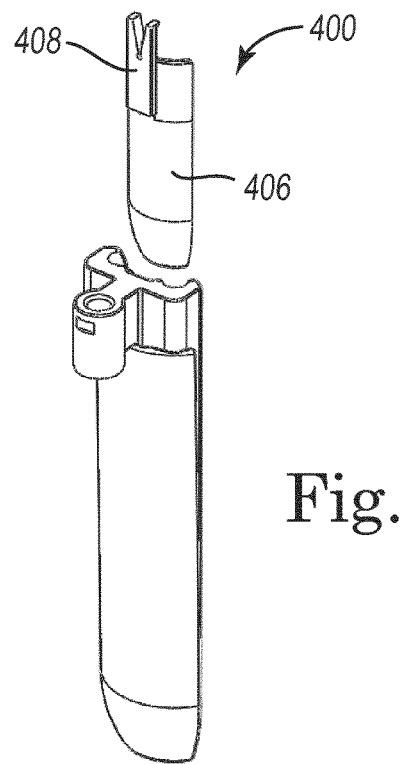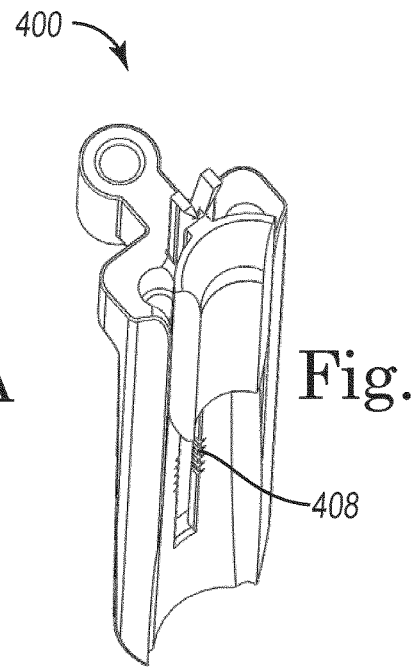
Fig. 21A  Fig. 21B

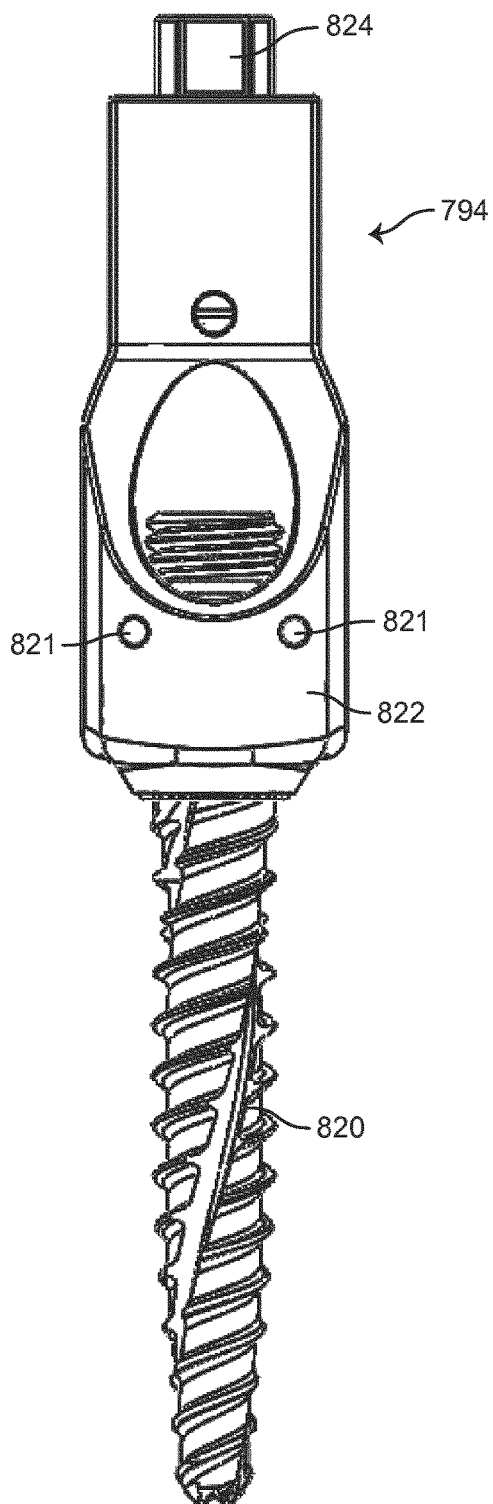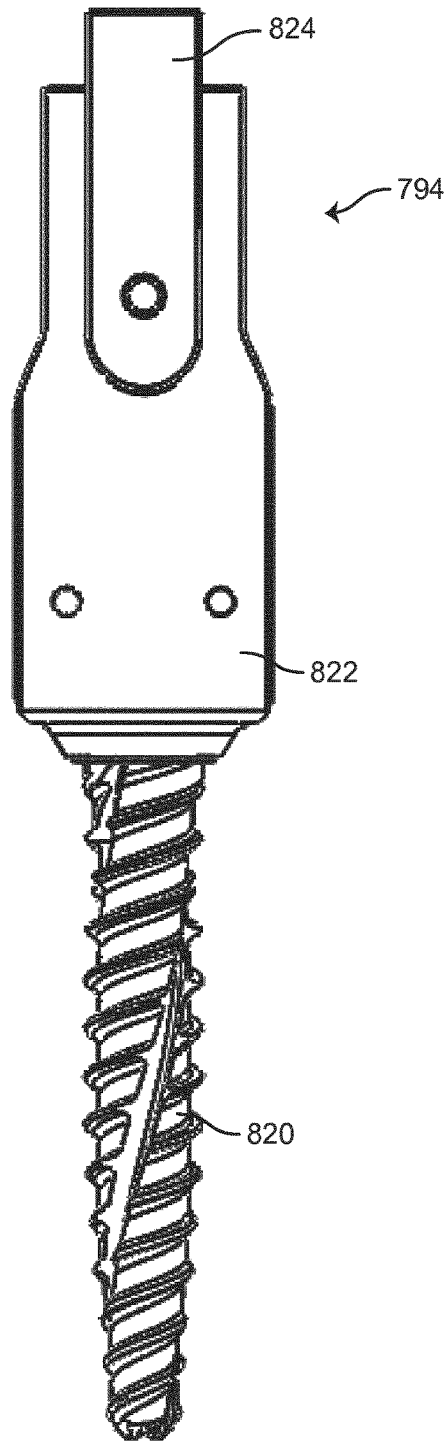
FIG. 42
FIG. 43

RETRACTOR WITH MODULAR TAP ASSEMBLIES

CROSS-REFERENCE TO RELATED PATENT APPLICATIONS

This application is a continuation-in-part of application Ser. No. 15/207,026, filed Jul. 11, 2016, which is a continuation in part of application Ser. No. 14/874,073, filed Oct. 2, 2015, which is a continuation-in-part of application Ser. No. 13/720,800, filed Dec. 19, 2012, now U.S. Pat. No. 9,386,916, which claims the benefit of Provisional Application No. 61/577,857 filed Dec. 20, 2011. The entire contents of all of these applications are incorporated herein by reference.

BACKGROUND

The present invention relates to surgical devices for retracting anatomy to provide exposure of an operating site, and more particularly, to retraction apparatus providing improved access to a surgical site for a spine procedure.

Surgical procedures typically require the use of a retractor to hold anatomies and/or tissues out of the way from the incision down to the actual surgical site. In the case of posterior spinal surgery for implanting various spine fixation components and/or other spinal orthopedic devices, it is necessary to retract different tissue types including large and strong paraspinal muscles in order to get to the actual surgical site. In order to accomplish this goal, spinal retractors have been developed that hold back the desired anatomy of a spinal surgical site and is fixed relative to the patient either directly or indirectly.

Many different types of spinal retractors are currently available many of which use retractor blades—a part of the distraction mechanism of the spinal retractor that enters the site of the incision and physically holds the anatomy apart. The retractor blades can be attached to a frame at an angle such as about 90 degrees from horizontal (i.e. generally vertical) or as to have a variable angle. However, current spinal retractors have various deficiencies. For instance, fixed angle retractor blade configurations limit flexibility of the spinal retractor, including loss of surgical site precision and overall stabilization. The variable angle retractor blade configurations lack preciseness and flexibility in retractor blade positioning.

It is therefore evident from the above that there is a need for an improved spinal retractor that can overcome the deficiencies of current spinal retractors. It is also evident from the above that there is a need for an improved spinal retractor which provides enhanced preciseness and flexibility in retractor blade positioning. It is furthermore evident that there is a need for an improved spinal retractor as aforementioned which also allows for instrument and/or component retention and positioning by the retractor blade assembly.

SUMMARY

The present disclosure relates to a spinal retractor for spinal surgeries providing improved preciseness and stability in positioning, tissue distraction, and surgical site access. The spinal retractor utilizes adjustable and lockable translating arms with angulating blades to provide a stable surgical site finestra and the adjustable retraction of surgical site tissue.

The present spinal retractor is a three blade retractor that allows triangulated medial/lateral and cephalad/caudal tissue retraction for spinal surgeries via the adjustably lockable translating arms. A medial/lateral translating arm with an angularly adjustable retraction blade co-acts and cooperates with angularly adjacent first and second cephalad/caudal translating arms with angularly adjustable retraction blades for tissue retraction and surgical site access.

The spinal retractor includes a plate having a medial/lateral adjustment system adjustably holding the medial/lateral translating arm, a first cephalad/caudal adjustment system adjustably holding the first cephalad/caudal translating arm, and a second cephalad/caudal adjustment system adjustably holding the second cephalad/caudal translating arm. The translating arms each have a blade holder which provides angular adjustment of the blade. Angular adjustment of each blade along with medial/lateral and cephalad/caudal adjustment provides improved preciseness and stability in positioning, tissue distraction, and surgical site access.

Another embodiment relates to a retractor assembly, including a base, a first side arm assembly coupled to a first side of the base, a second side arm assembly coupled to a second side of the base, and a central arm assembly coupled to a center portion of the base. The first side arm is configured to translate relative to the base along a first direction based on rotation of a first drive shaft positioned at a first angle relative to the first direction. The second arm is configured to translate relative to the base along the first direction independent from the first side arm assembly and based on rotation of a second drive shaft positioned at a second angle relative to the first direction. The central arm is configured to translate relative to the base along a second direction different from the first direction based on rotation of a third drive shaft positioned at a third angle relative to the second direction.

Another embodiment relates to a retractor assembly, including a base, a first side arm assembly coupled to a first side of the base, a second side arm assembly coupled to a second side of the base, and a center arm assembly coupled to a central portion of the base. The first side arm assembly is configured to translate relative to the base along a first direction. The second side arm assembly is configured to translate relative to the base along the first direction. The center arm assembly is configured to translate relative to the base along a second direction different from the first direction. Each of the first side arm assembly, the second side arm assembly, and the center arm assembly is coupled to the base by an adjustment mechanism including a multi-joint joint assembly.

Another embodiment relates to a method of operating a retractor. The method includes placing a retractor into a desired position, wherein the retractor includes a frame, a first side assembly, a second side assembly, and a center assembly. The method further includes translating the first side assembly relative to the frame along a first threaded shaft and independent from the second side assembly and the center assembly by rotating a first knob coupled to the first threaded shaft via a first joint assembly. The method further includes translating the second side assembly relative to the frame along a second threaded shaft and independent from the first side assembly and the center assembly by rotating a second knob coupled to the second threaded shaft via a second joint assembly. The method further includes translating the center assembly relative to the frame along a third threaded shaft and independent from the first side assembly and the second side assembly by rotating a third knob coupled to the third threaded shaft via a third joint assembly.

Another embodiment relates to a retractor assembly, comprising a base; a first side assembly coupled to a first side of the base and configured to translate relative to the base along a first direction; a first tap assembly coupled to the first side assembly and configured to threadingly engage bone; a second side assembly coupled to a second side of the base and configured to translate relative to the base along the first direction independent from the first side assembly; a second tap assembly coupled to the second side assembly and configured to threadingly engage bone; and a center assembly coupled to a center portion of the base, wherein at least a portion of the center assembly is configured to translate relative to the base along a second direction different from the first direction.

Another embodiment relates to a retractor assembly, comprising a base; a first side arm assembly coupled to a first side of the base and configured to translate relative to the base along a first direction; a second side arm assembly coupled to a second side of the base and configured to translate relative to the base along the first direction; a central arm assembly coupled to a center portion of the base and configured to translate relative to the base along a second direction different from the first direction; and a modular tap assembly coupled to at least one of the first side arm assembly and the second side arm assembly.

Another embodiment relates to a method of operating a retractor, comprising securing a first screw of a first blade assembly to a first portion of bone, the first blade assembly including a first blade; securing a second screw of a second blade assembly to a second portion of bone, the second blade assembly including a second blade; coupling the first blade assembly to a second arm portion of a first side assembly from a first direction while the first screw is secured to the first portion of bone; coupling the second blade assembly to a second arm portion of a second side assembly from the first direction while the second screw is secured to the second portion of bone; and coupling a center assembly to a frame.

Further aspects of the present disclosure will become apparent from consideration of the drawings and the following description of various embodiments. A person skilled in the art will realize that other embodiments are possible and that the details can be modified in a number of respects without departing from the inventive concepts disclosed herein. The following drawings and description are to be regarded as illustrative in nature and not restrictive.

BRIEF DESCRIPTION OF THE DRAWINGS

The features of the present disclosure will be better understood by reference to the accompanying drawings which illustrate various embodiments, wherein:

FIGS. 20A-21C illustrate a blade for a spinal retractor according to one embodiment.

FIGS. 40-43 are views of a modular tap assembly according to one embodiment.

Like reference numbers indicate the same or similar parts throughout the several figures.

Figure 1:
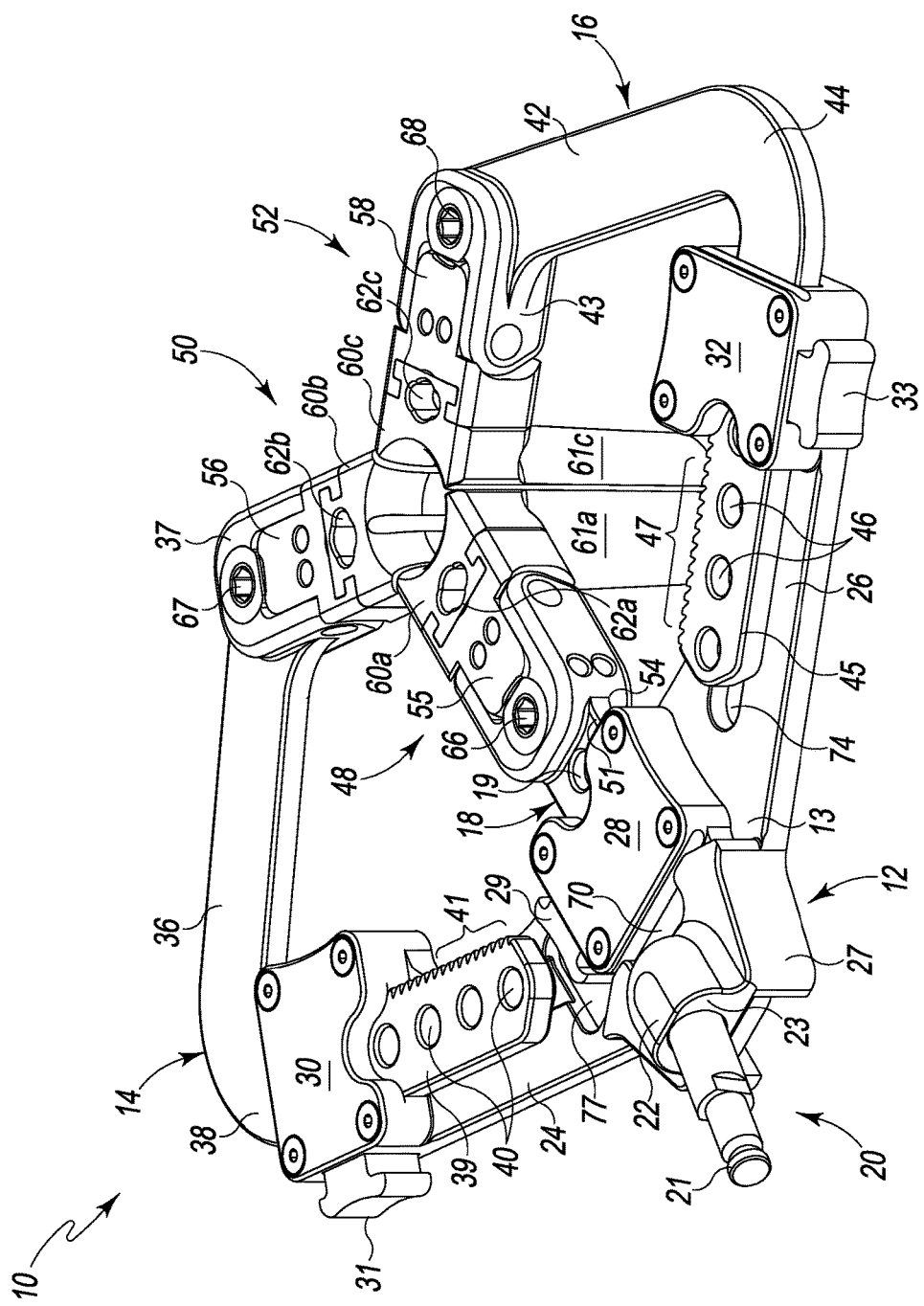
FIG. 1 is a topside view of a spinal retractor fashioned in accordance with the present principles, the spinal retractor shown in a closed position.

A description of the features, functions and/or configurations of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Reference is now made to FIGS. 1-5 which depict several views of a spinal retractor 10, fashioned in accordance with the present principles. The spinal retractor 10 is fashioned for use in anterior, posterior and lateral spinal surgeries or procedures, such as orthopedic implantation, vertebral fixation and vertebral stabilization, but may be used in other surgical procedures and orientations. The spinal retractor 10 is formed of an appropriate surgical material such as titanium, stainless steel, an alloy of same or the like.

The spinal retractor 10 has a body 12 characterized by a base, plate, platform or the like 13, a first translating arm 14 carried by the base 13 on one side thereof, a second translating arm 16 carried by the base 13 on another side thereof, wherein the sides are in the cephalad/caudal direction when the spinal retractor 10 is used, and a middle arm 18 carried by the base between the first and second translating arms 14, 16, wherein the middle arm is in the lateral/medial direction when the spinal retractor 10 is used. The base 13 further has a first side arm or wing 24 extending from a first side of the base 13 and a second side arm or wing 26 extending from a second side of the base 13. The first and second side arms 24, 26 extend generally in opposite directions relative to each other but with a slight inward angle as shown. The first and second side arms 24, 26 are in the cephalad/caudal direction when the spinal retractor 10 is used.

The spinal retractor 10 is designed to be fixed relative to a surgical site particularly, but not necessarily, to an external frame or the like (not shown) that is fixed relative to the patient. The spinal retractor 10 is also configured for rotation relative to the external frame. As such the base 13 has a boss 22 situated between opposite edges 25, 27, the boss 22 defining a face 23 from which projects a post, shaft, pole, bar, rod, stick or the like (i.e. a projection) 21. The spinal retractor 10 is connected with the external frame via the projection 21 which is received in or by a clamp, holder, receiver or the like (not shown) of the external frame. The projection 21 has a textured or keyed outer surface for engagement with the external frame, shown in the figures as radially spaced longitudinal grooves. The external surface of the projection 21 aids in positive engagement of the spinal retractor 10 with the external frame in order to fix rotational position of the spinal retractor 10 relative to the external frame.

A housing 28 is disposed on the base 13 between the first and second side arms 24, 26 and has an opening that receives the arm 18. The housing 28 cooperates with the arm 18 to provide adjustment of the arm 18 relative to the housing 28. Particularly, the arm 18 has a plurality of teeth, serrations or the like 51 on an inside edge thereof while the housing 28 includes ratchet components that cooperate with the teeth 51 of the arm 18 to provide ratcheting adjustability/translation of the arm 18 relative to the base 13. A button 29 is associated with the housing 28 and is coupled to the internal ratchet components thereof in order to allow release of the ratcheted (fixed) position of the arm 18 relative to the housing 28. In this manner, the arm 18 translates or slides in and out relative to the housing 28/base 13. Additionally, since a blade assembly 48, as described more fully below, is connected to the arm 18, the blade assembly 48 translates relative to the housing 28/base 13. This allows the blade assembly 48 to be positioned relative to the housing 28/base 13 and to the other blade assemblies 50, 52. Because of its position, the arm 18 and thus the blade assembly 48 translate or move in the medial/lateral directions when the spinal retractor 10 is in use. Position of the blade assembly 48 affects and effects retraction of tissue at the surgical site, particularly in the medial/lateral directions.

A housing 30 is disposed on an end of the first side arm 24 and has an opening that receives the first translating arm 14. The housing 30 cooperates with the first translating arm 14 to provide adjustment of the first translating arm 14 relative to the housing 30. Particularly, the first translating arm 14 has a plurality of teeth, serrations or the like 41 on an inside edge of an end 39 of the first translating arm 14 while the housing 30 includes ratchet components that cooperate with the teeth 41 of the first translating arm 14 to provide ratcheting adjustability/translation of the first translating arm 14 relative to the first side arm 24/base 13. A button 31 is associated with the housing 30 and is coupled to the internal ratchet components thereof in order to allow release of the ratcheted (fixed) position of the first translating arm 14 relative to the housing 30. In this manner, the first translating arm 14 translates or slides in and out relative to the housing 30/first side arm 24. Additionally, since the blade assembly 50, as described more fully below, is connected to the first translating arm 14, the blade assembly 50 translates relative to the housing 30/first side arm 24. This allows the blade assembly 50 to be positioned relative to the housing 30/first side arm 24 and to the other blade assemblies 48, 52.

Mention is now made to the configuration of the first translating arm 14. The first translating arm 14 is angled or bent so as to define a "boomerang" shape—i.e. an elbow or bend 38 between arm segments 36 and 39. Particularly, arm segments 36, 39 are bent to have an internal angle of less than ninety degrees (angle <90° with around seventy degrees (70°) being shown and preferred. Other angles, of course, may be used. A head 37 is provided at an end of the arm segment 36 opposite the bend 38 and is angled so as to project essentially parallel with the arm segment 39. The head 37 holds the blade assembly 50. As seen, the first translating arm 14 is angled so that its blade assembly 50 is proximate the blade assembly 48 of the arm 18.

The first translating arm 14 moves in and out relative to the housing 30 and thus the first side arm 24 through ratcheting of the arm segment 39 with its plurality of teeth 41 cooperating with the ratchet components of the housing 30. Movement of the arm 14 moves the corresponding blade assembly 50 relative to the other blade assemblies 48, 52. Because of its position and connection with the housing 30, the first translating arm 14 translates or moves in the cephalad/caudal directions so that the blade assembly 50 also moves in the cephalad/caudal directions. Position of the blade assembly 50 affects and effects retraction of tissue at the surgical site, particularly in the cephalad/caudal directions.

A housing 32 is disposed on an end of the second side arm 26 and has an opening that receives the second translating arm 16. The housing 32 cooperates with the second translating arm 16 to provide adjustment of the second translating arm 16 relative to the housing 32. Particularly, the second translating arm 16 has a plurality of teeth, serrations or the like 47 on an inside edge of an end 45 of the second translating arm 16 while the housing 32 includes ratchet components that cooperate with the teeth 47 of the second translating arm 16 to provide ratcheting adjustability/translation of the second translating arm 16 relative to the second side arm 26/base 13. A button 32 is associated with the housing 32 and is coupled to the internal ratchet components thereof in order to allow release of the ratcheted (fixed) position of the second translating arm 16 relative to the housing 32. In this manner, the second translating arm 16 translates or slides in and out relative to the housing 32/second side arm 26. Additionally, since the blade assembly 52, as described more fully below, is connected to the second translating arm 16, the blade assembly 52 translates relative to the housing 32/second side arm 26. This allows the blade assembly 52 to be positioned relative to the housing 32/second side arm 26 and to the other blade assemblies 48, 50.

Mention is now made to the configuration of the second translating arm 16. The second translating arm 16 is angled or bent so as to define a "boomerang" shape—i.e. an elbow or bend 44 between arm segments 42 and 45. Particularly, arm segments 42, 45 are bent to have an internal angle of less than ninety degrees (angle <90°) with around seventy degrees (70°) being shown and preferred. Other angles, of course, may be used. A head 43 is provided at an end of the arm segment 42 opposite the bend 44 and is angled so as to project essentially parallel with the arm segment 45. The head 43 holds the blade assembly 52. As seen, the second translating arm 16 is angled so that its blade assembly 52 is proximate the blade assembly 48 of the arm 18.

The second translating arm 16 moves in and out relative to the housing 32 and thus the second side arm 26 through ratcheting of the arm segment 45 with its plurality of teeth 47 cooperating with the ratchet components of the housing 32. Movement of the arm 16 moves the corresponding blade assembly 52 relative to the other blade assemblies 48, 50. Because of its position and connection with the housing 32, the second translating arm 16 translates or moves in the cephalad/caudal directions so that the blade assembly 52 also moves in the cephalad/caudal directions. Position of the blade assembly 52 affects and effects retraction of tissue at the surgical site, particularly in the cephalad/caudal directions.

Ratcheting adjustment of the arm 18 and of the first and second translating arms 14, 16 (and thus adjustment of the blade assemblies 48, 50, 52) may be accomplished manually but are preferably adjusted via one or more surgical instruments or tools. As such, the arms 18, 24, 26 and the base 13 are configured to allow manipulation of the arms 18, 24, 26 by a surgical instrument or tool (not shown).

Figure 4:
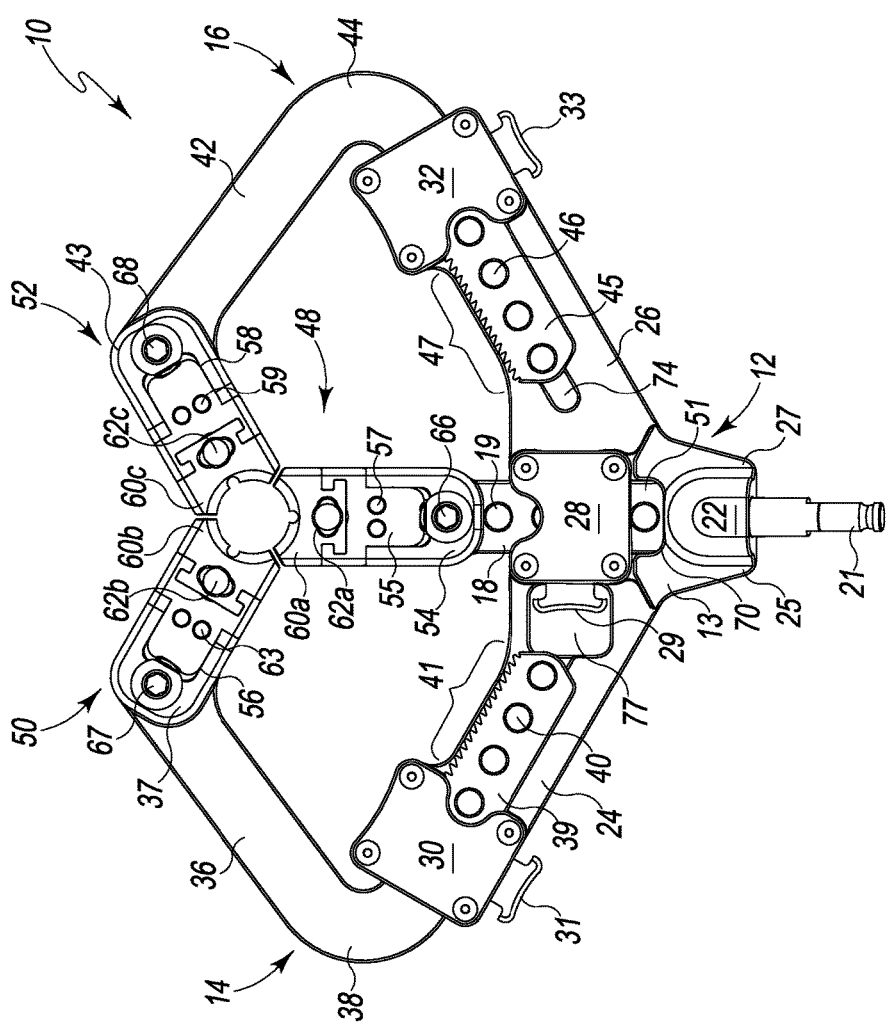
FIG. 4 is a top plan view of the spinal retractor of FIG. 1 in a closed position.

As best seen in FIGS. 1 and 4, the arm 18 has a series of holes 19 that extend along its longitudinal length. The base 13 has a slot 70 that extends through the housing 28 and which is sized to receive the arm 18. The arm 18 thus translates within the slot 70. One or more holes 19 of the arm 18 accepts a surgical instrument, tool and/or instrument/tool portion to manually move the arm 18 within the slot 70 and in conjunction/cooperation with the ratcheting housing 28. As should be appreciated, the ratcheting housing 28 allows incremental locking movement of the arm 18 in one direction while prohibiting movement in an opposite direction without the release thereof. In the case of arm 18, the arm 18 incrementally locks in a direction toward the base 13 in order to hold tissue by the blade assembly 48 in the medial/lateral direction. This allows the surgeon to incrementally manipulate the blade assembly 48 and thus the amount of tissue retraction by the blade assembly 48. Release is accomplished by the button/ratchet release system 29 associated with the housing/ratchet system 28. As best seen in FIG. 4, the button 29 extends from the housing 28 into a configured notch or recess 77 in the first side arm 24. Recessing the button 29 helps to prevent accidental activation and thus release of tissue retraction.

Figure 3:
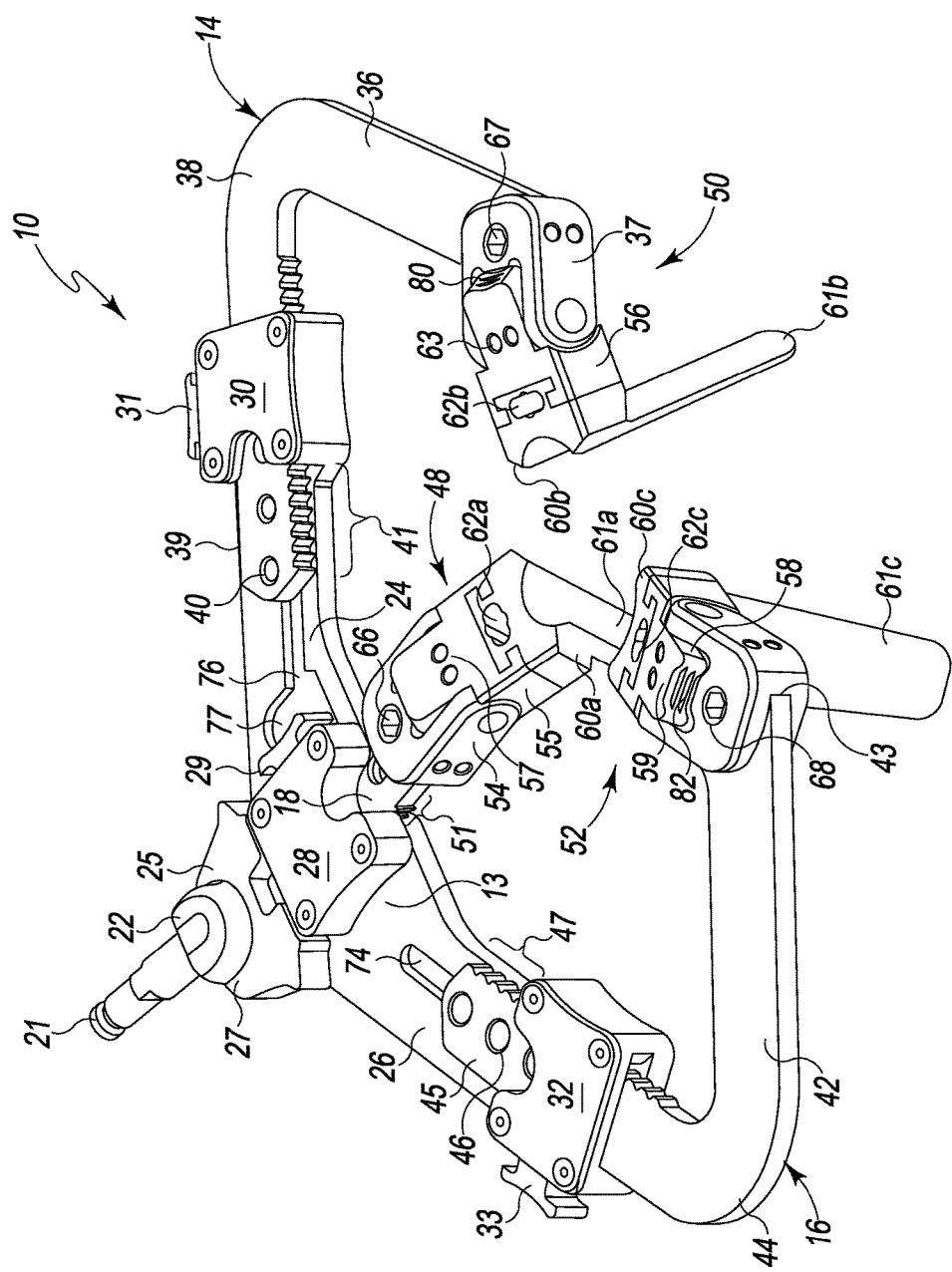
FIG. 3 is another topside view of the spinal retractor of FIG. 1 in an open position.

As best seen in FIGS. 1, 3 and 4, the first translating arm 14 has a series of holes 40 that extend along a length of the end segment 39. In conjunction therewith, the first side arm 24 of the base 13 has a slot 76 that extends from the configured recess 77 into the housing 30. The slot 76 is sized both in width and length to fit under the arm segment 39 and particularly under the holes 40. One or more holes 40 of the first translating arm 14 accepts a surgical instrument, tool and/or instrument/tool portion to manually move the arm 14 over the slot 76 and in conjunction/cooperation with the ratcheting housing 30. As should be appreciated, the ratcheting housing 30 allows incremental locking movement of the arm 14 in one direction while prohibiting movement in an opposite direction without the release thereof. In the case of the first translating arm 14, the arm 14 incrementally locks in a direction along the longitudinal length of the first side arm 24 inwardly toward the base 13 in order to hold tissue by the blade assembly 50 in the cephalad/caudal direction. This allows the surgeon to incrementally manipulate the blade assembly 50 and thus the amount of tissue retraction by the blade assembly 50. Release is accomplished by the button/ratchet release system 31 associated with the housing/ratchet system 30. The button 31 extends outward from the housing 30 helping to prevent accidental activation and thus release of tissue retraction.

As best seen in FIGS. 1, 3 and 4, the second translating arm 16 has a series of holes 46 that extend along a length of the end segment 45. In conjunction therewith, the second side arm 26 of the base 13 has a slot 74 that extends from proximate an end of the second side arm 26 near the base 13 and into the housing 32. The slot 74 is sized both in width and length to fit under the arm segment 45 and particularly under the holes 46. One or more holes 46 of the second translating arm 16 accepts a surgical instrument, tool and/or instrument/tool portion to manually move the arm 16 over the slot 74 and in conjunction/cooperation with the ratcheting housing 32. As should be appreciated, the ratcheting housing 32 allows incremental locking movement of the arm 16 in one direction while prohibiting movement in an opposite direction without the release thereof. In the case of the second translating arm 16, the arm 16 incrementally locks in a direction along the longitudinal length of the second side arm 26 inwardly toward the base 13 in order to hold tissue by the blade assembly 52 in the cephalad/caudal direction. This allows the surgeon to incrementally manipulate the blade assembly 52 and thus the amount of tissue retraction by the blade assembly 52. Release is accomplished by the button/ratchet release system 33 associated with the housing/ratchet system 32. The button 33 extends outward from the housing 32 helping to prevent accidental activation and thus release of tissue retraction.

Figure 2:
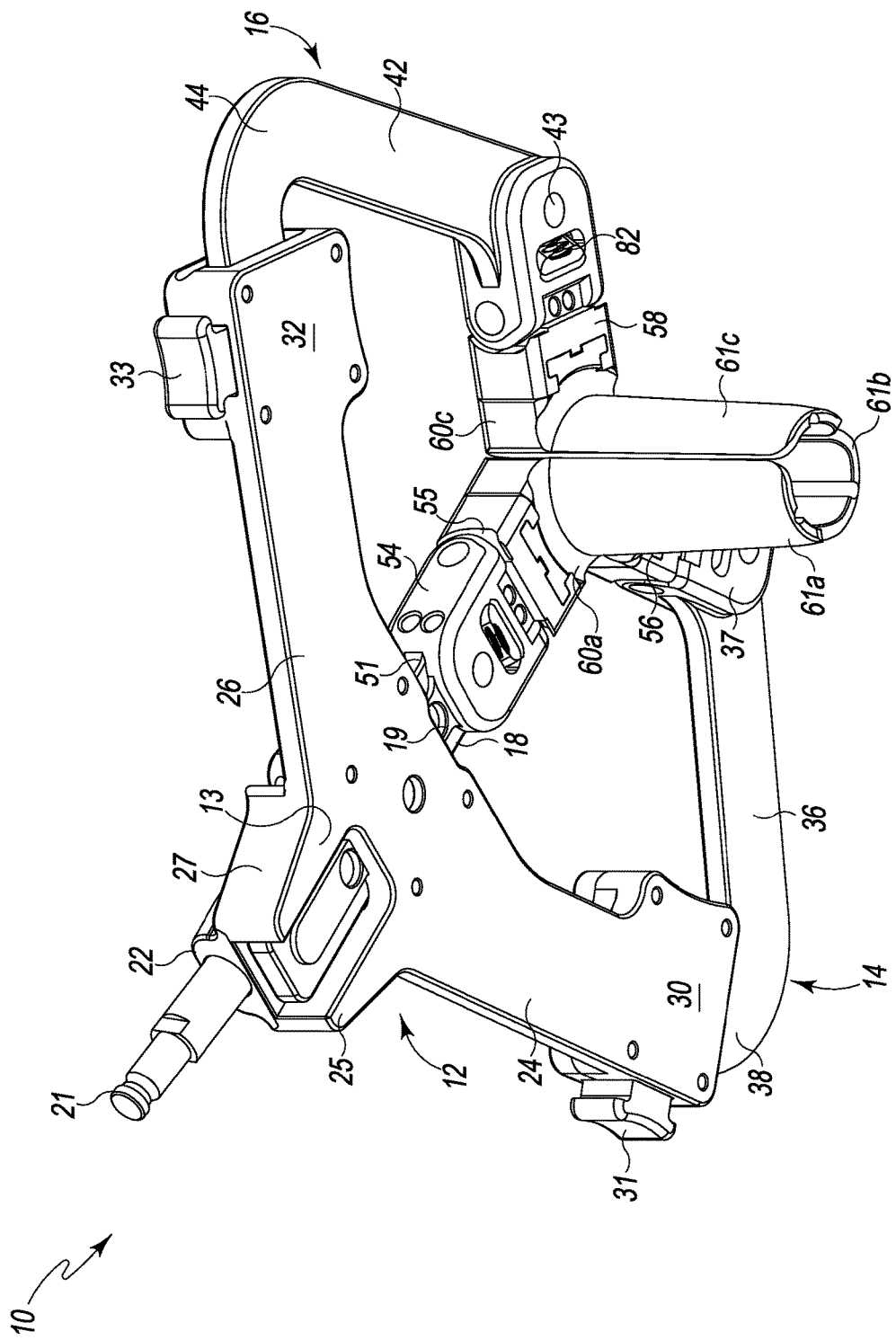
FIG. 2 is an underside view of the spinal retractor of FIG. 1 shown in a closed position.

As seen in the figures each arm 18, 14 and 16 has a respective blade assembly 48, 50, 52 for holding and retracting tissue during spinal surgery. The blade assembly 48 includes a head 54 which pivotally retains a blade holder 57 via an angulation system controlled by a set screw 66, the head 54 holding a blade 60a. The blade assembly 50 includes the head 37 which pivotally retains a blade holder 56 via an angulation system controlled by a set screw 67, the head 37 holding a blade 60b. The blade assembly 52 includes the head 43 which pivotally retains a blade holder 58 via an angulation system controlled by a set screw 68, the head 43 holding a blade 60c. The blades 60a, 60b and 60c are preferably, and as shown, identical. While each blade assembly 48, 50, 52 is identical, one or more blade assembly may be different as desired. However, in the preferred embodiment as shown, the three blade assemblies forming a triangular blade assemblage, are identical and fashioned in accordance with the present principles. Therefore, description of one blade assembly of the blade assemblies 48, 50, 52 describes the others of the blade assemblies 48, 50, 52. Moreover, the description of one blade 60a, 60b, 60c of the blade assemblies 48, 50, 52 describes the others of the blades 60a, 60b, 60c. In general, the blade assemblies 48, 50, 52 are each designed for up/down or posterior/anterior translation or angulation. In FIGS. 1, 2 and 4, the blade assemblies 48, 50, 52 are in a 0° or non-angulated position as well as in an un-retracted position. In FIG. 3, the blade assemblies 48, 50, 52 are in a downwardly angled position (an angle downwardly from 0°) as well as in a retracted position.

Figure 5:
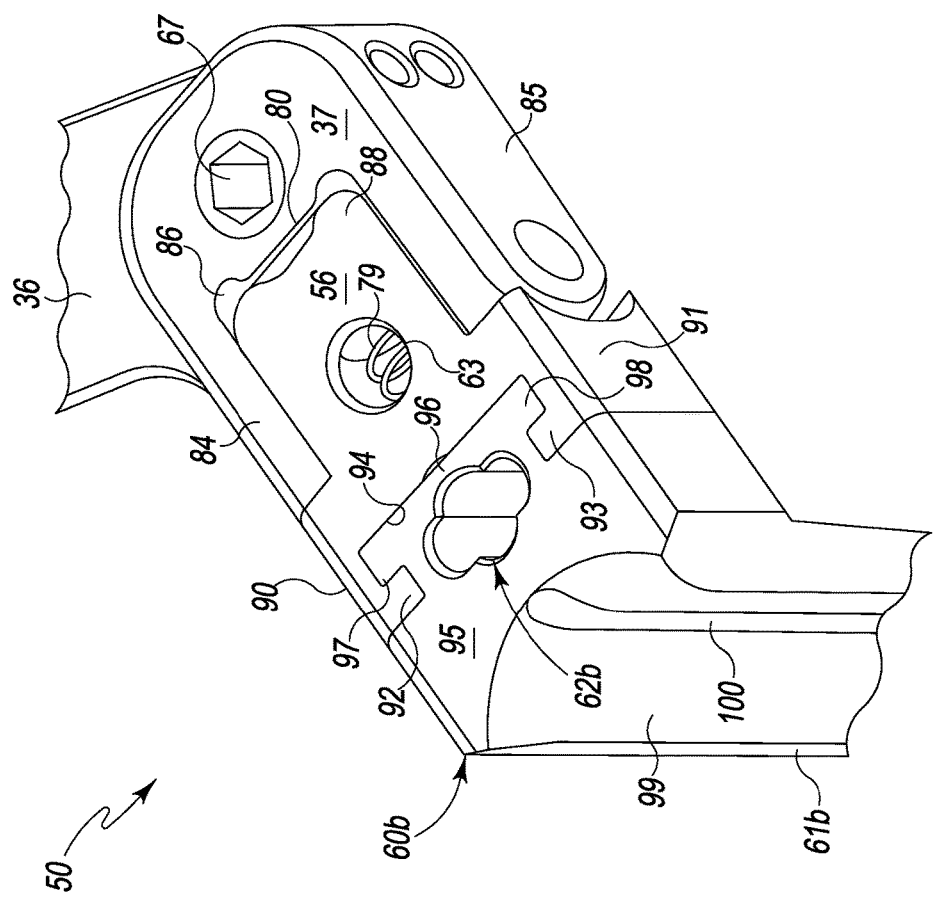
FIG. 5 is an enlarged topside view of a blade assembly on an arm of the spinal retractor of FIG. 1.

With particular reference to FIG. 5 the details of a blade assembly and blade will be described with reference to blade assembly 50. As seen, the blade holder 56 is shown in a 0° position wherein the blade 60b is in a full upright or vertical position. The blade holder 56 is pivotally coupled to the head 37. Particularly, an end or tongue 88 of the blade holder 56 is received within a cutout 86 of the head 37 and pivotally connected at sides thereof to arms 84 and 85 of the head 37. This allows the blade holder 56 to pivot relative to the head 37. The blade holder 56 and the head 37 are connected via the angulation adjustment system 63 which includes a worm gear system driven by the hex nut 67. Particularly (and in conjunction with FIG. 3) the hex nut 67 is externally threaded to mesh with screw serrations 80 on an end of the blade holder 56. As the hex nut 67 is rotated clockwise or counterclockwise the blade holder 56 will angulate or pivot up and down. As the blade holder 56 angulates or pivots downward, the spade portion 61b of the blade 60b moves outwardly (medially or laterally) to effect splaying of the tissue. As seen in FIG. 3, the blade holder 58 includes screw serrations 82 on an end thereof as part of its angulation adjustment system 59.

The blade holder 56 has first and second side arms 90, 91 that define a configured notch 94 that is adapted to receive a configured flange 96 of a head 95 of the blade 60b. The blade holder 56 and the blade 60b are configured to allow the blade 60b to be positively received and held, removed and replaced. Inwardly projecting ends 92, 93 of the first and second side arms 90, 91 define a confined slot for receipt and retention of the blade head 96, the blade flange 96 having lips 97, 98 for complementary reception by the ends 92, 93. The blade 60b is thus vertically inserted into and removed from the blade holder 56.

The blade holder 56 incorporates a spring loaded detent system 79 which releasably locks the blade 60b into the blade holder 56. The blade 60b has a keyed access point 62b to allow both insertion of the blade 60b into the blade holder 56 as well as actuation of the detent system 79 in order to release the blade 60b from the blade holder 56.

The blade 60b has a tong, spade, paddle or the like 61b that extends transverse from the head 95. An inner surface 99 of the paddle 61b is curved inwardly (i.e. concave relative to the head 95). A channel 100 extends from a top of the paddle 61b (i.e. the top of the concavity 99) to an end of the paddle 61b. The channel 100 receives a shaft that permits anatomical docking of the blade to bony anatomy and/or a cannula in which lighting may be inserted to aid in intra-operative visualization. Rounded corners permit the finestra formed by the blades 60a, 60b, 60c to maintain the same diameter as the blades are angulated.

It should be appreciated that the present spinal retractor 10 provides a table mount connection to secure retractor position relative to the patient via the frame (table). The cephalad/caudal translating arms incrementally lock positions via ratcheting teeth within each ratchet housing and subsequently expand both soft tissue retraction by means of the blades. Each translating arm can be moved independently. The cephalad/caudal translating arms cooperate and co-act with the medial/lateral translating arm to provide a stable finestra and retraction. Thumb actuated depressors release the locked positions of the arms and thus the blades. Adjustable convergence of each translating arm 14, 16, 18 with respective blades creates an adjustable finestra to the surgical site.

Referring now to FIGS. 6-21C, a spinal retractor assembly 210 is shown according to one embodiment. As discussed in greater detail below, retractor assembly 210 may share various functional and structural features with spinal retractor 10. In one embodiment, retractor assembly 210 includes a frame or base 212 (e.g., a plate, frame, or base assembly, etc.), a first side assembly 214, a second side assembly 216, and a center assembly 218. Assemblies 214, 216, and 218 are coupled to base 212 to enable translating movement of assemblies 214, 216, 218 relative to base 212 to provide retraction of tissue, etc. during surgical procedures involving the spine, etc. First and second side assemblies 214, 216 translate relative to frame 212 in a medial-lateral direction (e.g., along a first axis or direction), and center assembly 218 translates relative to frame 212 in a cephalad-caudal direction (e.g., along a second axis or direction) in a generally perpendicular fashion relative to first and second assemblies 214, 216. In one embodiment, each of assemblies 214, 216, 218 may be adjusted (e.g., translated) relative to frame 212 independently (e.g., such that each of assembly 214, assembly 216, and assembly 218 may be adjusted individually).

Figure 6:
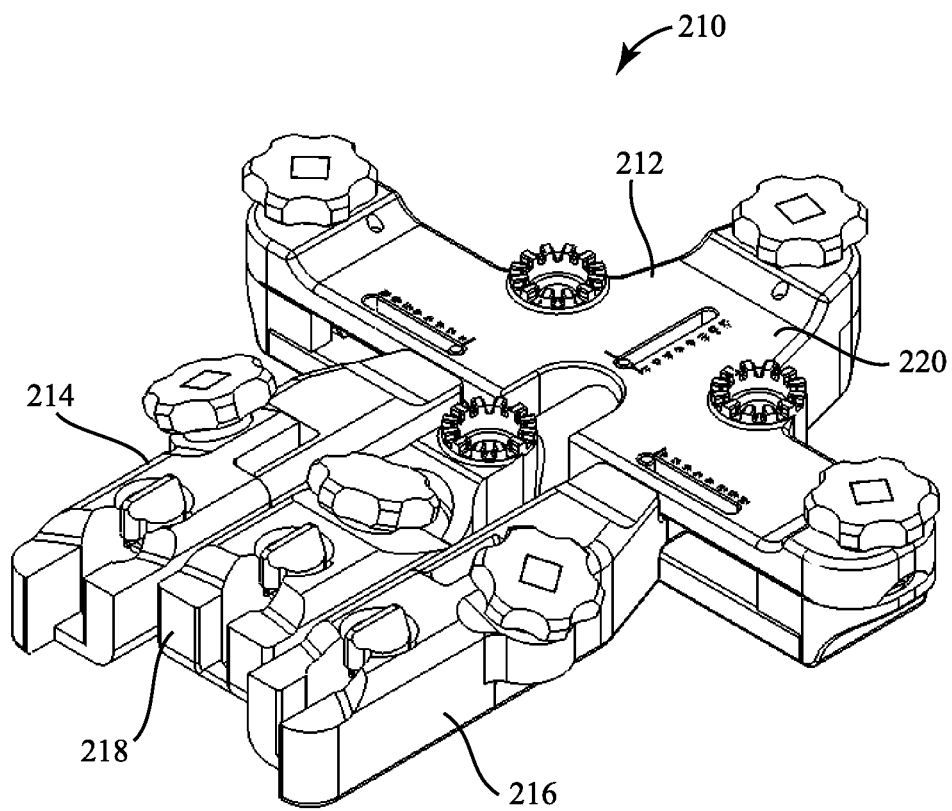
FIG. 6 is a perspective view of a spinal retractor according to an alternative embodiment.
Figure 10:
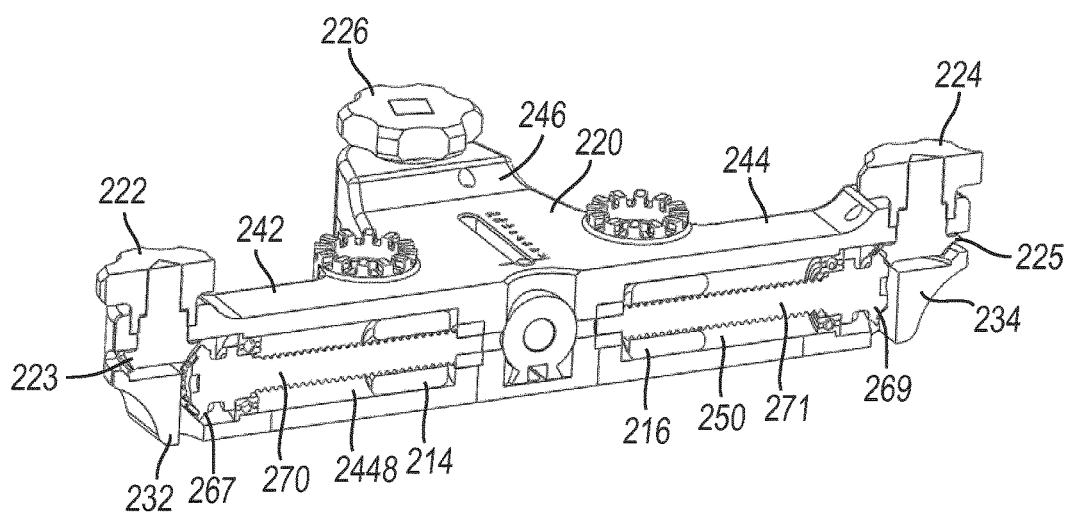
FIG. 10 is a cross-sectional perspective view taken along line 10-10 of FIG. 7 according to one embodiment.

Referring to FIGS. 6 and 10, frame 212 includes body 220, a first side adjustment member or knob 222, a second side adjustment member or knob 224, and a center adjustment member or knob 226. Knobs 222, 224 are coupled to drive members 223, 225, respectively, such that rotation of knobs 222, 224, causes a corresponding rotation of drive members 223, 225. Drive members 223, 225 include bevel gears in one embodiment and, as discussed in greater detail below, are configured to engage bevel gears on corresponding adjustment members. Knob 226 may be coupled to a drive member of similar structure and function.

Figure 7:
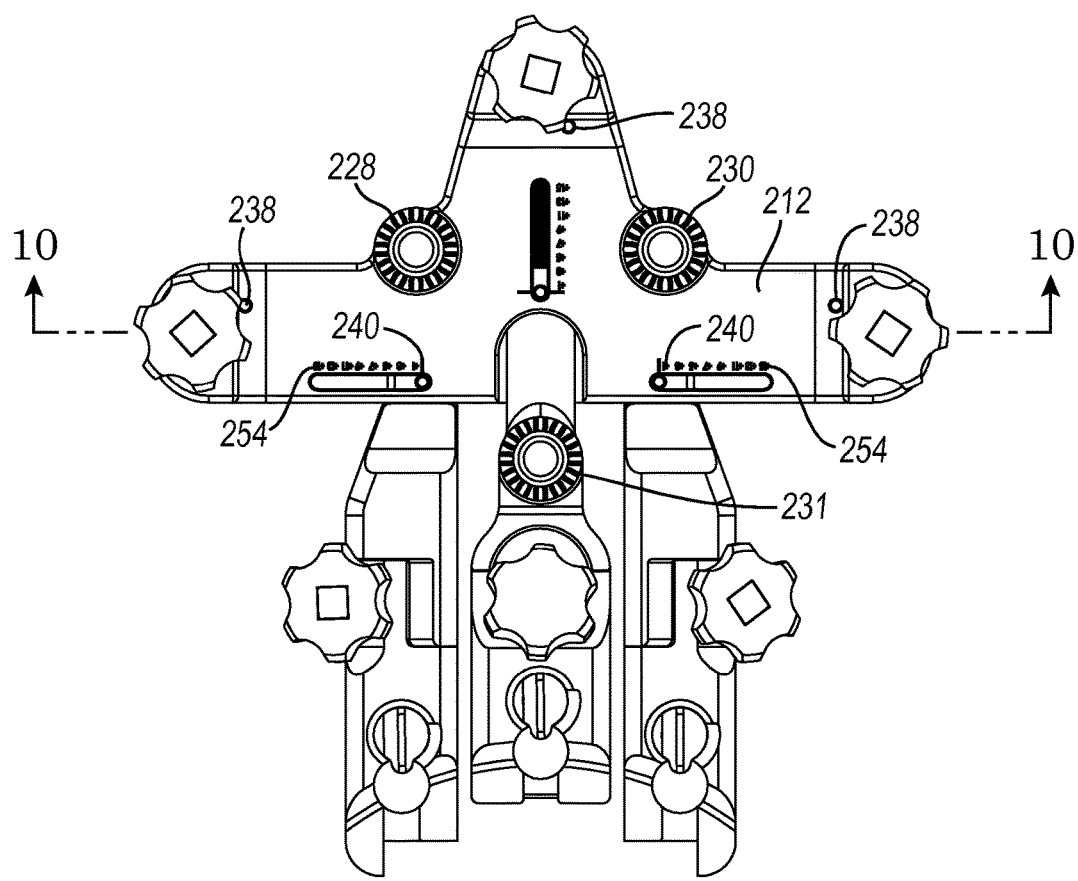
FIG. 7 is a top view of the spinal retractor assembly of FIG. 6 according to one embodiment.
Figure 8:
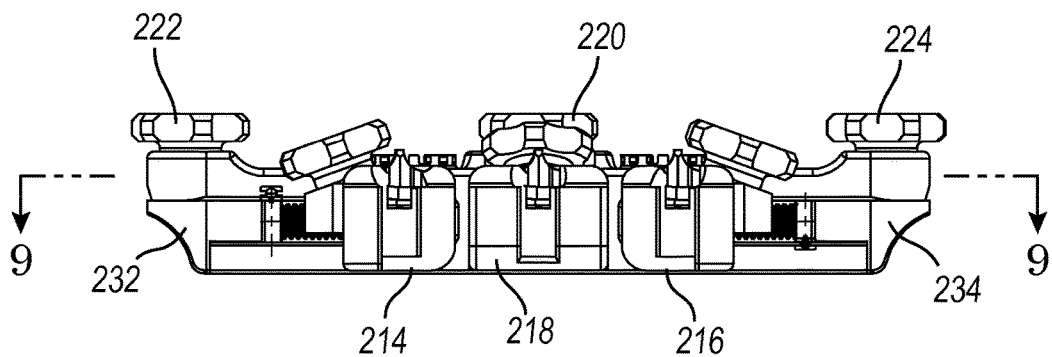
FIG. 8 is a front view of the spinal retractor assembly of FIG. 6 according to one embodiment.

In one embodiment, frame 212 further includes table arm mounts 228, 230, 231 (see FIG. 7). Mounts 228, 230, 231 are configured to enable attachment of retractor assembly 210 to a table arm in a fixed relationship. As such, retractor assembly 210 may be fixed in space via one or both of table mounts 228, 230, 231. Mounts 228, 230, 231 may be located in any suitable locations, and more or fewer mounts may be provided than illustrated according to various alternative embodiments.

Figure 9:
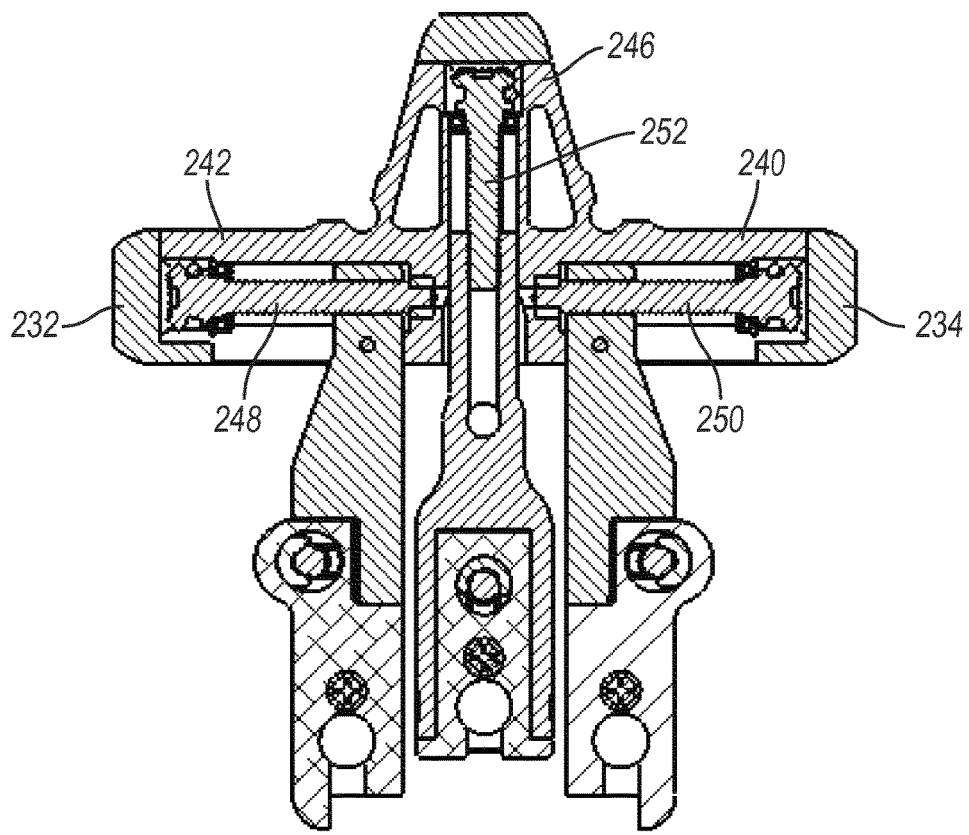
FIG. 9 is a cross-sectional view taken along line 9-9 of FIG. 8 according to one embodiment.
Figure 14:
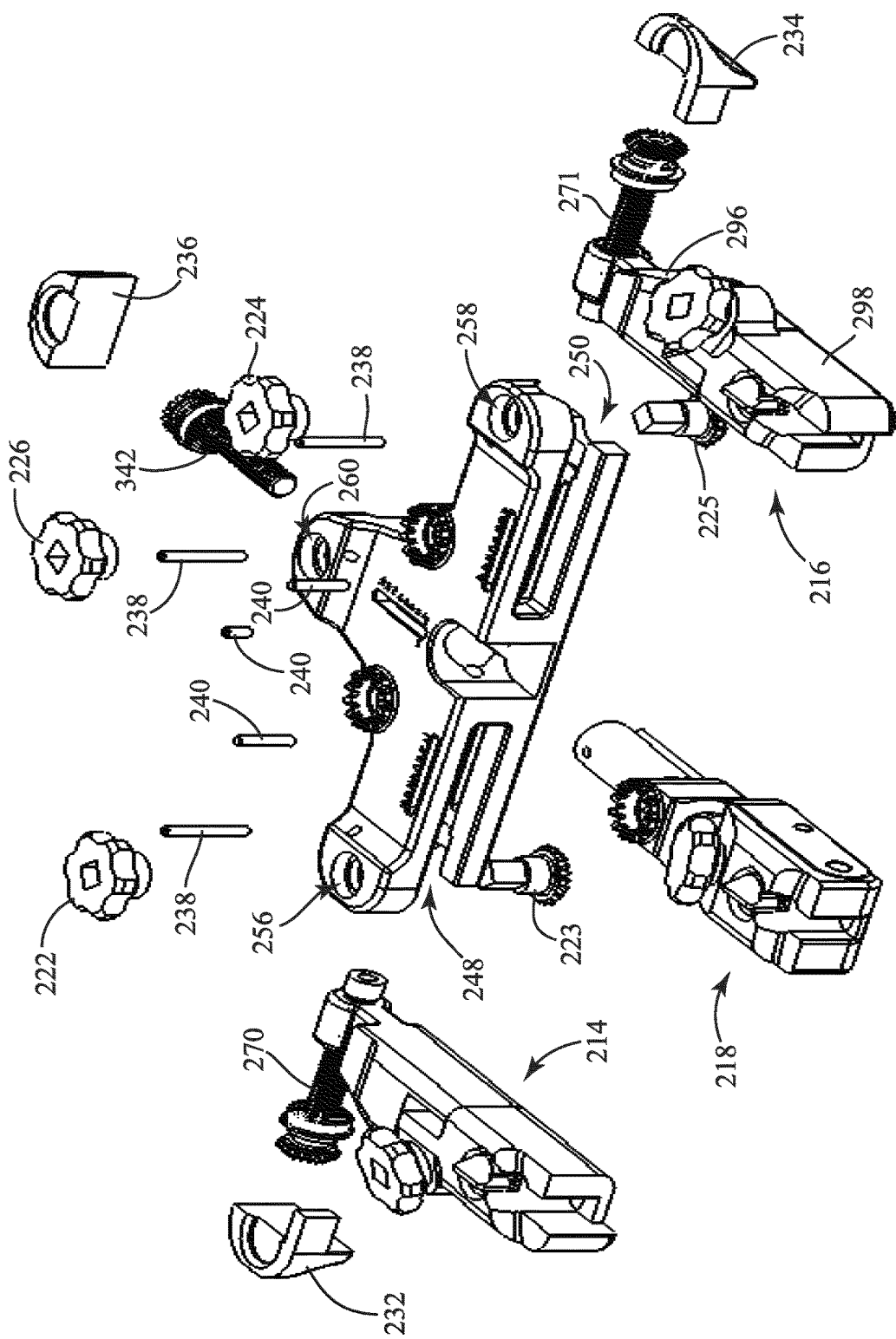
FIG. 14 is an exploded view of the spinal retractor of FIG. 6 according to one embodiment.

Referring FIGS. 9-10 and 14, in some embodiments frame 212 includes first and second side retainers 232, 234. Side retainers are positioned at the lateral ends of frame 212 and form at least a portion of the channels within which assemblies 214, 216 translate. In one embodiment, retainers 232, 234 define a limit to the range of motion of first and second side assemblies 214, 216. Retainers 232, 234 may be coupled to body 220 using any suitable fastening technique, including welding, press fits, mechanical fasteners, and the like. As shown in FIG. 14, a center retainer 236 similarly is coupled to a center portion of body 220 using any suitable fastening technique, including welding, press fits, mechanical fasteners, and the like.

In some embodiments, retaining pins 238 extend through body 220 and, as discussed in greater detail below, are received within annular grooves in threaded members to hold the threaded members in position during use of retractor assembly 210. In one embodiment, three retaining pins 238 are utilized. In other embodiments, more or fewer retaining pins may be used. Further, marker pins 240 may be used in connection with each of first side assembly 214, second side assembly 216, and center assembly 218. Marker pins 240 extend up from assemblies 214, 216, and 218 and through body 220 to provide an indication of the positions of assemblies 214, 216, and 218 relative to body 220, thereby providing a user of retractor assembly 210 a visual indication of the amount of retraction being provided by each of assemblies 214, 216, and 218. In one embodiment, body 220 includes marking gauges 254 (see FIG. 7) having incremental distance markings to provide further information regarding amounts of retraction. Thus, the amount of retraction is indicated by the position of the marking pins 240 along marking gauges 254.

In one embodiment, body 220 includes a first lateral extension 242, a second lateral extension 244, and a central extension 246 (see FIG. 9). First and second lateral extensions 242, 244 generally extend along a common first axis, and central extension 246 generally extends along a second axis perpendicular to the first axis. Central extension 246 is in one embodiment positioned at approximately the midpoint between the opposite ends of first and second lateral extensions 242, 244. A first lateral channel 248 is formed in first lateral extension 242, a second lateral channel 250 is formed in second lateral extension 244, and a central channel or bore 252 is formed in central extension 246. Channels 248, 250, 252 receive end portions of first side assembly 214, second side assembly 216, and center assembly 218, respectively. A first side adjustment aperture 256 is provided on first lateral extension 242, a second side adjustment aperture 258 is provided in second lateral extension 244, and a center adjustment aperture 260 is provided in center extension 246. Adjustment apertures 256, 258, 260 are configured to receive adjustment knobs and/or drive members to enable user-adjustment of first side assembly 214, second side assembly 216, and center assembly 218 relative to body 220.

Referring to FIG. 10, translation of first and second side assemblies 214, 216 is accomplished via rotation of adjustment knobs 222, 224. Adjustment knobs 222, 224 are coupled to drive members 223, 225, which may include bevel gears. Drive members 223, 225 in turn engage bevel gears 267, 269 provided on opposing ends of threaded adjustment members 270, 271, such that rotation of knobs 222, 224 causes a corresponding rotation of adjustment members 270, 271. First and second side assemblies 214, 216 are threadingly received by adjustment members 270, 271 such that rotation of adjustment members 270, 271 causes translation of first and second side assemblies 214, 216. Central assembly is movable in a similar fashion, through use of adjustment knob 226 and adjustment member 342. As such, through selective rotation of knobs 222, 224, and 226, first and second side assemblies 214, 216 and central assembly 218 may be translated independently from one another relative to body or frame 212.

Figure 11:
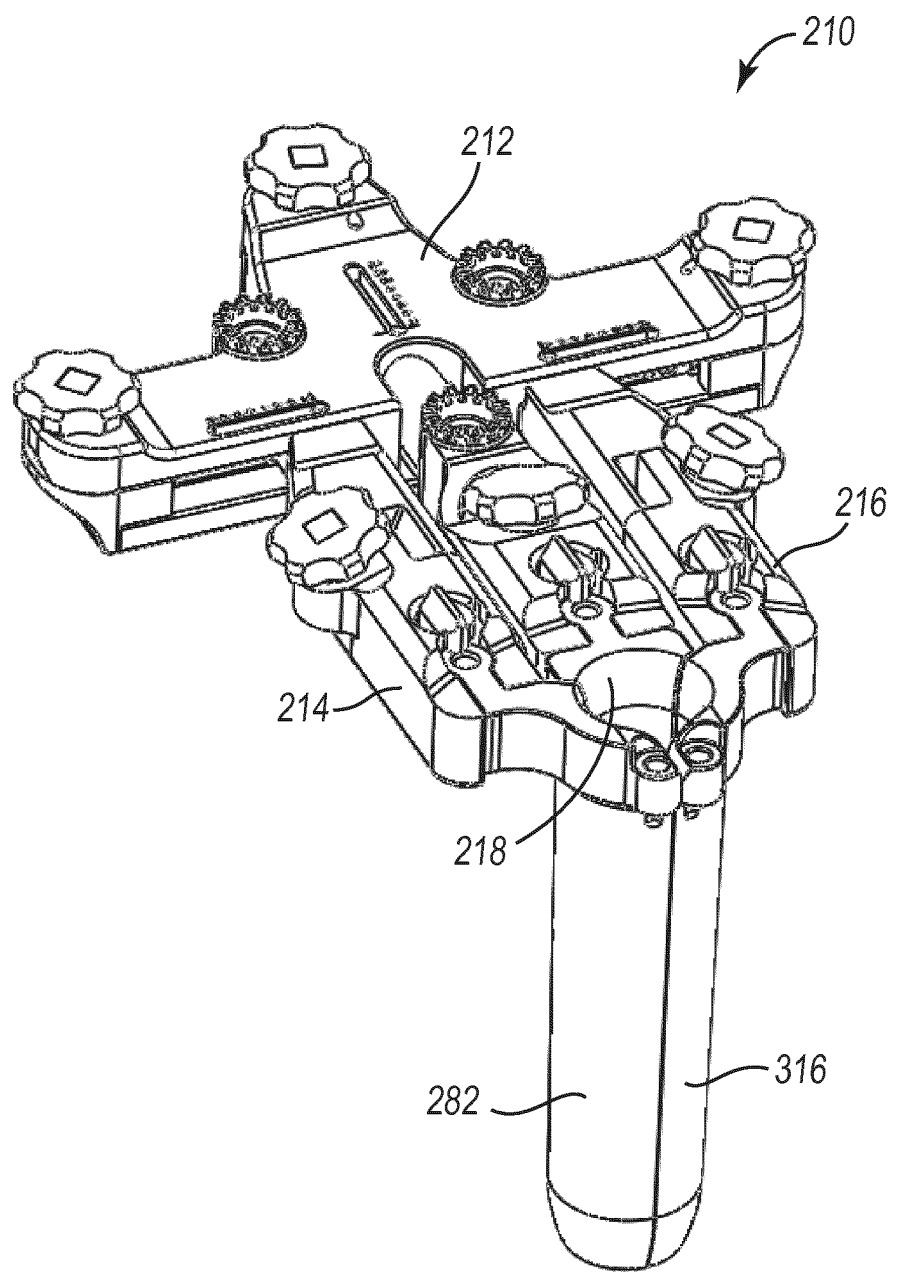
FIG. 11 is a perspective view of a spinal retractor in a closed configuration according to one embodiment.
Figure 12:
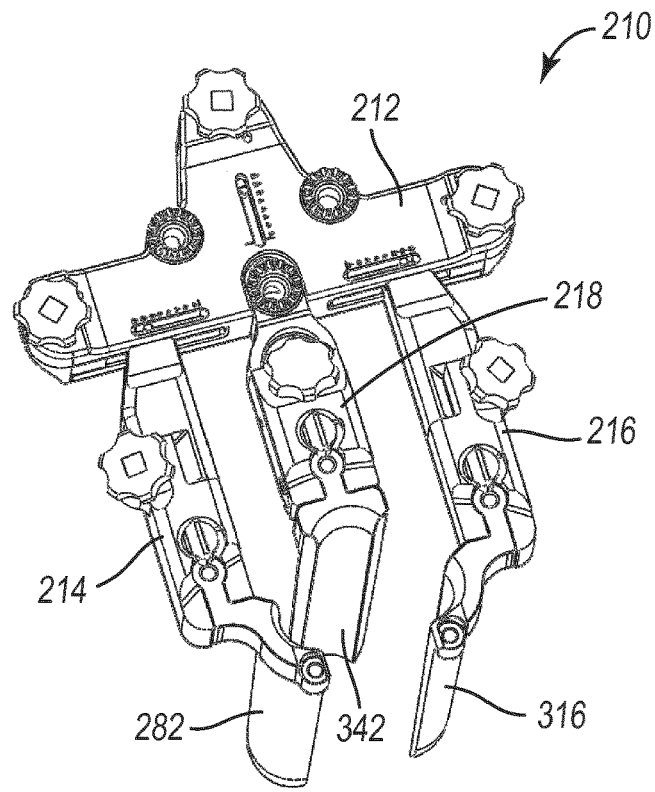
FIG. 12 is a perspective view of the spinal retractor of FIG. 11 in an open configuration according to one embodiment.
Figure 13:
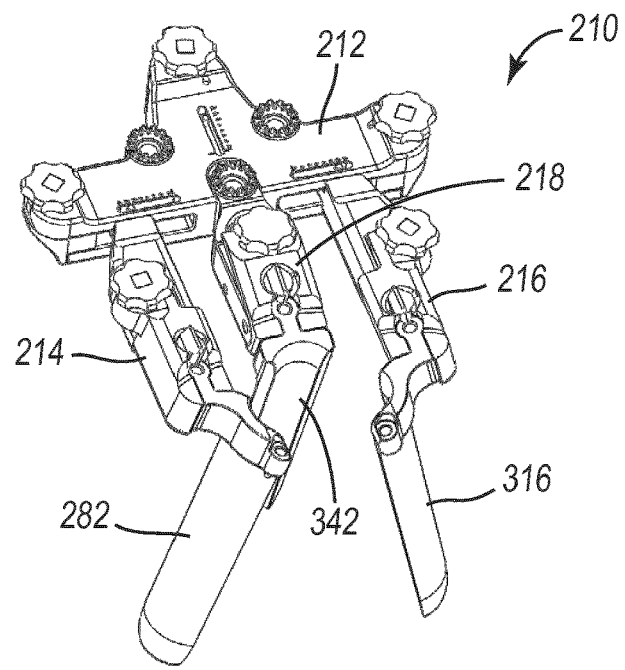
FIG. 13 is a perspective view of the spinal retractor of FIG. 11 in an open configuration with angulated blades according to one embodiment.

Referring to FIGS. 11-13, assembly 210 is movable between a closed configuration, shown in FIG. 11, to an open configuration, shown in FIG. 12, through translation of first and second side assemblies 214, 216 and/or central assembly 218 relative to body 220. Furthermore, first and second side assemblies 214, 216 and central assembly 218 receive blade assemblies 282, 316, and 348, respectively, which are configured to hold tissue apart during various procedures. As shown in FIGS. 12 and 14 and as discussed in greater detail below, blade assemblies 282, 316, 342 may be angulated (e.g., moved from a generally vertical orientation to one or more non-vertical, or angled, orientations) to suit a particular procedure.

Figure 15A:
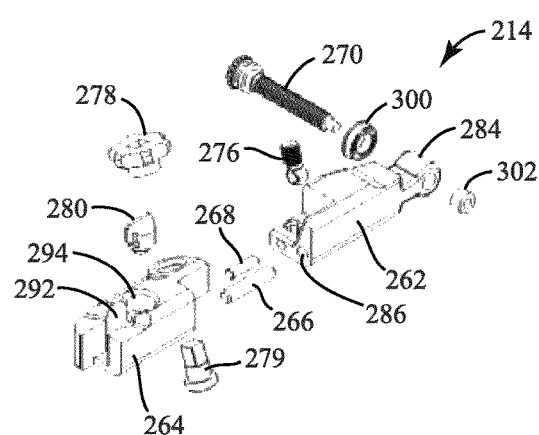
FIGS. 15A-15B illustrate a side assembly of a spinal retractor according to one embodiment.
Figure 15B:
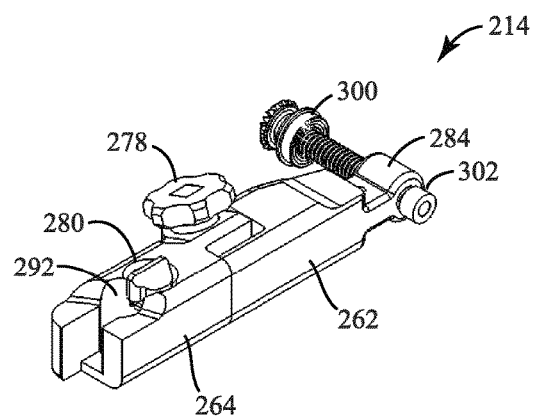

Referring now to FIGS. 15A-15B, first side assembly 214 is shown in greater detail according to one embodiment. Assembly 214 includes a first arm portion 262 coupled to a second arm portion 264. First arm portion 262 and second arm portion 264 can take any suitable size and/or shape, and be coupled together using a variety of coupling methods.

Figure 18A:
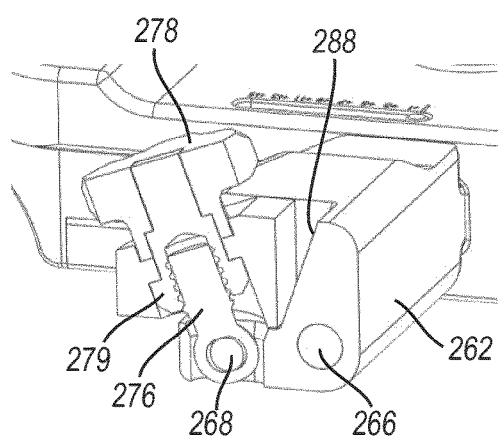
FIGS. 18A-19B illustrate various portions of a spinal retractor according to one embodiment.
Figure 18B:
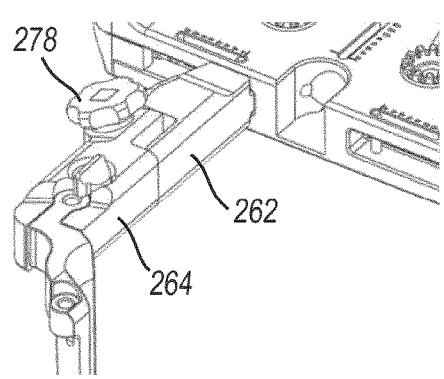
Figure 19B:
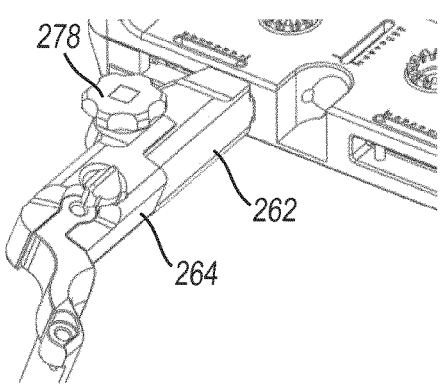
Figure 21C:
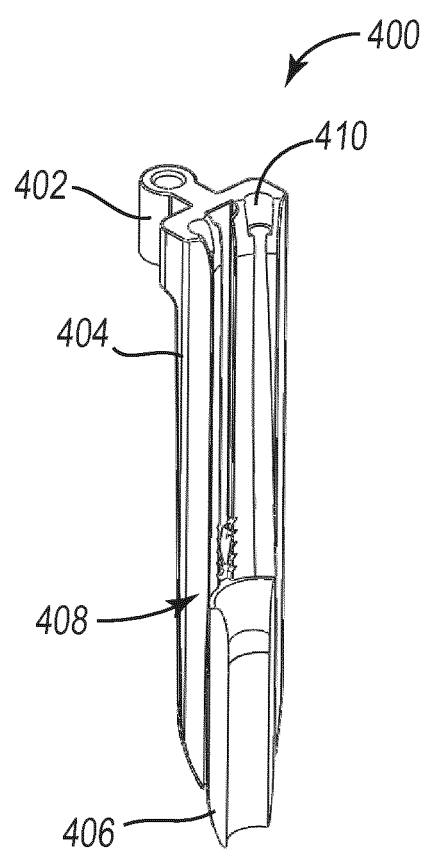

In one embodiment, first arm portion 262 is translatable relative to frame 212, but rotatably fixed relative to frame 212, and second arm portion 264 is rotatably coupled to first arm portion 262. As shown in FIGS. 18A-19B, second arm portion rotates relative to first arm portion 262 about a first pivot pin 266. An adjustment knob 278 is coupled to an insert 279 which threadingly engages an angulation adjustment member 276. Member 276 includes a threaded shaft and rotates about a second pivot pin 268. As shown in FIGS. 18A-19B, as a user turns knob 278, the angular position of second arm portion 264 relative to first arm portion 262 changes due to the travel of insert 279 along member 276, providing angular adjustability of the associated blade assemblies. For example, as shown in FIGS. 18A-B, first and second arm portions 262, 264 are generally aligned, and knob 278 is in a first position. Upon turning knob 278, knob 278 moves to a second position, shown in FIGS. 19A-B, and second arm portion 264 moves to an angulated position with respect to first arm portion 262, thereby enabling additional retraction of surrounding tissue, etc.

Figure 19A:
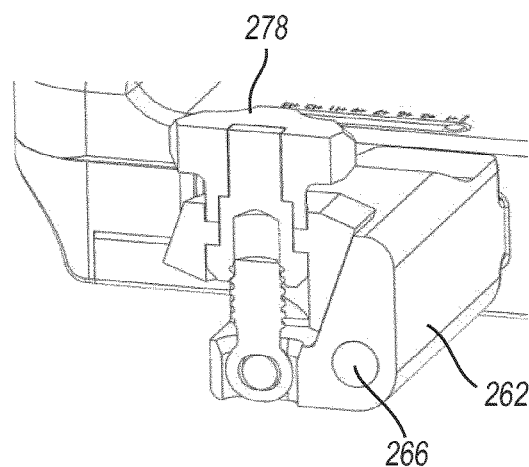

Referring to FIG. 15A, first arm portion 262 includes an internally threaded cylindrical portion 284. Portion 284 is received within channel 248 and translates therein. In some embodiments, the outer contour of portion 284 generally corresponds in shape to the inner contour of channel 248 such that portion 284 is limited to translational movement within channel 248. In one embodiment, portion 284 is received within bushings 300, 302, which are provided on threaded member 270 and may act to enable rotation of threaded member 270 within channel 248 and/or define the range of motion of portion 284. First arm portion 262 further includes pin apertures 286, which are sized and shaped to receive first and second pivot pins 266, 268. In order to provide the angulation of second arm portion 264, first arm portion 262 further includes an adjustment surface 288. As shown in FIGS. 18A and 19A, adjustment surface 288 in one embodiment limits the total amount of angulation of second arm portion 264 relative to first arm portion 262.

Second arm portion 264 includes a blade receiving portion 292 and a blade lock bore 294. Blade receiving portion 292 is configured to receive first side blade assembly 282, and blade lock bore 294 is configured to receive blade lock 280. In one embodiment, blade lock 280 includes a non-circular head such that blade lock 280 is rotatable within blade lock bore 294 into and out of an interfering position relative to first side blade assembly 282 when first side blade assembly 282 is received within blade receiving portion 292. As such, first side blade assembly 282 may be slidingly received within blade receiving portion 292 and subsequently maintained in position relative to second arm portion 264 by way of blade lock 280.

Second side assembly 216 in one embodiment operates in a similar manner to first side assembly 214, and includes similar components, including a first arm portion 296 and a second arm portion 298, which receives second side blade assembly 316.

Figure 16A:
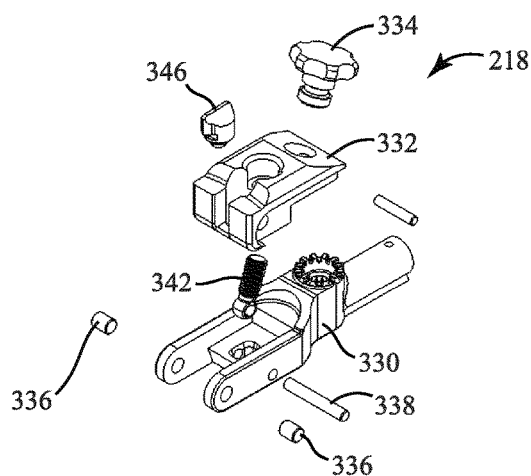
FIGS. 16A-16B illustrate a central assembly of a spinal retractor according to one embodiment.
Figure 16B:
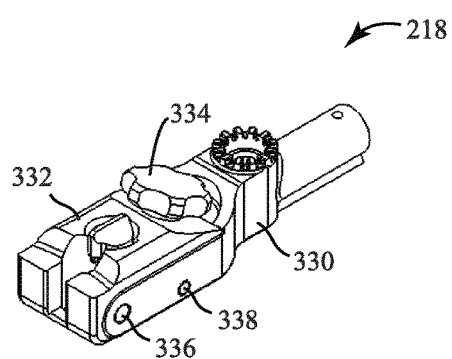

Referring to FIGS. 16A-16B, center assembly 218 includes a first arm portion 330 and second arm portion 332 pivotally coupled to first arm portion 330 via pivot pins 336. An angulation knob 334 threadingly engages an adjustment member 342 to cause rotation of adjustment member 342 about angulation pivot pin 338. Center blade assembly 342 is received by second arm portion 332 and retained in place by a blade lock 346. Rotation of adjustment knob 344 causes a corresponding change in the angulation of center blade assembly 342.

Figure 17:
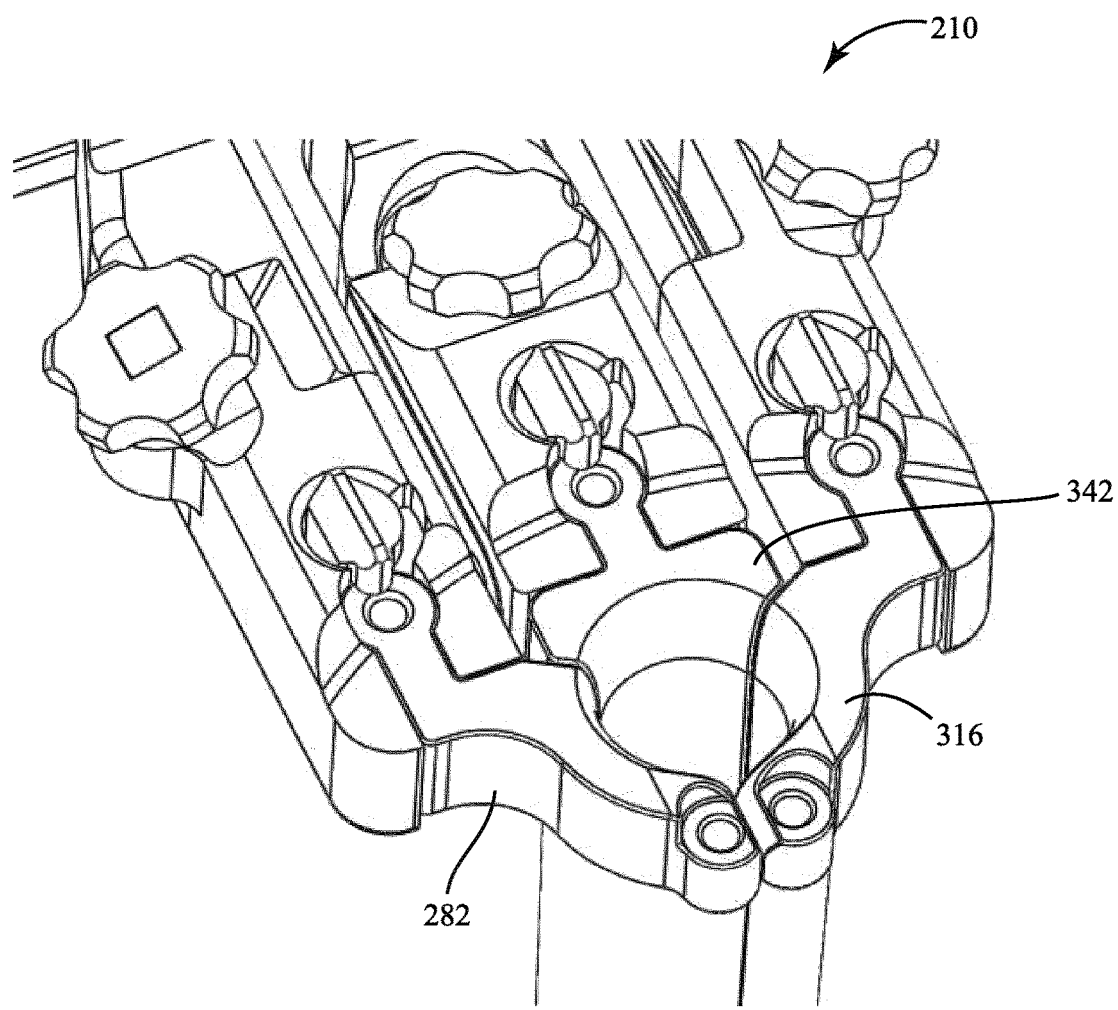
FIG. 17 is a perspective view of a portion of a spinal retractor according to one embodiment.

Referring now to FIG. 17, in one embodiment, blade assemblies 282, 316, 342 form a circular interior when spinal retractor 210 is in the closed position and blade assemblies 282, 316, and 342 are in a non-angulated orientation. Dependent upon a desired type and degree of distraction, the various side and center assemblies and blade assemblies may be moved to desired positions to provide the desired retraction for a particular procedure.

Referring to FIGS. 20A-21C, a blade assembly 400 is shown according to an alternative embodiment. The features of blade assembly 400 may be implemented with any of blade assemblies 282, 316, and 342. In one embodiment, blade assembly 400 includes a blade support 402 coupled to a primary blade 404. A secondary blade 406 is removably and adjustably coupled to primary blade 404 via a ratchet mechanism 408. One or more channels 410 may be provided in primary blade 404 to enable insertion of light sources, fixation pins, or other components. For example, in some embodiments, upon positioning blade assembly 400 in a desired retraction position, one or more fixation pins may be placed within channel 410 to secure the blade(s) in place. Use of secondary blade 406 is in some embodiments optional, and enables, for example, prevention of tissue creep during procedures and eliminated the need to change to a longer blade during a procedure.

In use, spinal retractor 210 is positioned at a desired position relative to a patient, and may be secured using one or more of table arm mounts 228, 230, 231. Spinal retractor 210 is normally initially in a closed configuration (see, e.g., FIG. 11). Spinal retractor may be moved to a desired open configuration by translating one or more of first side assembly 214, second side assembly 216, and center assembly 218 relative to base 212. Further, one or more of blade assemblies 282, 316, or 342 (or similarly, blade assembly 400), may be angulated into a desired position of angulation. In some embodiments, a secondary blade may be utilized to prevent tissue creep during a procedure, and one or more components (e.g., lights, fixation pins, etc.) may be utilized via one or more of the blade assemblies.

Referring now to FIGS. 22-32C, a spinal retractor 510 is shown according to another alternative embodiment. The spinal retractor 510 shown in FIGS. 22-30 shares many of the features of the spinal retractors shown in FIGS. 1-5 and 6-21, and all such features are understood to be part of the embodiment shown in FIGS. 22-30.

Figure 22:
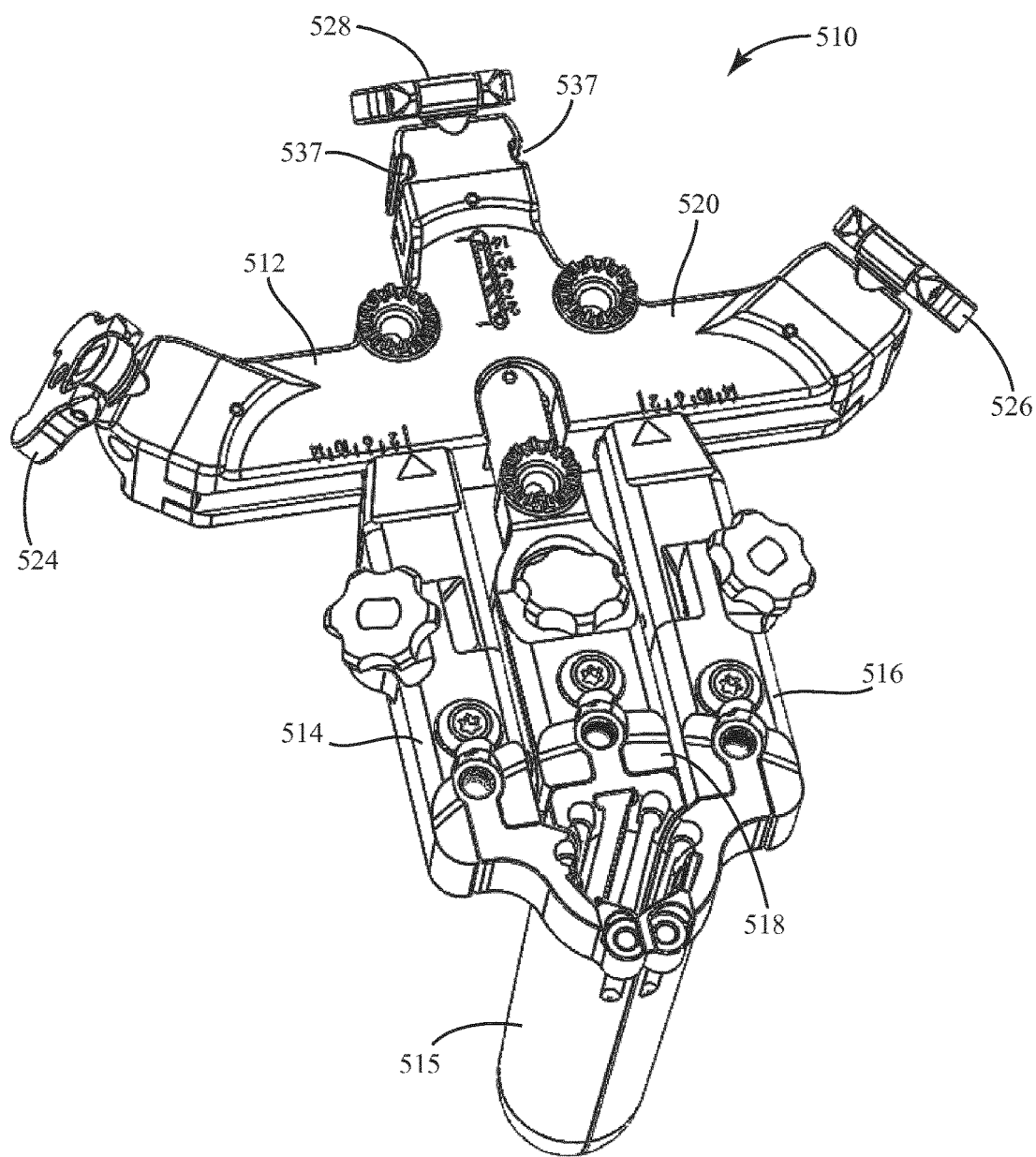
FIG. 22 is a perspective view of a spinal retractor according to another embodiment.
Figure 23:
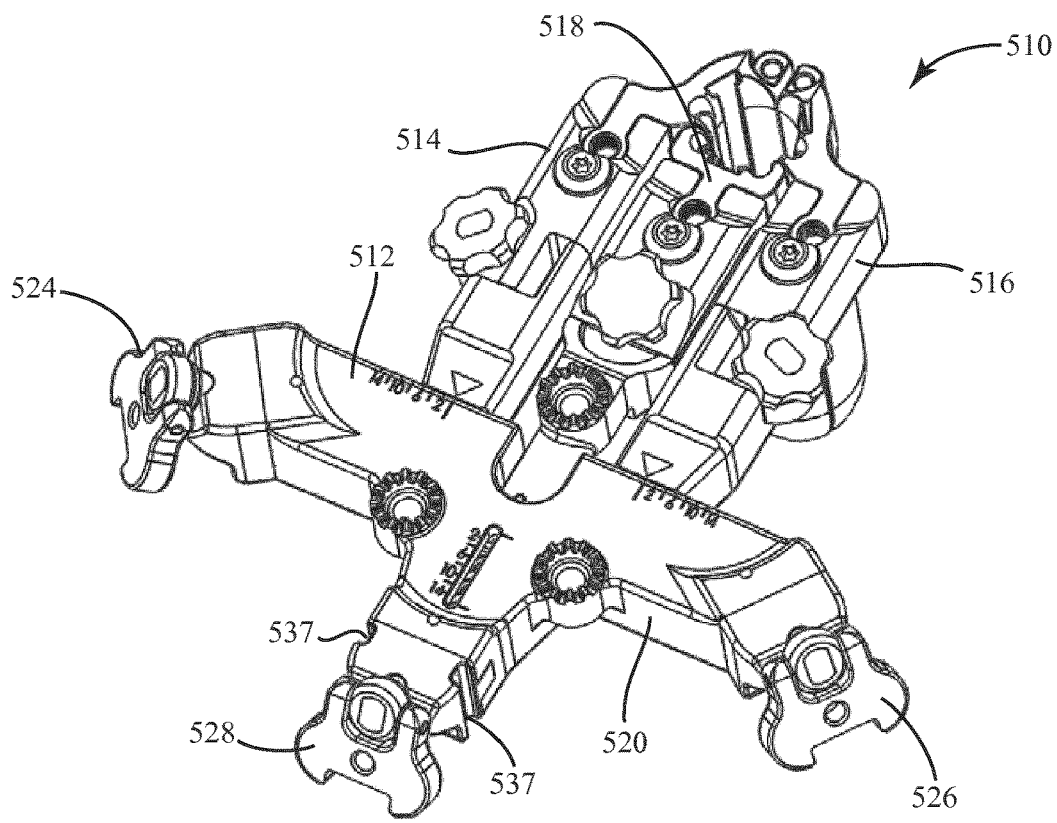
FIGS. 23-24 are additional perspective views of the spinal retractor of FIG. 22 according to one embodiment.
Figure 24:
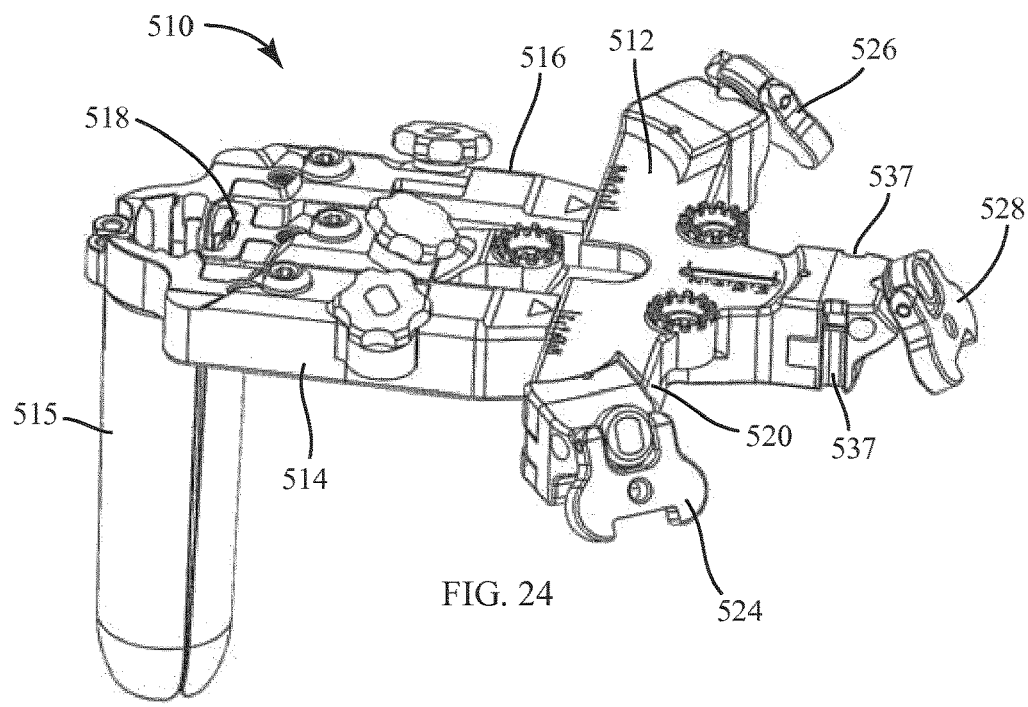

Referring to FIGS. 22-24, the spinal retractor 510 includes a frame or base 512, a first side assembly 514, a second side assembly 516, and a center assembly 518. The first side assembly 514, the second side assembly 516, and the center assembly 518 are coupled to the base 512 to enable translating movement of the assemblies 514, 516, and 518 relative to the base 512 to provide retraction of tissue, etc. during surgical procedures involving the spine, etc. The first side assembly 514 and the second side assembly 516 translate relative to the base 512 in a medial-lateral direction (e.g., along a first axis or direction), and the center assembly 518 translates relative to the base 512 in a cephalad-caudal direction (e.g., along a second axis or direction) in a generally perpendicular fashion relative to the first and second side assemblies. In one embodiment, each of the assemblies 514, 516, 518 may be adjusted (e.g., translated) relative to the base 512 independently (e.g., such that each of the first side assembly 514, the second side assembly 516, and the center assembly 518 may be adjusted individually).

The base 512 includes a body 520, a first side adjustment knob or member 524, a second side adjustment knob or member 526, and a center adjustment knob or member 528. The first side adjustment knob 524 is operatively coupled to the first side assembly 514, the second side adjustment knob 526 is operatively coupled to the second side assembly 516, and the center adjustment knob 528 is operatively coupled to the center assembly 518, such that adjustment of knobs 524, 526, 528 causes a corresponding translational movement of the assemblies 514, 516, 518.

Figure 25:
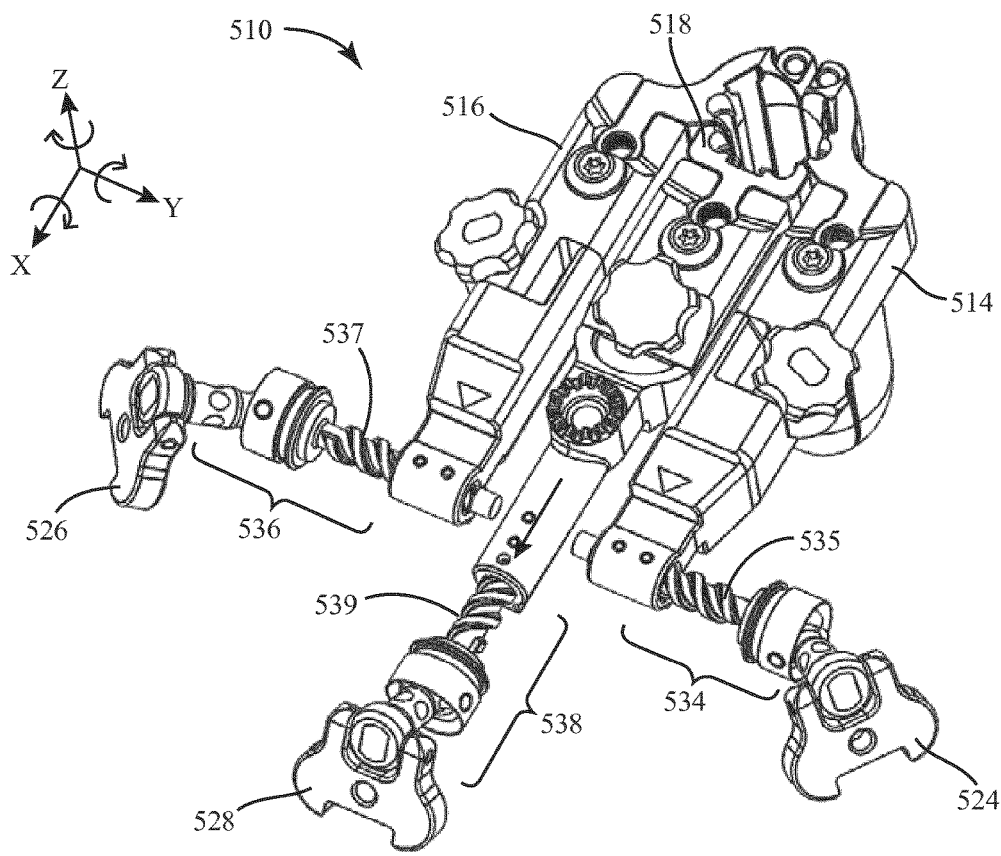
FIGS. 25-26 are perspective views of portions of the spinal retractor of FIG. 22 according to one embodiment.
Figure 26:
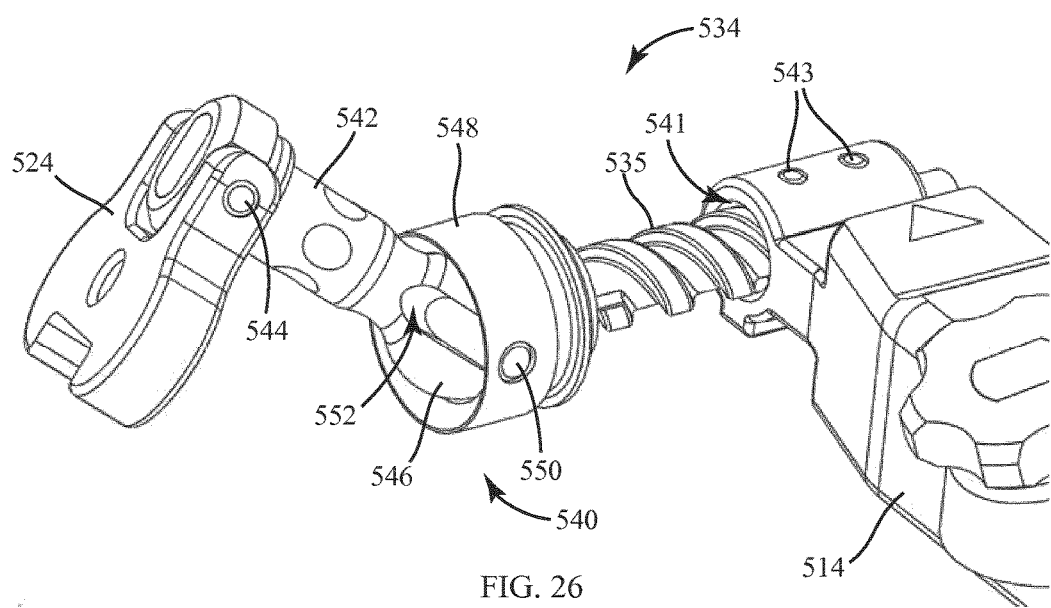

Referring to FIGS. 25-26, the first side adjustment knob 524 is coupled to a first threaded shaft 535 via a first side drive assembly 534, the second side adjustment knob 526 is coupled to a second threaded shaft 537 via a second side drive assembly 536, and the center adjustment knob 528 is coupled to a third threaded shaft 539 via a center drive assembly 538. The first side drive assembly 534, second side drive assembly 536, and center drive assembly 538 are similar in structure and function, and therefore only first side drive assembly 534 will be discussed in detail with respect to FIG. 26. However, it should be understood that any features shown and described with respect to the first side drive assembly 534 are equally applicable to the second side drive assembly 536 and the center drive assembly 538.

As shown in FIG. 26, the first side drive assembly 534 is operatively coupled to the first threaded shaft 535 via a first multi-axis joint assembly, shown as ball joint assembly 540. The first threaded shaft 535 is received in a bore 541 in the first side assembly 514. The first threaded shaft 535 engages one or more elements, shown as pins 543, that extend into the bore 541. Through the interaction between the pins 543 and the first threaded shaft 535, the first threaded shaft 535 advances into or withdraws from the bore 541 as the first threaded shat 535 is rotated. In other embodiments, the first threaded shaft 535 may otherwise engage the bore 541 in the first side assembly 514. For example, the bore 541 may be formed with an internal thread configured to engage the first threaded shaft 535.

The ball joint assembly 540 includes a drive shaft 542 pivotally coupled at a first end to the first side adjustment knob 524 by a pivot pin 544. The second end of the drive shaft 542 is in the form of a ball 546 that is adjustably coupled to a receiver 548 via a cross pin 550. The ball 546 defines a slot 552 sized to receive the cross pin 550 such that the drive shaft 542 can pivot about multiple axes (e.g., such that the first end of the drive shaft 542 is rotatable through a semi-spherical range of motion). For example, in a non-rotated position, the drive shaft 542 extends generally collinearly with the first threaded shift 535. When put into the position shown in FIG. 25, the drive shaft 542 is able to rotate about both the X-axis 554 and the Z-axis 556 shown in FIG. 25. Providing an angular offset for the drive shaft 542, and in turn, the first side adjustment knob 524, may provide a more advantageous position for adjusting the spinal retractor 510. In some embodiments, the first side drive assembly 534 is operatively coupled to the first threaded shaft 535 via another moveable coupling member that allows the drive shaft 542 to pivot about multiple axes (e.g., such that the first end of the drive shaft 542 is rotatable through a semi-spherical range of motion). For example, in some embodiments, the first side drive assembly 534 may be operatively coupled to the first threaded shaft 535 via a universal joint mechanism. Other types of multi-axis joints or coupling mechanisms may be used according to various alternative embodiments.

The spinal retractor 510 is movable between a closed configuration, shown in FIG. 22, to an open configuration, through translation of the first side assembly 514 and the second side assembly 516 and/or the center assembly 518 relative to the body. Furthermore, the first side assembly 514, the second side assembly 516, and the center assembly 518 receive blade assemblies 515, which are configured to hold tissue apart during various procedures. The blade assemblies 515 may be angulated (e.g., moved from a generally vertical orientation to one or more non-vertical, or angled, orientations) to suit a particular procedure. The first and second side assemblies and the center assembly may further include first and second portions such as those described with respect to FIGS. 15A-16B to provide further adjustment capabilities for the spinal retractor 510.

Figure 27:
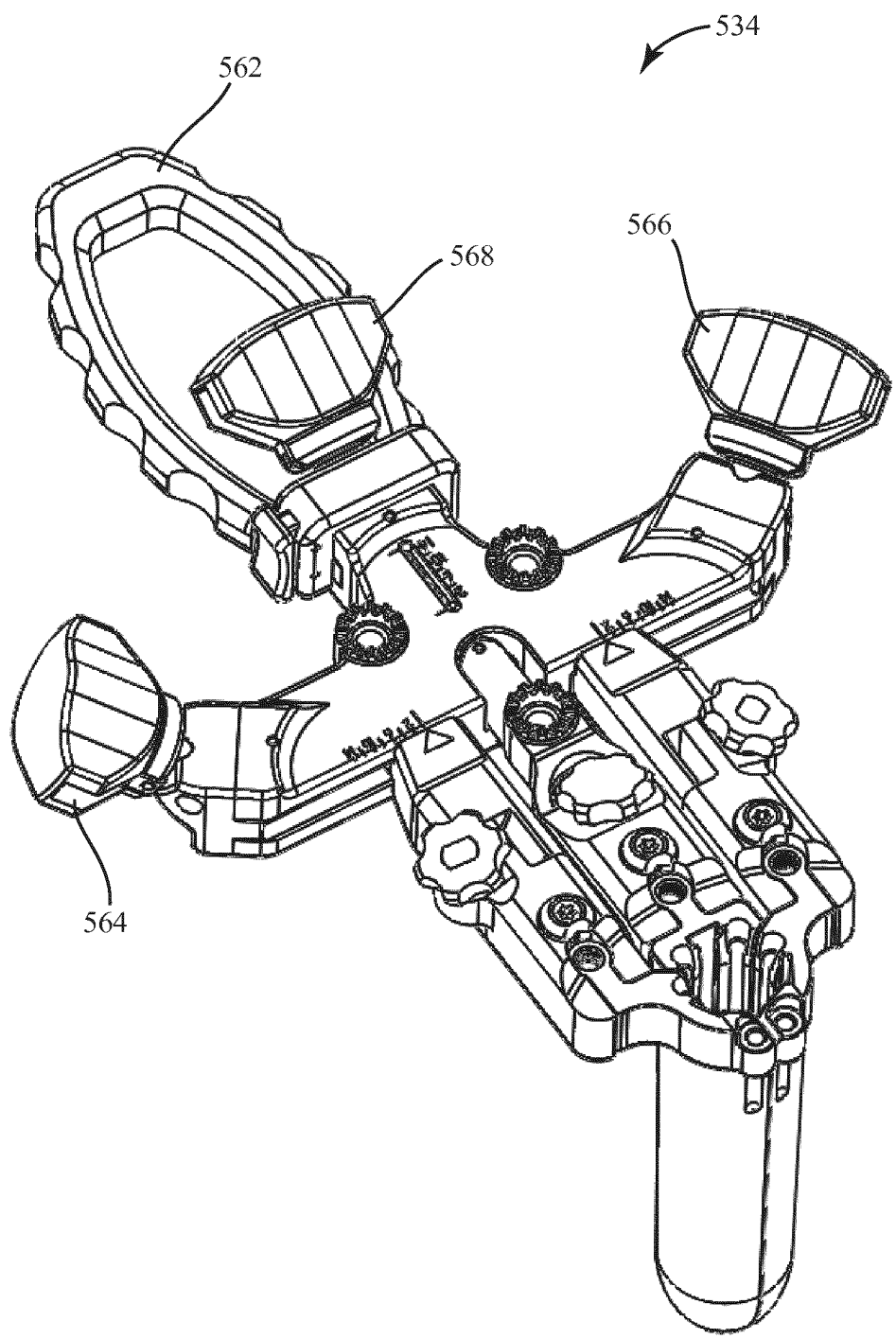
FIG. 27 is a perspective view of the spinal retractor of FIG. 22 with various handles attached according to one embodiment.

Referring now to FIGS. 27-30, the spinal retractor 510 is shown coupled to one or more handles. For example, as shown in FIG. 27, a first adjustment handle 564 is coupled to the first side adjustment knob 524, a second adjustment handle 566 is coupled to the second side adjustment knob 526, a third adjustment handle 568 is coupled to the center adjustment knob 528, and a support handle 562 is coupled to the base 512. The various handles are in one embodiment attached in a removable fashion such that the handles can be selectively attached/detached during use of the spinal retractor 510.

Figure 28:
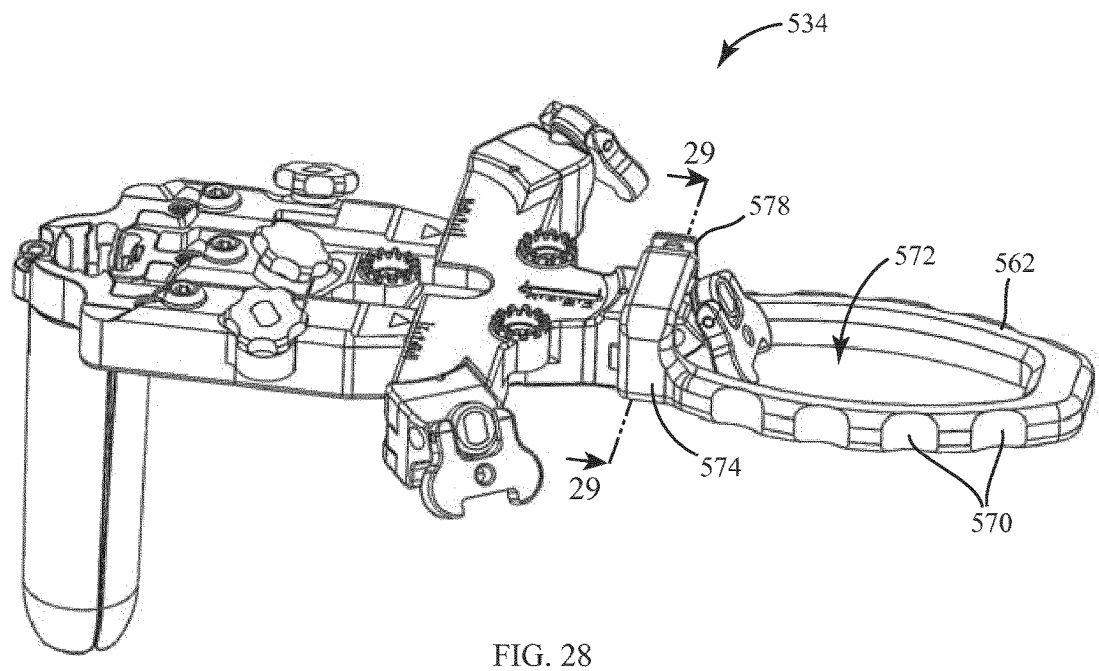
FIG. 28 is a perspective view of the spinal retractor of FIG. 22 with a support handle attached according to one embodiment.
Figure 29:
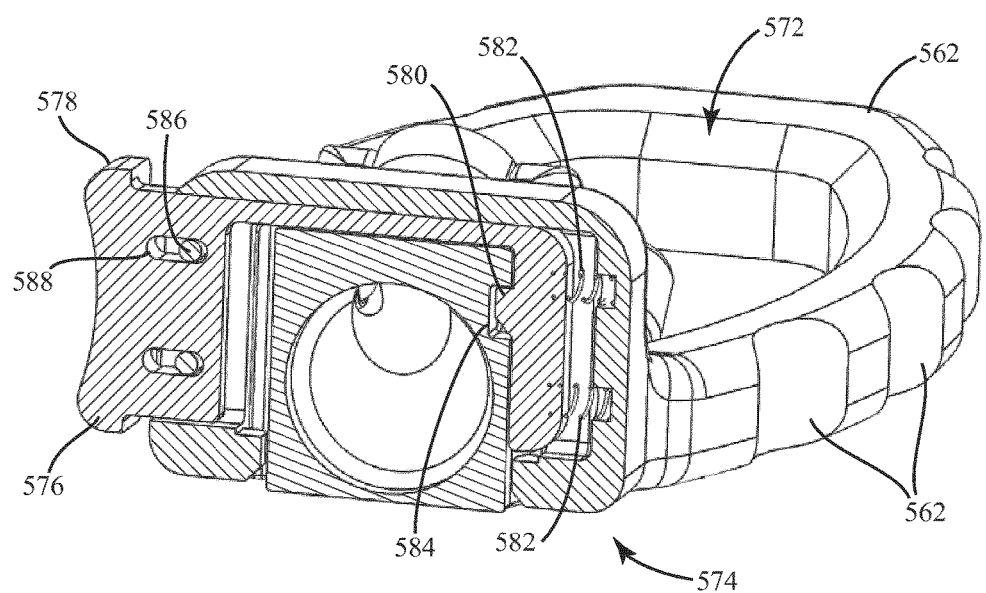
FIG. 29 is a perspective cross-sectional view of the spinal retractor of FIG. 22 taken along line A-A of FIG. 28 according to one embodiment.

As shown in FIGS. 28 and 29, the support handle 562 is coupled to the base 512 adjacent the center adjustment knob 528. The support handle 562 defines a plurality of grip portions 570 and a central aperture 572. In one embodiment, the support handle 562 is a substantially rigid member, while in alternative embodiments, the support handle 562 is a flexible and/or compressible member (e.g., such that the opposing sides of the support handle 562 are deformable inward toward each other). In some embodiments, the grip portions 570 are shaped to generally correspond to the shapes of the fingers of a user to prevent slippage between the spinal retractor and a hand of a user.

Referring to FIG. 29, in one embodiment, the support handle 562 includes a handle attachment portion 574 that is received in a groove 275 in the base 512 (see FIG. 22). As such, the support handle 562 may be slidably attached and detached relative to the base 512. As shown in FIG. 29, the attachment portion 574 includes a locking plate 576 defining a button 578 and projection 580. The locking plate 576 is received by the groove 275, and a pair of springs 582 bias the projection 580 into a recess 584 formed in the base 512 (e.g., as part of the groove 275). A pair of guide pins 586 received in slots 588 in the locking plate 576 maintain proper alignment of the locking plate 576. Depression of the button 578 disengages the projection 580 from the recess 584 and enables detachment of the support handle 562 from the base 512.

Figure 30:
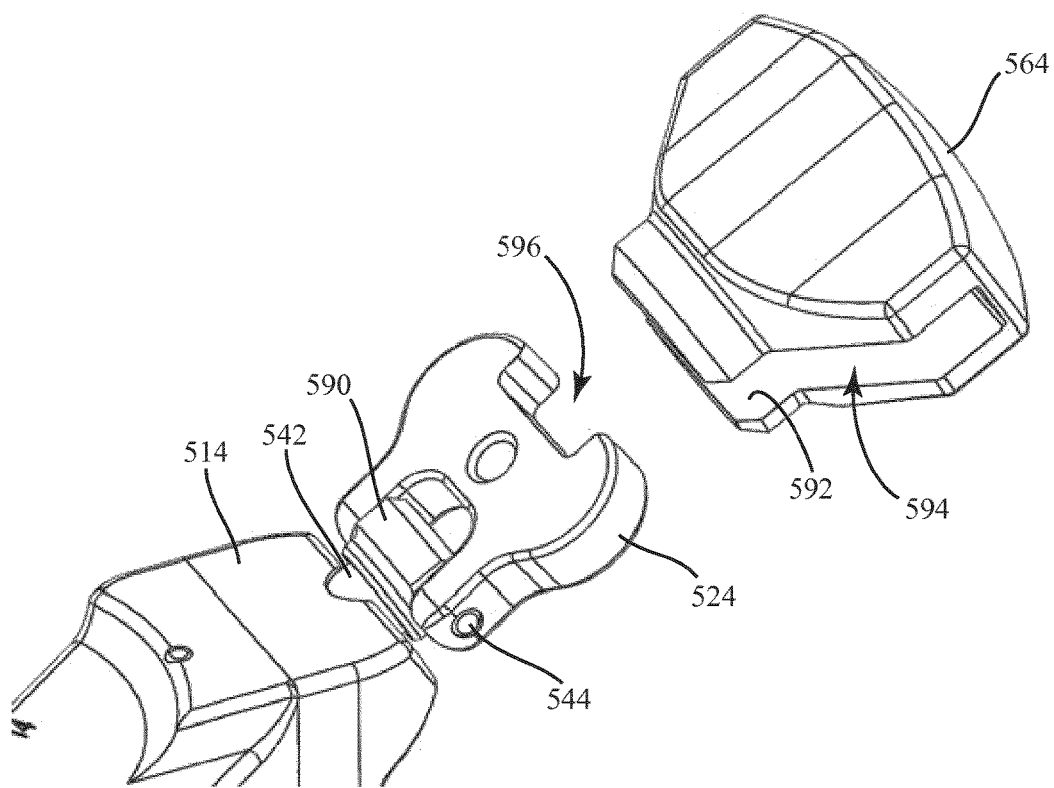
FIG. 30 is an exploded view of a portion of a spinal retractor according to one embodiment.
Figure 31A:
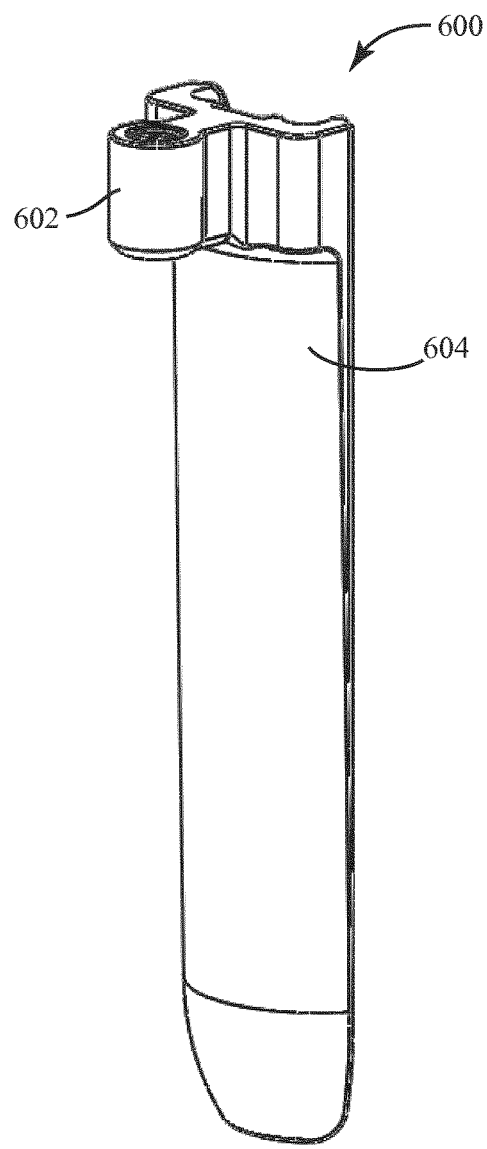
FIGS. 31A-32C are various views of primary and secondary blades according to various exemplary embodiments.
Figure 31B:
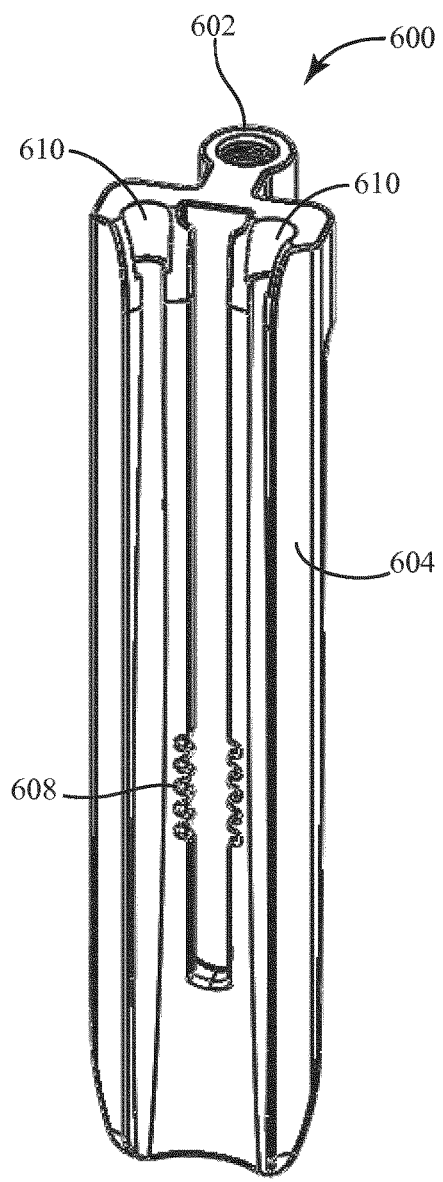
Figure 32A:
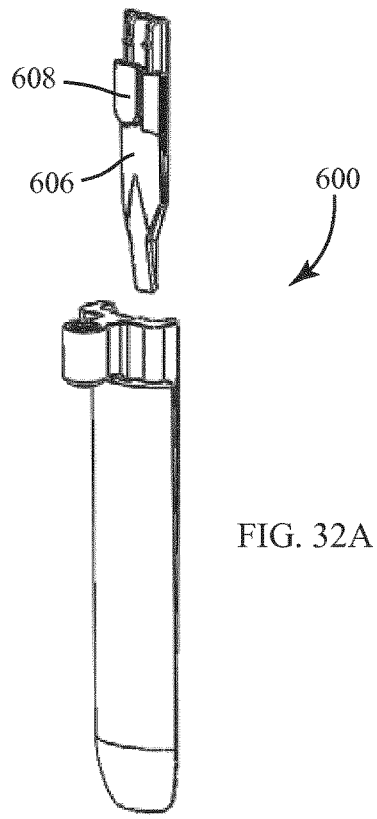
Figure 32B:
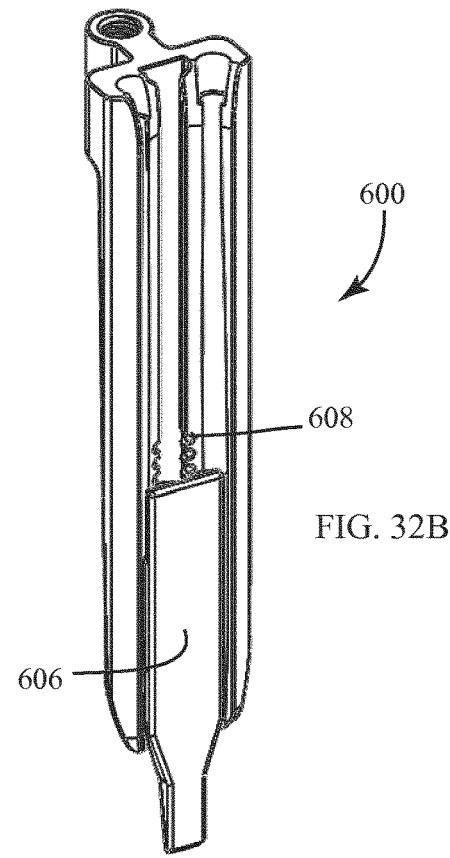
Figure 32C:
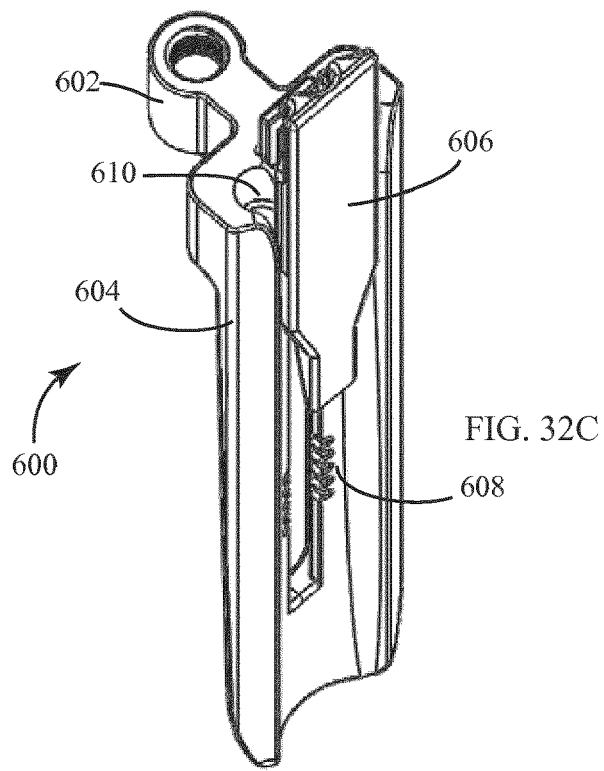

Referring to FIG. 30, the first adjustment handle 564 is shown removed from the first side adjustment knob 524. When the first adjustment handle 564 is detached, the first side adjustment knob 524 is free to rotate about the pivot pin 544. When the first adjustment handles 564 is attached, one or more flat portions 590 on the drive shaft 542 interface one or more flat portions 592 on the first adjustment handle 564 to resist rotation of the first side adjustment knob 524 relative to the drive shaft 542. In one embodiment, when the first adjustment handle 564 is coupled to the first side adjustment knob 524, the first adjustment handle 564 extends in a direction generally collinear with the axis of the drive shaft 542. In other embodiments, the first adjustment handle 564 may extend in other directions. The first adjustment handle 564 defines a slot 594 in which the first side adjustment knob 524 is received. A protrusion within the slot 594 engages a corresponding channel 596 to align the first adjustment handle 564 with the first side adjustment knob 524 and limits the movement of the first adjustment handle 564 with respect to the first side adjustment knob 524.

Referring to FIGS. 31A-32C, a blade assembly 600 is shown according to one embodiment. The blade assembly 600 may be similar in construction and features to the blade assembly 400 and may be implemented with any of blade assemblies 282, 316, 342, and 400. In one embodiment, blade assembly 600 includes a blade support 602 coupled to a primary blade 604. A secondary blade 606 is removably and adjustably coupled to primary blade 604 via a ratchet mechanism 608 (e.g., using one or more projections that are biased into one or more recesses to provide adjustable positioning of the secondary blade 606). One or more channels 610 may be provided in primary blade 604 to enable insertion of light sources, fixation pins, or other components. For example, in some embodiments, upon positioning blade assembly 600 in a desired retraction position, one or more fixation pins may be placed within channel 610 to secure the blade(s) in place. Use of secondary blade 606 is in some embodiments optional, and enables, for example, prevention of tissue creep during procedures and eliminated the need to change to a longer blade during a procedure.

It should be understood that the spinal retractor shown in FIGS. 22-30 may share any or all of the features described elsewhere herein, including blade extenders/supplemental blades, blade locking features, lighting features extending within channels in the blades, and the like. All such combinations of features are to be understood to be within the scope of the present disclosure.

In one embodiment, in operating a spinal retractor such as one described herein, the retractor is placed into a desired position. A first side assembly, a second side assembly, and a center assembly of the retractor are translated along threaded shafts relative to a frame of the retractor. The side and center assemblies may be translated via manipulation of ball joint assemblies that couple adjustment knobs to the respective threaded shafts.

The spinal retractor shown and described herein may provide various benefits over more traditional designs. The support handle provides a modular, ergonomic handle for improved manipulation of the base or frame to ease alignment of the device, and the adjustment handles provide modular ergonomic handles for translation of the side and center assemblies without the need for additional instrumentation. Further, the adjustment handles stabilize the positions of the adjustment knobs for ease of use. The gear rations of the threaded shafts provide faster translation of components (e.g., twice as fast as certain conventional device) such that each of the side and center assemblies can be completely expanded with 1.5 revolutions of the threaded shafts/adjustment knobs.

Additionally, the frame weight is less compared to more traditional devices (e.g., by 15 percent or more), and the frame geometry is optimized to enable table arm attachment to the center arm assembly while eliminating interference with the base or frame (e.g., in situations when the table arm extends generally parallel to the length of the frame or base). In some embodiments, blade extenders include self-retaining springs to ensure the blade extenders remain captured within the blades, and the blade locking mechanisms provide a spring-activated locking feature requiring only a one quarter turn to lock/unlock the blades. Further, light sources may extend down channels in the blades to provide optimized lighting (e.g., 15 percent or more light output relative to more traditional designs).

Referring now to FIGS. 33-54, a spinal retractor 710 is shown according to another alternative embodiment. The spinal retractor 710 shown in FIGS. 33-54 shares many of the features of the spinal retractors shown in FIGS. 1-5, 6-21, and 22-32, and all such features are understood to be part of the embodiment shown in FIGS. 33-54.

Referring to FIGS. 33-38, the spinal retractor 710 includes a frame or base 712, a first side assembly 714, a second side assembly 716, and a center assembly 718. The first side assembly 714, the second side assembly 716, and the center assembly 718 are coupled to the frame 712 to enable translating movement of the assemblies 714, 716, and 718 (or portions thereof) relative to the frame 712 to provide retraction of tissue, etc. during surgical procedures involving the spine, etc. The first side assembly 714 and the second side assembly 716 translate relative to the frame 712 in a medial-lateral direction (e.g., along a first axis or direction), and the center assembly 718 translates relative to the frame 712 in a cephalad-caudal direction (e.g., along a second axis or direction) in a generally perpendicular fashion relative to the first and second side assemblies. In one embodiment, each of the assemblies 714, 716, 718 may be adjusted (e.g., translated) relative to the frame 712 independently (e.g., such that each of the first side assembly 714, the second side assembly 716, and the center assembly 718 may be adjusted individually).

Figure 46:
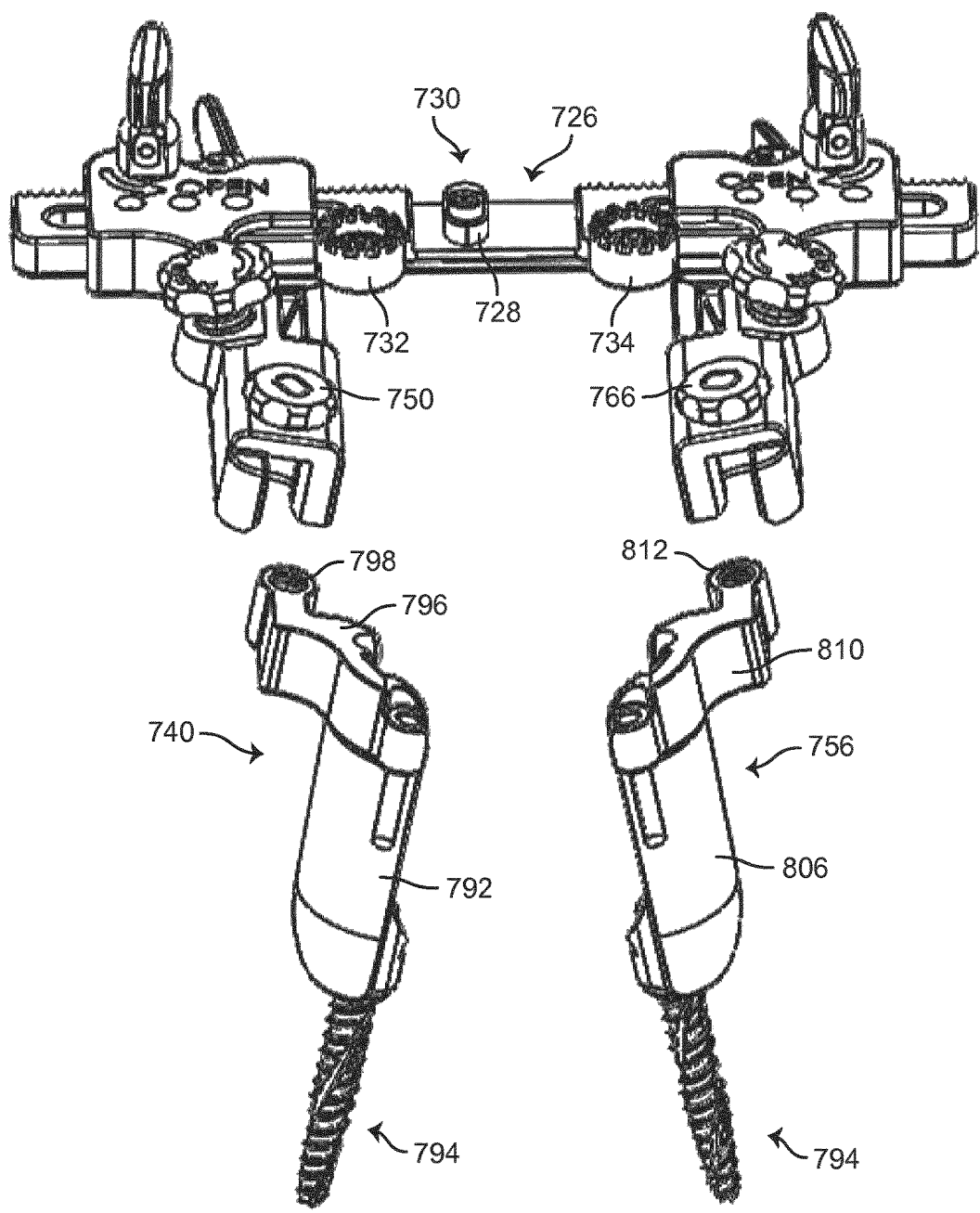
FIG. 46 is a perspective view of first and second blade assemblies decoupled from a spinal retractor according to one embodiment.

The frame 712 is in one embodiment a generally elongated member (e.g., a rail, etc.) including a first side slot 720 and a second side slot 722 extending along the longitudinal direction of the frame 712. Frame teeth 724 extend along all or a part of the frame 712 and facilitate adjustment of the first and second side assemblies 714, 716 along the frame 712. As shown in FIG. 46, in one embodiment, the frame 712 includes a frame recess 726 defining an area of reduced thickness for the frame 712. The frame recess 726 is configured to receive the center assembly 718. In one embodiment, a central boss 728 extends up from a portion of the frame 712 in the area of the frame recess 726, and may include a boss aperture 730 configured to receive a threaded member of the center assembly 718 to secure the center assembly 718 relative to the frame 712. Mounting members 732, 734 extend from the frame 712 and enable securement of retractor 710 via one or more table mount assemblies, etc. The mounting members 732, 734 may be at least partially received in correspondingly shaped recesses in the first and second side assemblies 714, 716 when the retractor 710 is in a closed position as shown in FIG. 35.

According to one embodiment, the first side assembly 714 includes a first arm portion 736 and a second arm portion 738. The first arm portion 736 translates along the frame 712, and the second arm portion 738 rotates, or pivots, relative to the first arm portion 736 to provide angulation for a first side blade assembly 740. The first arm portion 736 includes a first side cavity 742 that receives the frame 712, and a first side adjustment knob 744 that engages the frame teeth 724 to move the first arm portion 736, and therefore the first side assembly 714, along the frame 712. The first side adjustment knob 744 is rotatable in opposite directions and engages the frame teeth 724 to provide more or less retraction at a desired site. A first side ratchet mechanism 746 (see FIG. 34) is biased into engagement with the frame teeth 724 to prevent inward movement of the first arm portion 736, and therefore the first side assembly 714, relative to the frame 712 when a user releases the first side adjustment knob 744. The first side ratchet mechanism 746 includes a depressible tab portion that enables a user to release the first side ratchet mechanism 746 and permit free movement of the first side assembly 714 along the frame 712.

Figure 33:
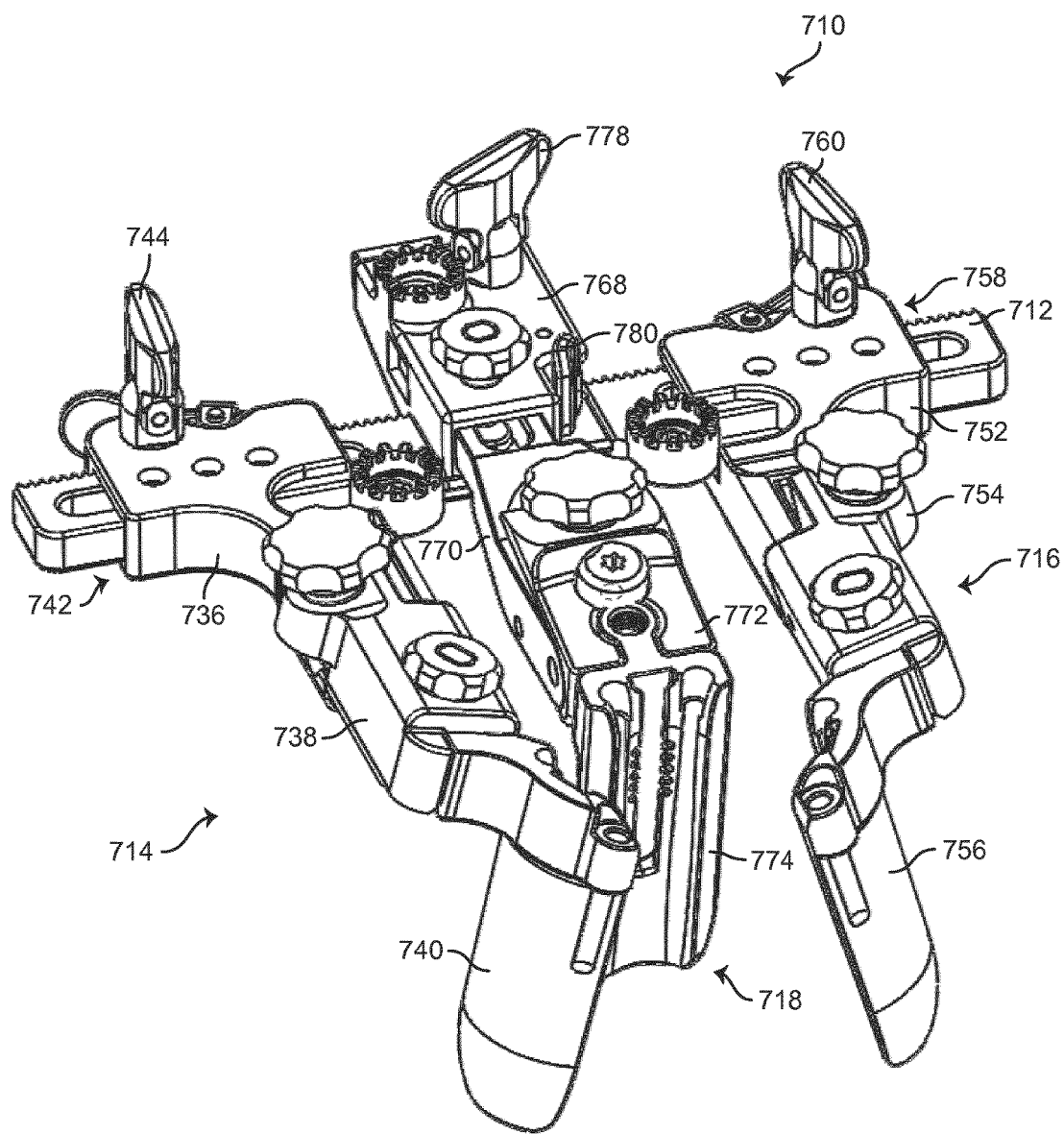
FIG. 33 is a perspective view of a spinal retractor according to another embodiment.
Figure 49:
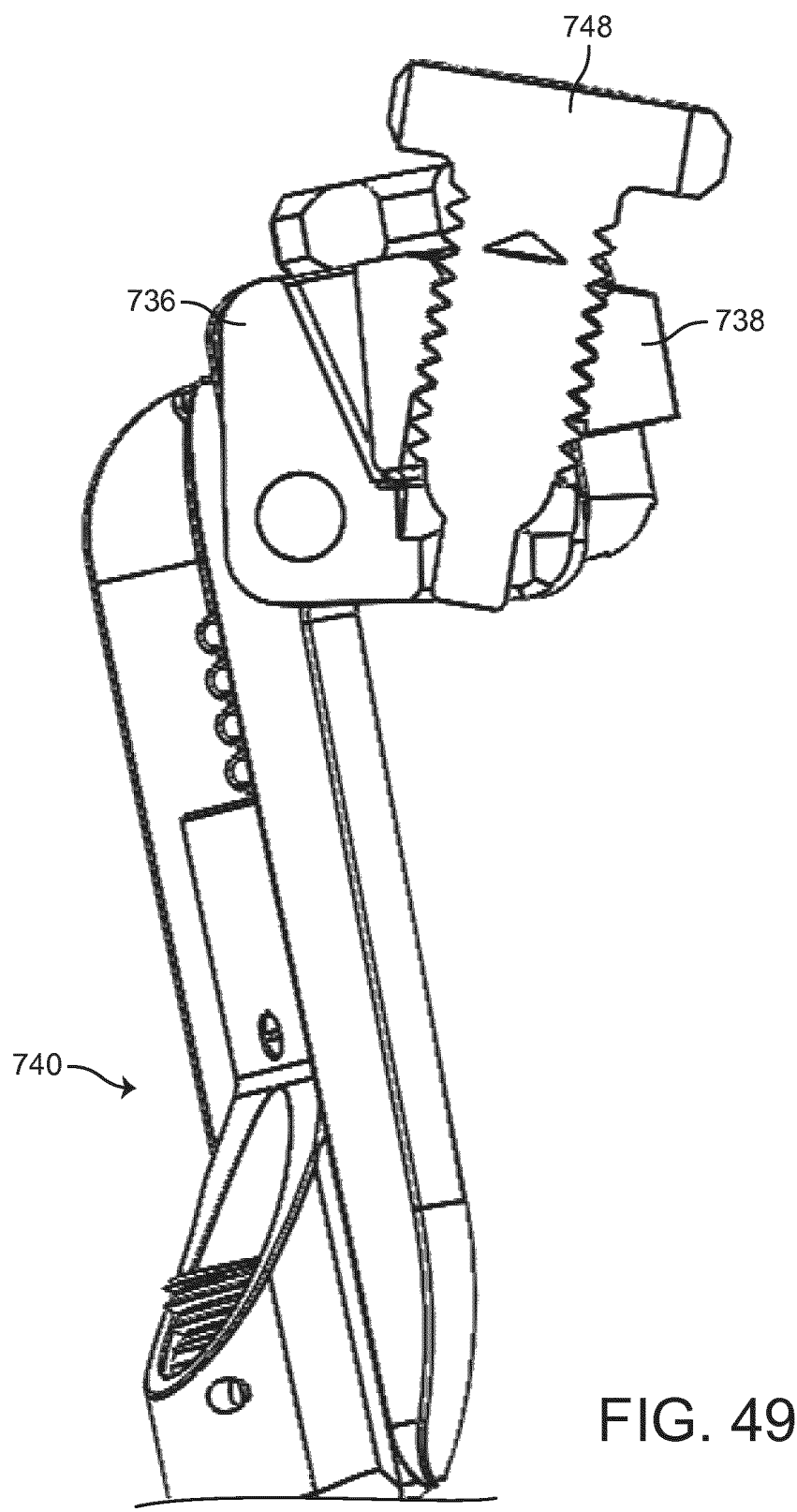

In some embodiments, a first side angulation knob 748 enables pivotal adjustment of the second arm portion 738 relative to the first arm portion 736 between a normal position (see FIG. 37) and an angulated position (see FIG. 33). As also shown in FIG. 49, rotation of the first side angulation knob 748 cause the second arm portion 738 to pivot relative to the first arm portion 736, providing a desired degree of angulation to a particular retraction site.

Figure 35:
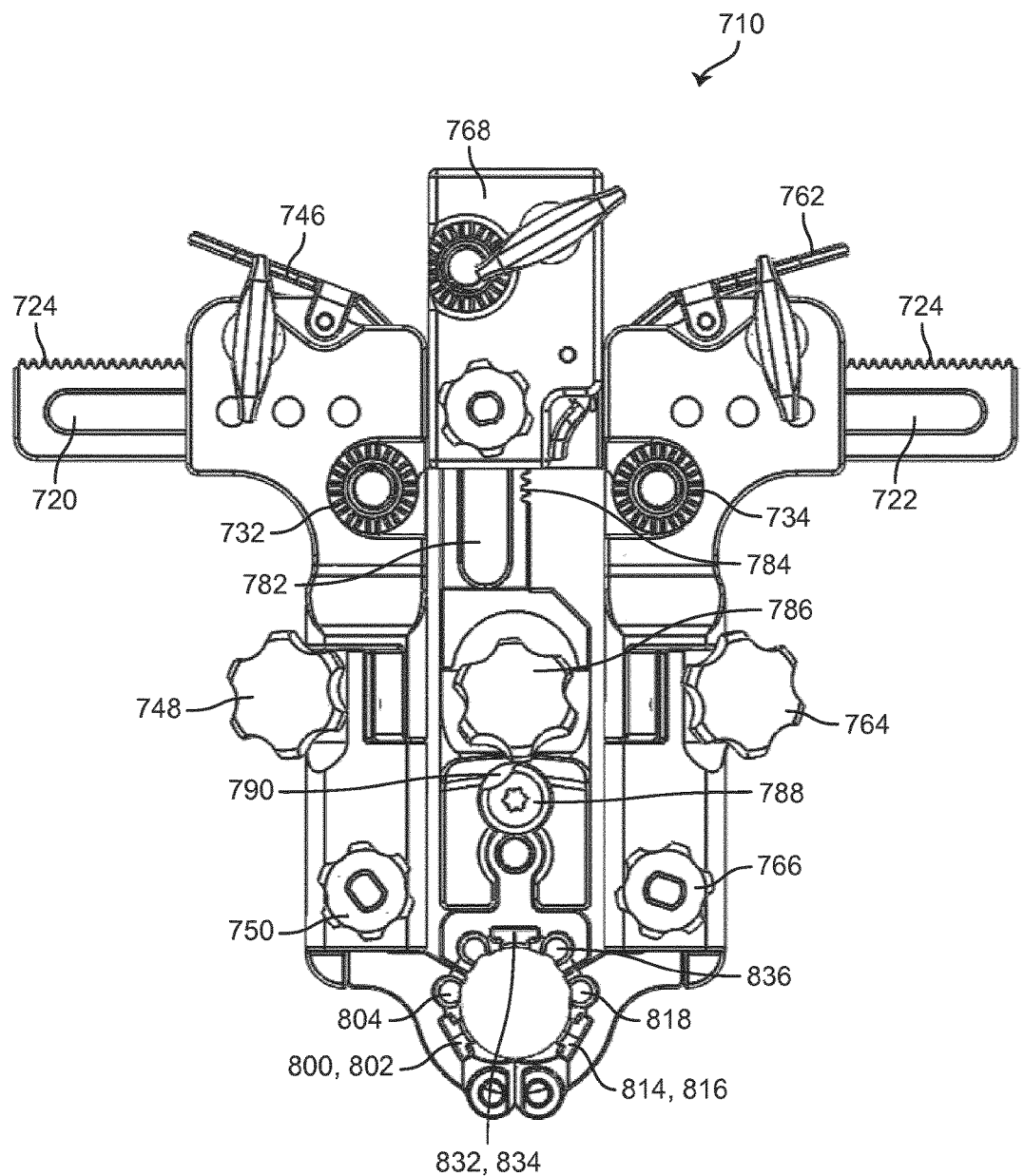
FIG. 35 is a top view of the spinal retractor of FIG. 33 according to one embodiment.

The first side blade assembly 740 is secured to the second arm portion 738 by way of a first side locking knob 750 (see FIG. 35). As shown in greater detail n FIG. 48, the first side locking knob 750 extends through the second arm portion 738 and threadingly engages the first side blade assembly 740. In one embodiment, the first side blade assembly 740 is received by the second arm portion 738 from a bottom direction. In other embodiments, the first side blade assembly 740 may be received from a top direction. Other configurations are possible according to various alternative embodiments.

According to one embodiment, the second side assembly 716 includes a first arm portion 752 and a second arm portion 754. The first arm portion 752 translates along the frame 712, and the second arm portion 754 rotates, or pivots, relative to the first arm portion 752 to provide angulation for a second side blade assembly 756. The first arm portion 752 includes a second side cavity 758 that receives the frame 712, and a second side adjustment knob 760 that engages the frame teeth 724 to move the first arm portion 752, and therefore the second side assembly 716, along the frame 712. The second side adjustment knob 260 is rotatable in opposite directions and engages the frame teeth 724 to provide more or less retraction at a desired site. A second side ratchet mechanism 762 (see FIG. 34) is biased into engagement with the frame teeth 724 to prevent inward movement of the first arm portion 752, and therefore the second side assembly 716, relative to the frame 712 when a user releases the second side adjustment knob 760. The second side ratchet mechanism 762 includes a depressible tab portion that enables a user to release the second side ratchet mechanism 762 and permit free movement of the second side arm assembly 716 along the frame 712.

In some embodiments, a second side angulation knob 764 enables pivotal adjustment of the second arm portion 754 relative to the first arm portion 752 between a normal position (see FIG. 37) and an angulated position (see FIG. 33). As also shown in FIG. 49 with respect to the first side assembly 714, rotation of the second side angulation knob 764 causes the second arm portion 754 to pivot relative to the first arm portion 752, providing a desired degree of angulation to a particular retraction site.

The second side blade assembly 756 is secured to the second arm portion 754 by way of a second side locking knob 766. As shown in greater detail n FIG. 48 with respect to the first side assembly 714, the second side locking knob 766 extends through the second arm portion 754 and threadingly engages the second side blade assembly 756. In one embodiment, the second side blade assembly 756 is received by the second arm portion 754 from a bottom direction. In other embodiments, the second side blade assembly 756 may be received from a top direction. Other configurations are possible according to various alternative embodiments.

The center assembly 718 includes a center housing 768, a first arm portion 770, a second arm portion 772, and a center blade assembly 774. The first arm portion 770 includes a center slot 782 and translates relative to the center housing 768. The second arm portion 772 is pivotally coupled to the first arm portion 770. The center blade assembly 774 is removably secured to the second arm portion 772.

Figure 34:
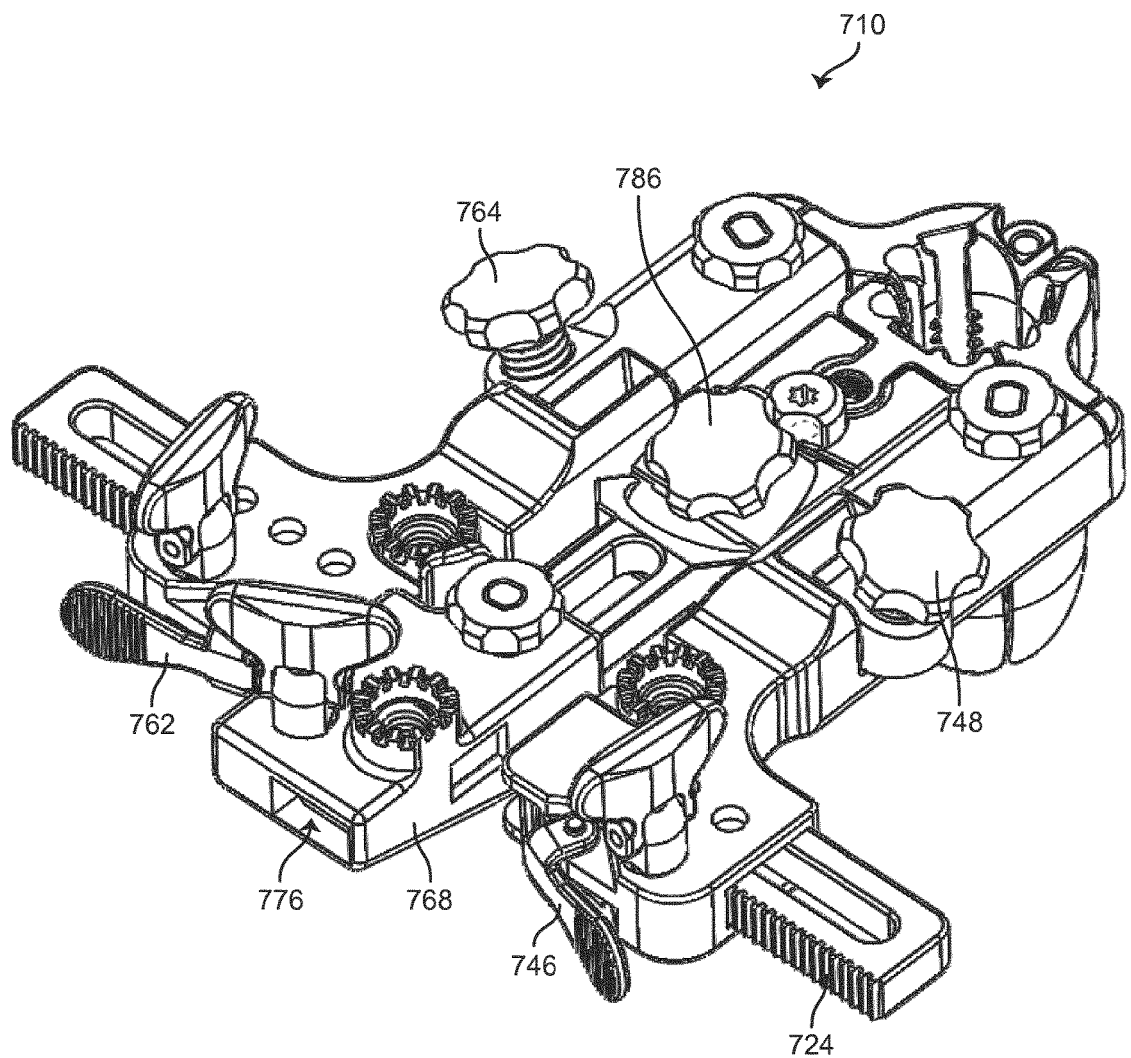
FIG. 34 is another perspective view of the spinal retractor of FIG. 33 according to one embodiment.

Referring further to FIGS. 33-35, the center housing 768 includes a housing cavity 776 that receives the first arm portion 770 and enables translational movement of the first arm portion 770 relative to the center housing 768. A center adjustment knob 778 extends through the center housing 768 and into the housing cavity 776 to engage center teeth 784 provided on the first arm portion 770, such that rotation of the center adjustment knob 778 causes the first arm portion 770 to move into and out of the housing cavity 776. A center ratchet mechanism 780 is biased into engagement with the center teeth 784 to prevent inward movement of the first arm portion 770, and therefore the center assembly 718, relative to the center housing 768 and frame 712 when a user releases the center adjustment knob 778. The center ratchet mechanism 780 includes a depressible tab portion that enables a user to release the center ratchet mechanism 780 and permit free movement of the first arm portion 770 within the housing cavity 776.

In some embodiments, a center angulation knob 786 enables pivotal adjustment of the second arm portion 772 relative to the first arm portion 770 between a normal position (see FIG. 37) and an angulated position (see FIG. 33). Rotation of the center angulation knob 786 causes the second arm portion 772 to pivot relative to the first arm portion 770, providing a desired degree of angulation to a particular retraction site.

The center blade assembly 774 is secured to the second arm portion 772 by way of a center locking screw 788. The center locking screw 788 extends into the second arm portion 772 and locks the center blade assembly 774 into position. In one embodiment, the center blade assembly 774 is received by the second arm portion 772 from a top direction. As shown in FIG. 35, the center locking screw 788 includes a head having a cutout 790 that enables a user to insert and remove the center blade assembly 774 from a top direction relative to the second arm portion 772. When the center blade assembly 774 is in an inserted position, the center locking screw 788 is rotated to move the cutout 790 in the head of the center locking screw 788 such that the center locking screw 788 maintains the center blade assembly 774 in position. Other configurations are possible according to various alternative embodiments.

Figure 36:
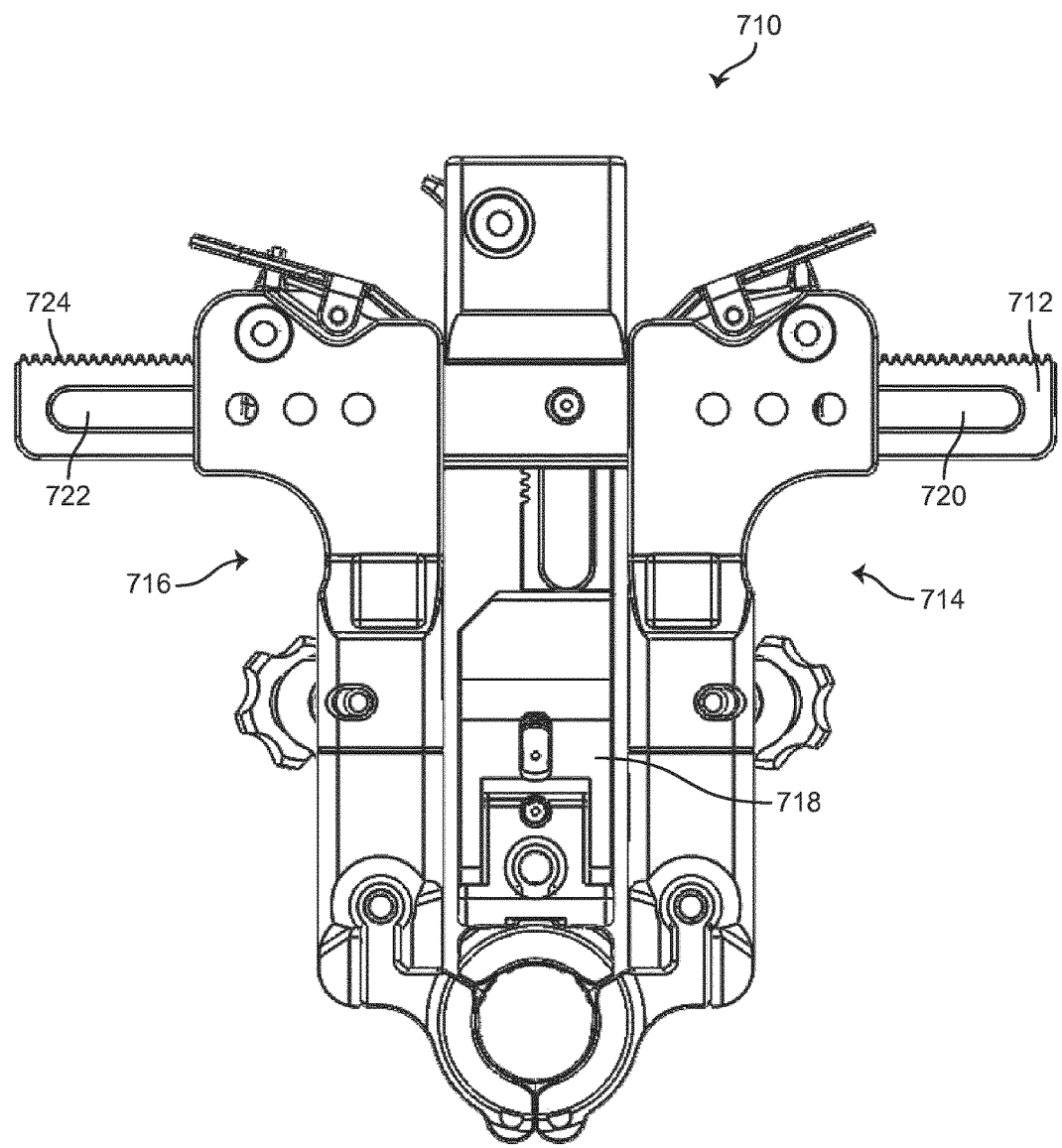
FIG. 36 is a bottom view of the spinal retractor of FIG. 33 according to one embodiment.
Figure 37:
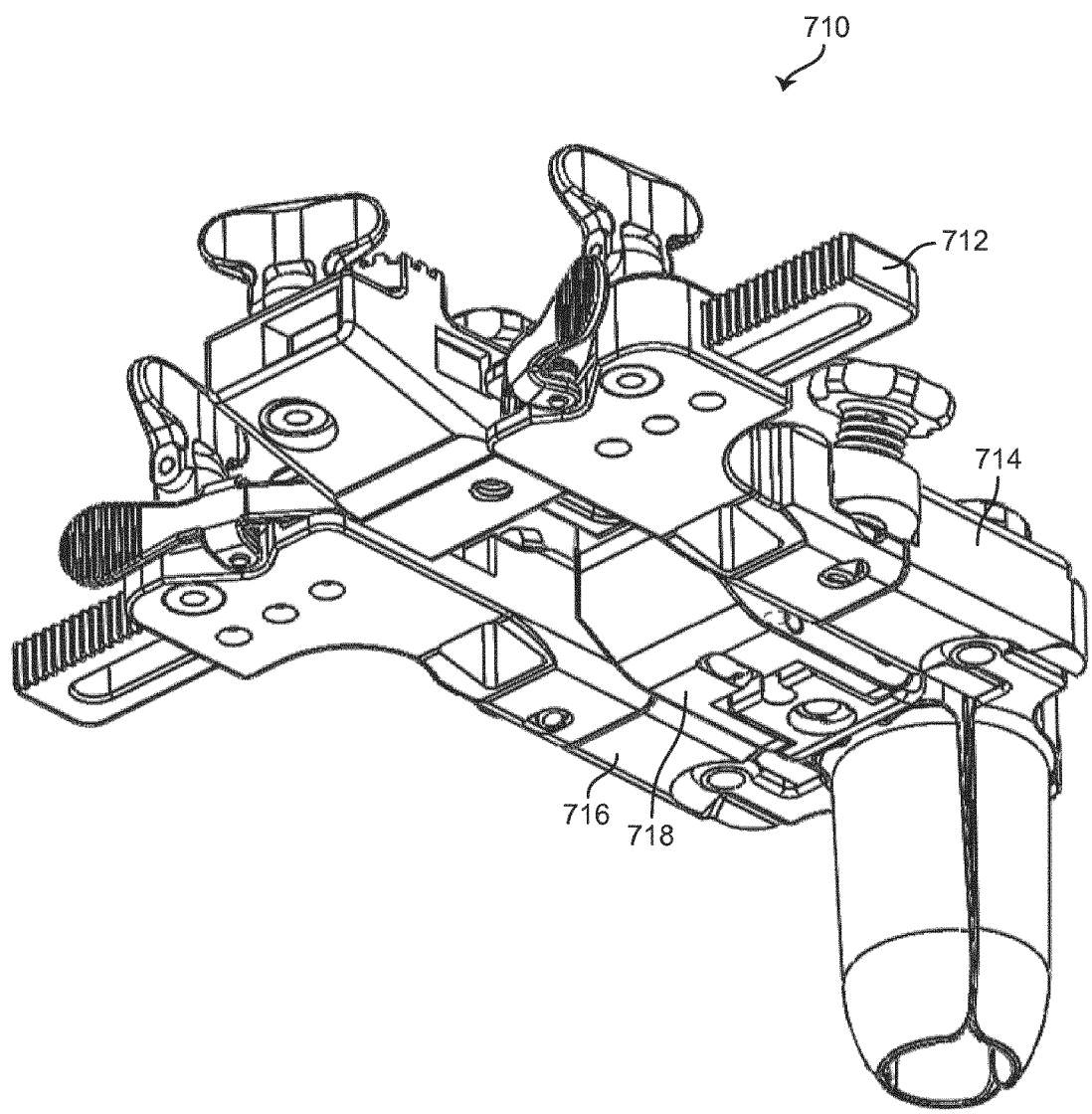
FIG. 37 is another perspective view of the spinal retractor of FIG. 33 according to one embodiment.
Figure 38:
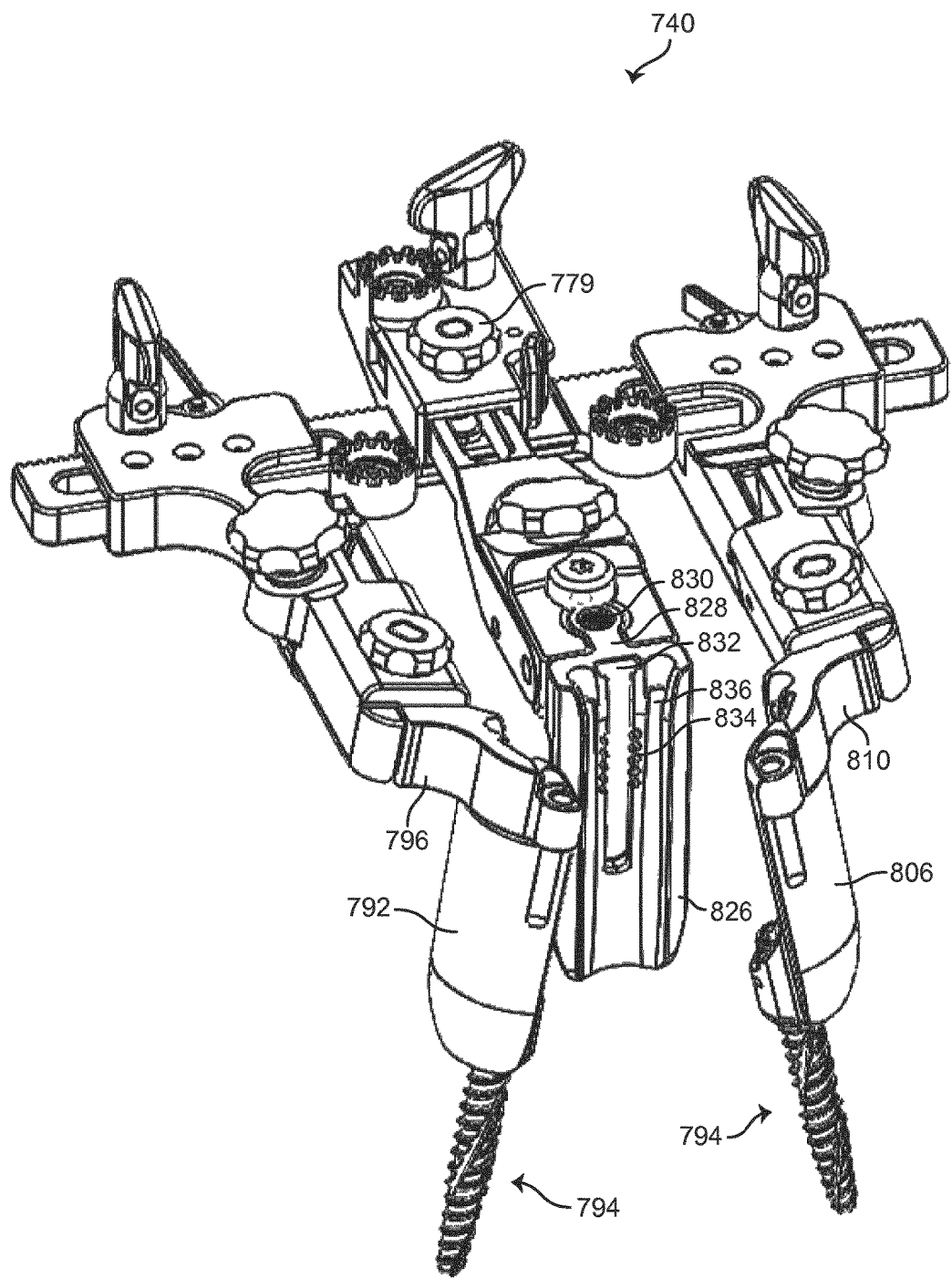
FIG. 38 is a perspective view of the spinal retractor of FIG. 33 including modular tap assemblies according to one embodiment.
Figure 39:
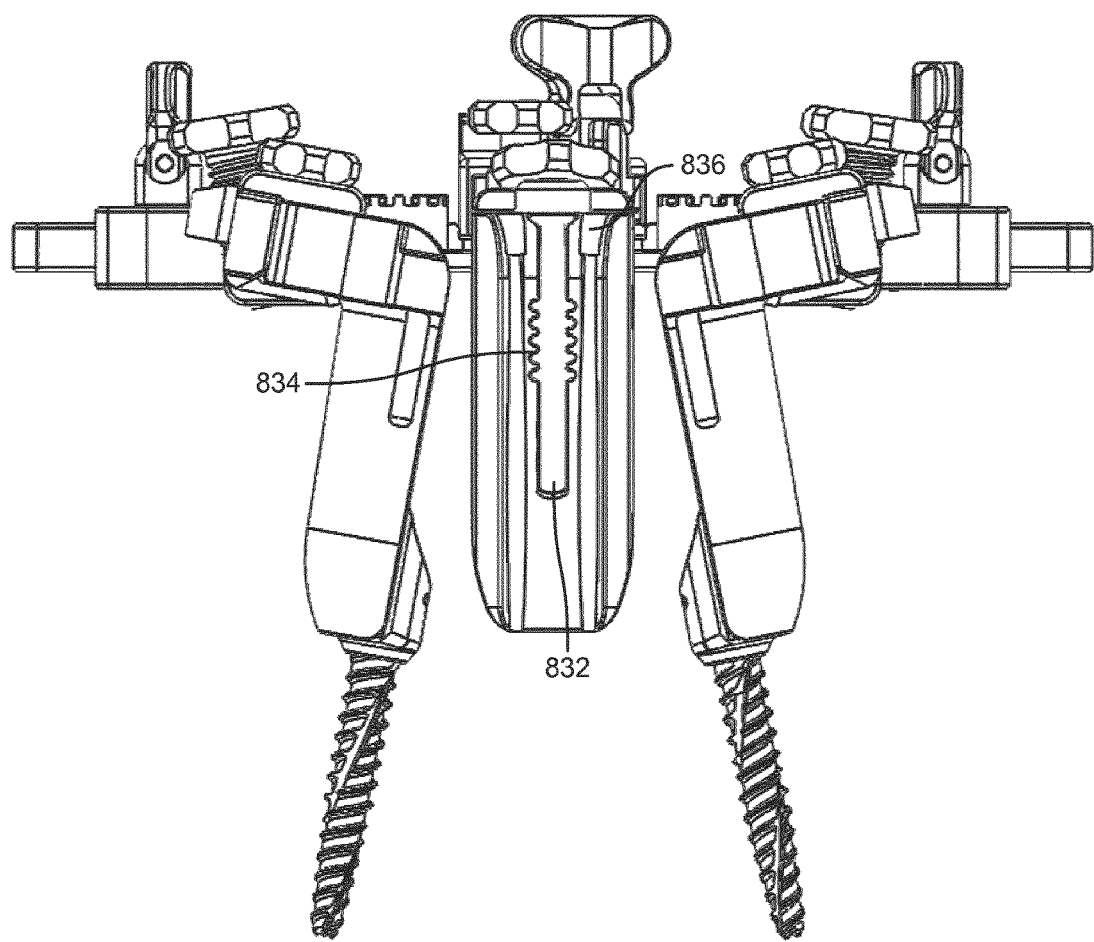
FIG. 39 is a front view of the spinal retractor of FIG. 38 according to one embodiment.
Figure 40:
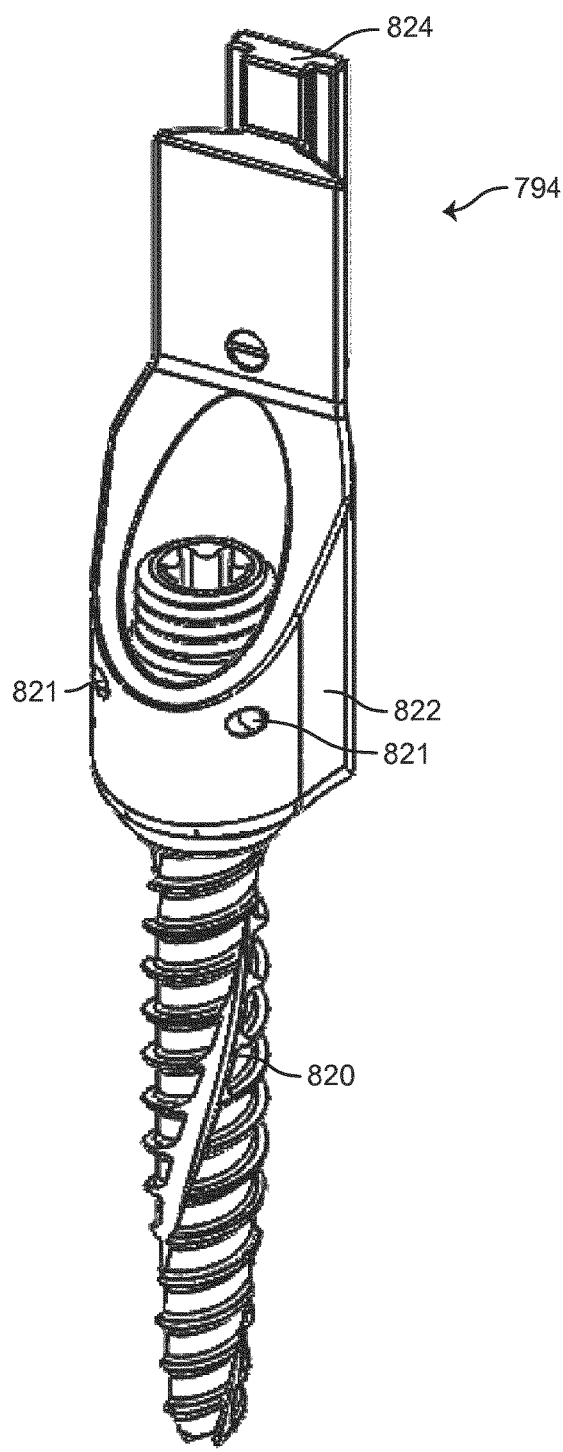
Figure 41:
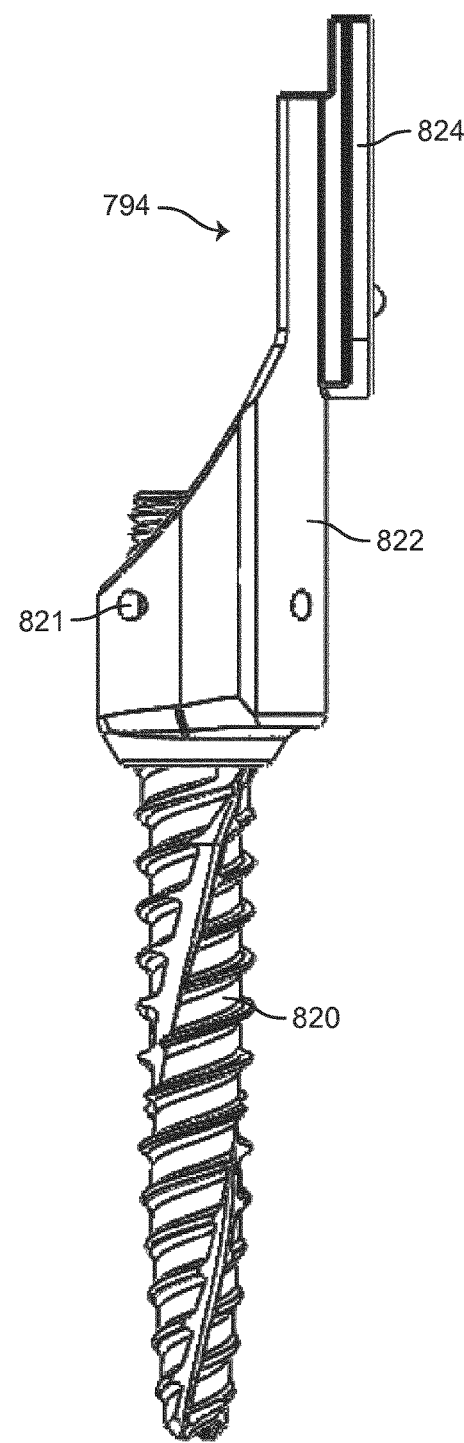

The spinal retractor 710 is movable between an open configuration, shown in FIG. 33, to a closed configuration, shown in FIGS. 34-36, through translation of the first side assembly 714 and the second side assembly 716 and/or the center assembly 718 relative to the frame 712. Furthermore, the first side assembly 714, the second side assembly 716, and the center assembly 718 receive the first side, second side, and center blade assemblies 740, 756, 774, which are configured to hold tissue apart during various procedures. The blade assemblies 740, 756, 774 may be angulated (e.g., moved from a generally vertical, parallel orientation to one or more non-vertical, or angled, orientations) to suit a particular procedure.

Referring now to FIGS. 38-45, in one embodiment, the first side blade assembly 740 includes a first side blade 792, a modular tap assembly 794, and a first side attachment arm 796. The first side attachment arm 796 includes a first side locking aperture 798 that receives the first side locking knob 750. The first side blade 792 extends downward from the first side attachment arm 796, and the modular tap assembly 794 is removably received by the first side blade 792. The second side blade assembly 756 includes a second side blade 806, a modular tap assembly 794, and a second side attachment arm 810. The second side attachment arm 810 includes a second side locking aperture 812 that receives the second side locking knob 766. The second side blade 806 extends downward from the second side attachment arm 810, and the modular tap assembly 794 is removably received by the second side blade 806. The center blade assembly 774 includes a center blade 826 and a center attachment arm 828. The center blade 826 extends downward from the center attachment arm 828. A center aperture 830 receives the center locking knob to secure the center blade assembly in place.

Figure 44:
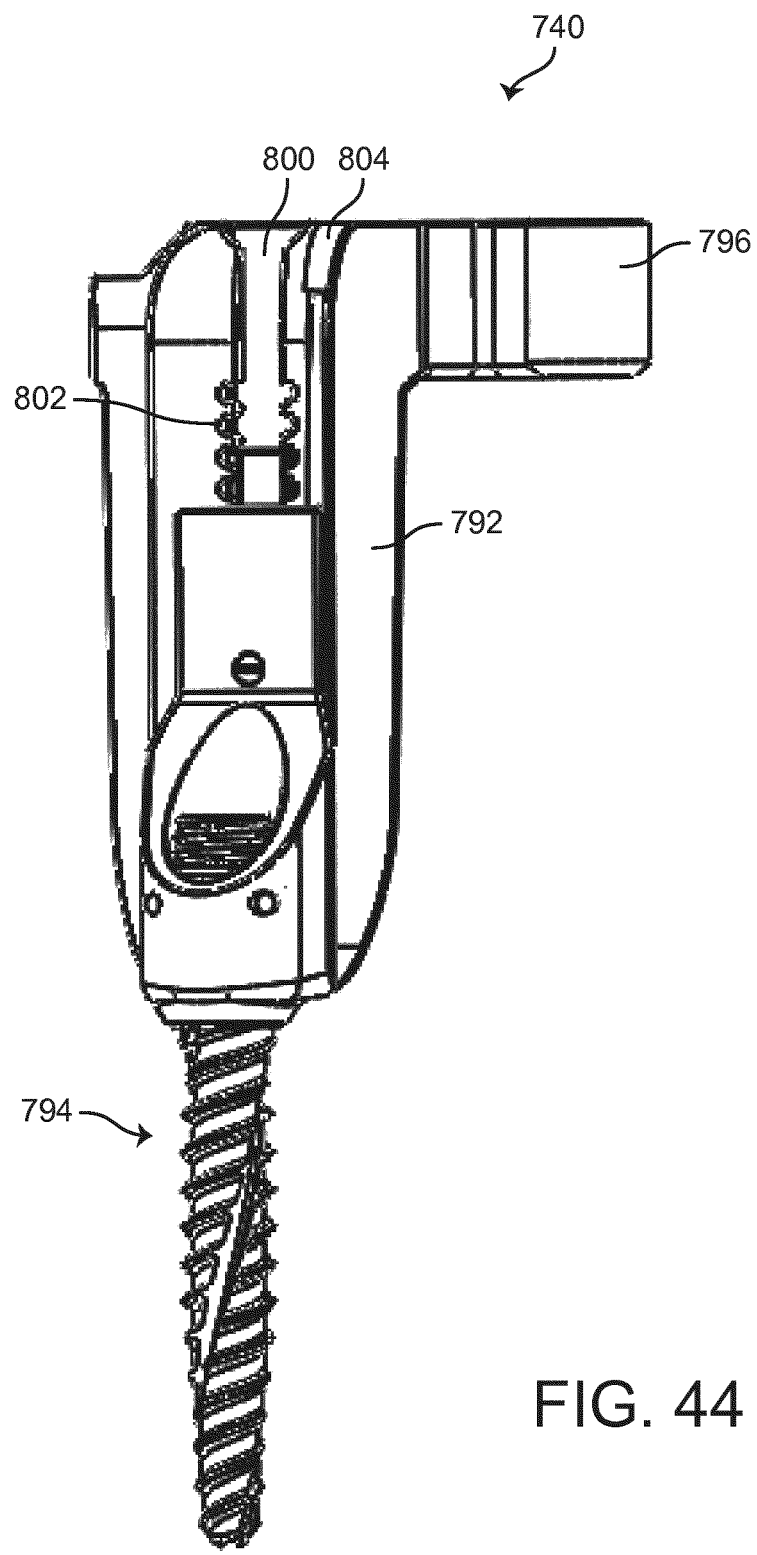
FIG. 44 is a side view of a blade assembly according to one embodiment.

Referring to FIGS. 35 and 44, in one embodiment, the first side blade 792 includes a first side channel 800 and a one or more blade channels 804. The first side channel 800 includes a plurality of notches 802 configured to enable selective positioning of the modular tap assembly 794 within the first side channel 800. The second side blade 806 includes a second side channel 814 and a one or more blade channels 818. The second side channel 814 includes a plurality of notches 816 configured to enable selective positioning of the modular tap assembly 794 within the second side channel 814. The blade channels 818 enable placement of additional positioning pins, lighting devices, etc., via the second side blade 806. The center blade 826 includes a center channel 832 and one or more blade channels 836. The center channel 832 includes one or more notches 838 configured to enable selective positioning of secondary blade 848 within center channel 832. Alternatively, center channel 832 may be configured to receive a modular tap assembly such as modular tap assembly 794.

Figure 45:
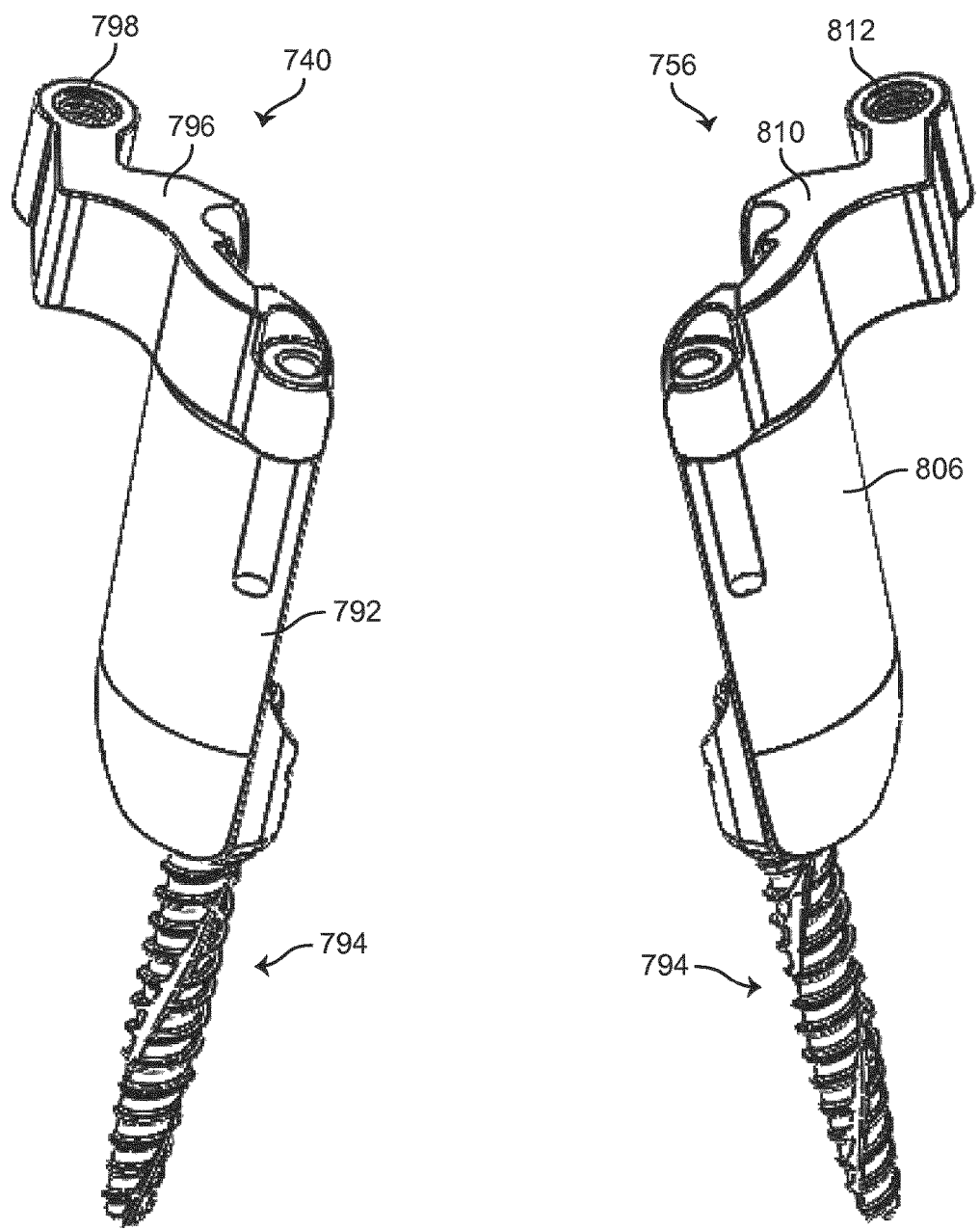
FIG. 45 is a perspective view of first and second blade assemblies according to one embodiment.

Referring to FIGS. 40-43, in one embodiment, the modular tap assembly 794 includes a tap or screw 820, a sleeve 822, and a rail 824. The screw 820 is retained within the sleeve 822, and rotates freely relative to the sleeve 822. In some embodiments, the screw 820 is retained in position by pins 821 that extend through sleeve 822 and are received in a slot or groove in the head of the screw 820, such that the screw 820 is free to rotate but is translationally fixed relative to the sleeve 822. The rail 824 extends along a length of the sleeve 822, and is configured to engage the first side channel 800 and the second slide channel 814 of the first side blade assembly 740 and the second side blade assembly 756, respectively. As shown in FIGS. 44-45, the modular tap assembly 794 may be slid from a bottom direction to couple with the first side blade assembly 740 and the second side blade assembly 756. The rail 824 may include projections or other features configured to engage the notches 802, 816 in the first side channel 800 and the second side channel 814 to enable selective placement of the modular tap assemblies 794 within the first and second side blade assemblies 740, 756.

Figure 47:
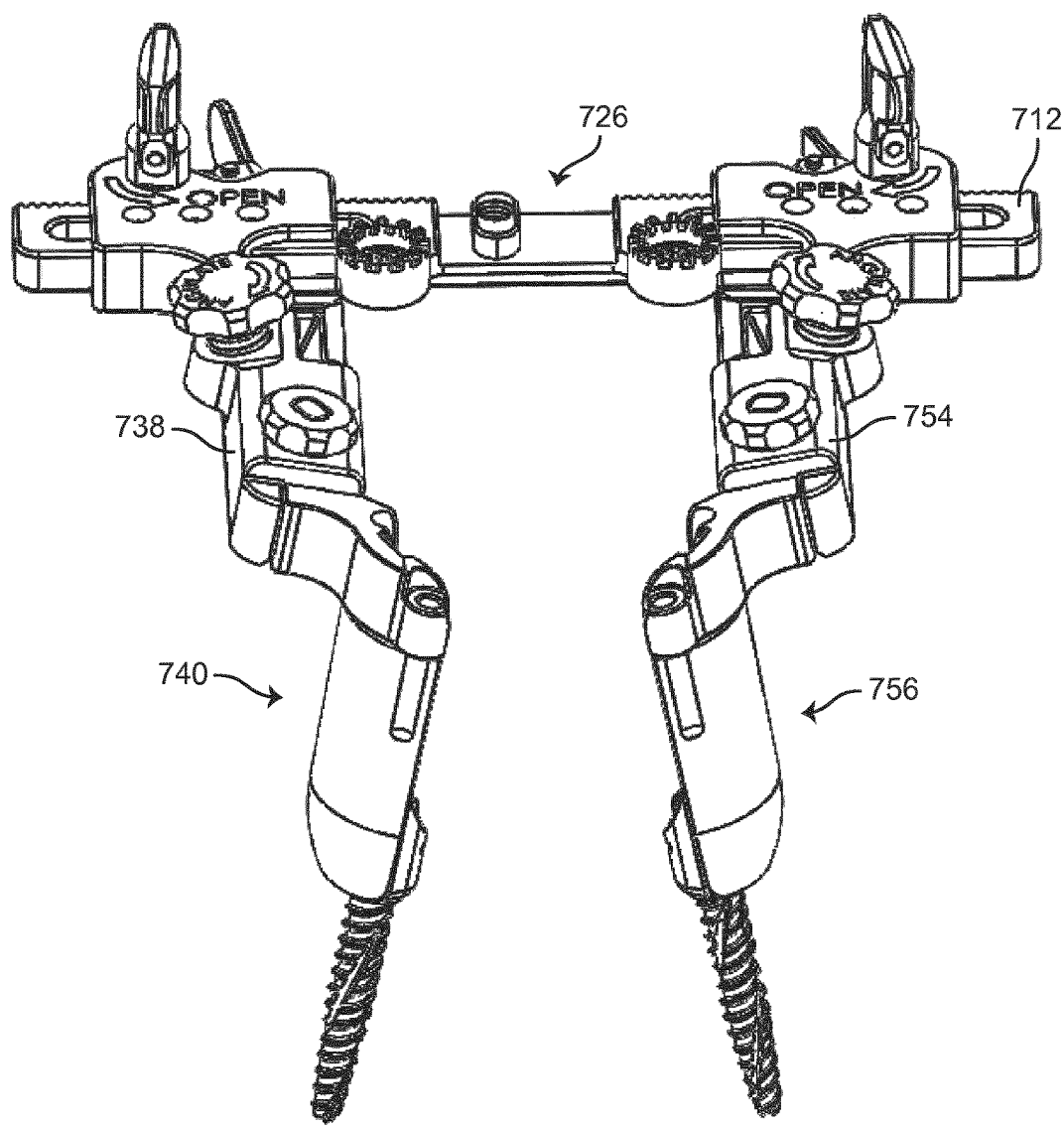
FIG. 47 is a perspective view of a spinal retractor with a center assembly decoupled according to one embodiment.
Figure 48:
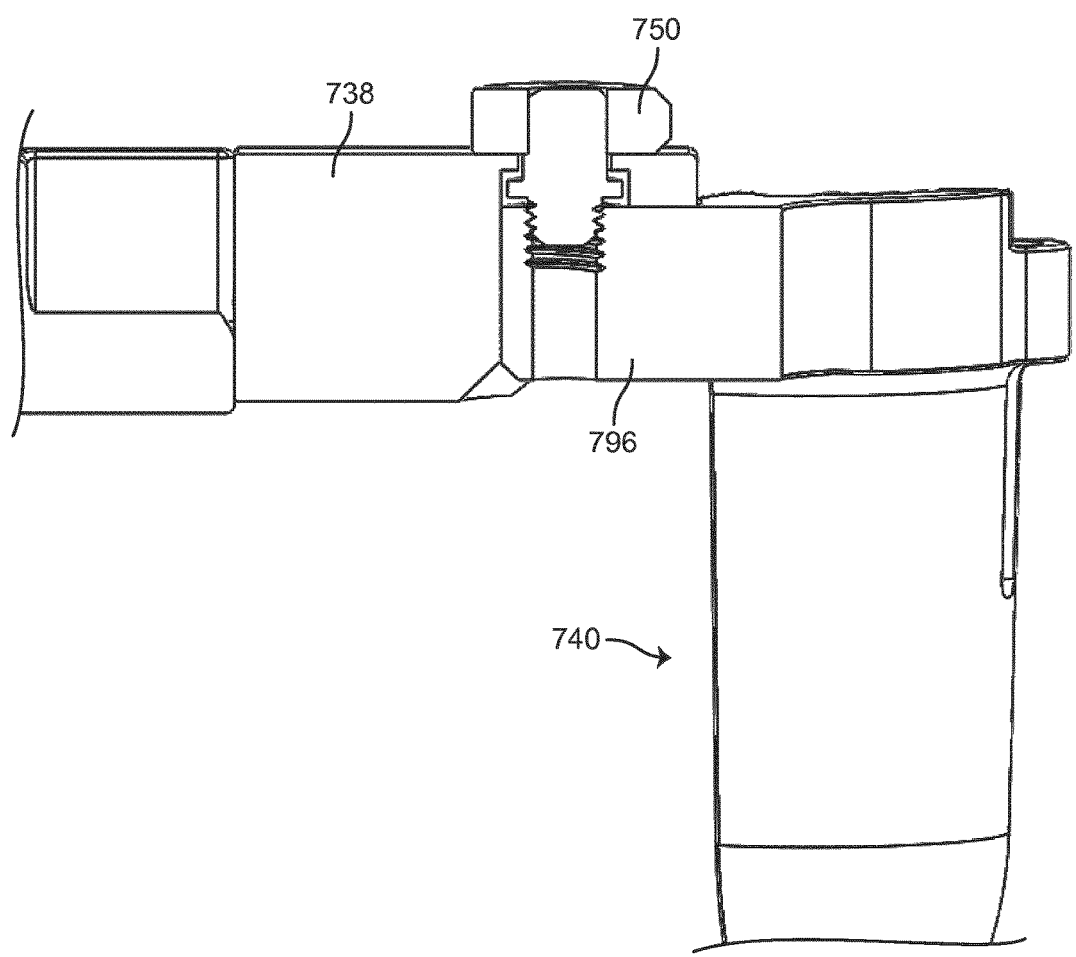
FIGS. 48-49 are partial cross-sectional views of the retractor assembly of FIG. 33 according to one embodiment.

In use, the first and second side blade assemblies 740, 756 are coupled to the modular tap assemblies 794, as shown in FIGS. 44-45. The modular tap assemblies 794 are then secured in desired positions, for example, by threading the screw 820 into one or more desired bone structures. Once the modular tap assemblies 794 are properly positioned, the first and second side blade assemblies 740, 756 are coupled to the second arm portions 738, 754 of the first and second side assemblies 714, 716, as shown in FIGS. 46-47 (e.g., from a bottom direction). Once the first and second side blade assemblies 740,756 are secured in position, the center assembly 718 is secured in position, as shown in FIG. 50 (e.g., from a top direction), by positioning the center housing 768 within the frame recess 726, and threading the center locking knob 779 into the boss aperture 730 of the central boss 728.

Figure 50:
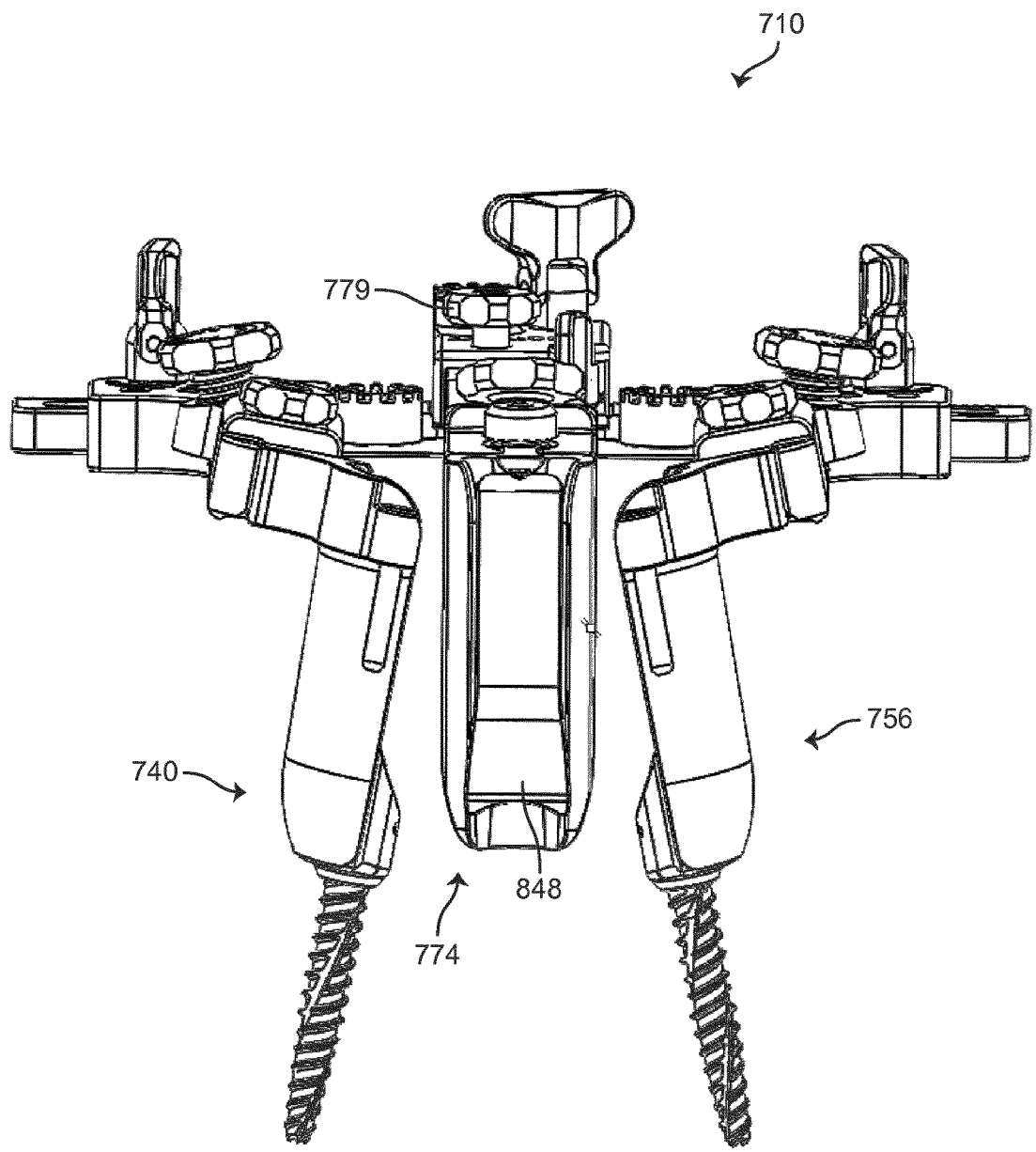
FIGS. 50-51 are views of a spinal retractor with a secondary blade according to one embodiment.
Figure 51:
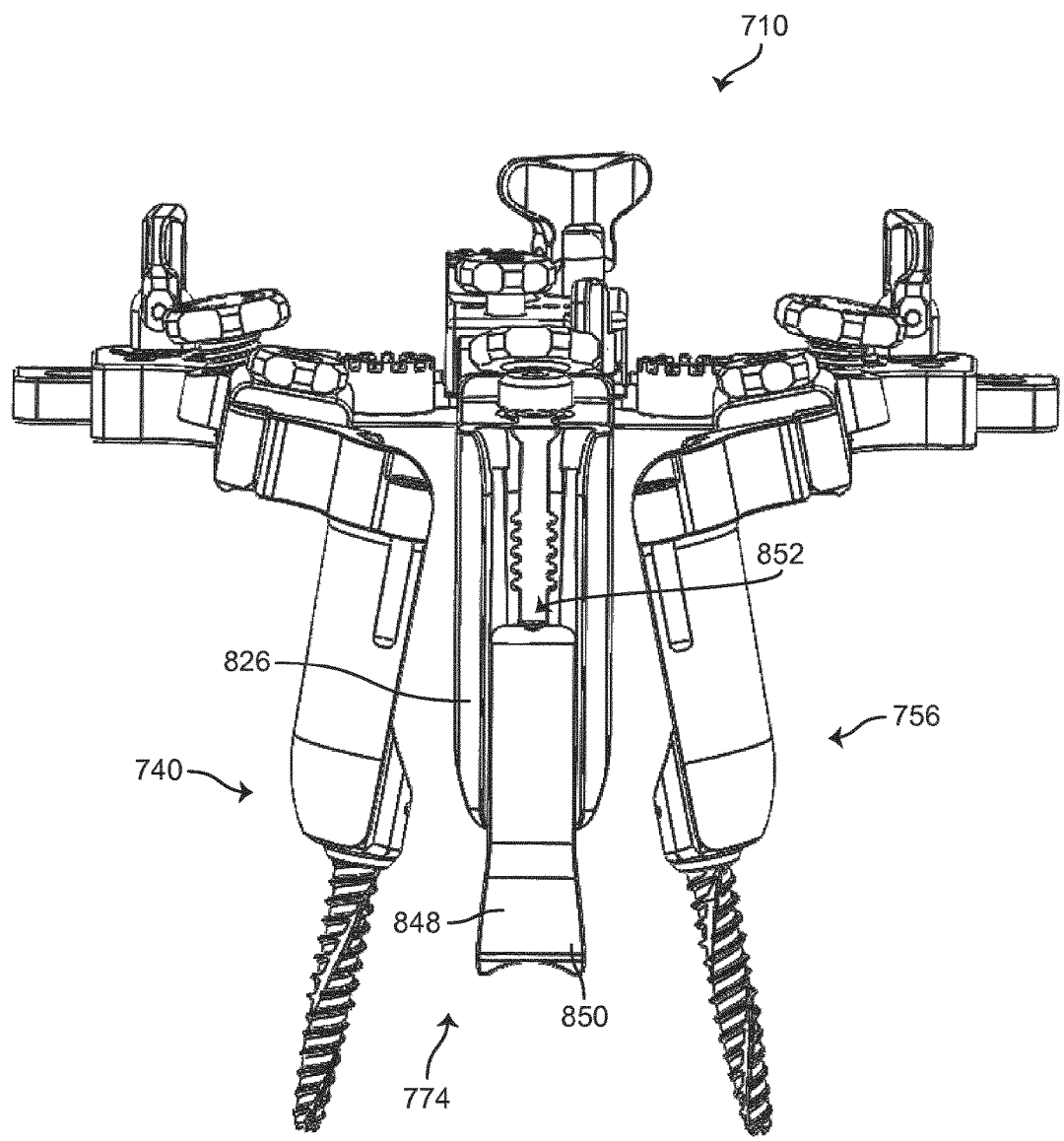

Referring to FIGS. 50-51, if desired, the secondary blade 848 may be slid into the center blade 826 by way of the center channel 832. The secondary blade 848 includes a flared portion 850 and a rail 852 received within the center channel 832. The rail 852 of the secondary blade 848 may include projections or other features to enable selective engagement with the notches 834 of the center channel 832 and positioning of the secondary blade 848.

Figure 52:
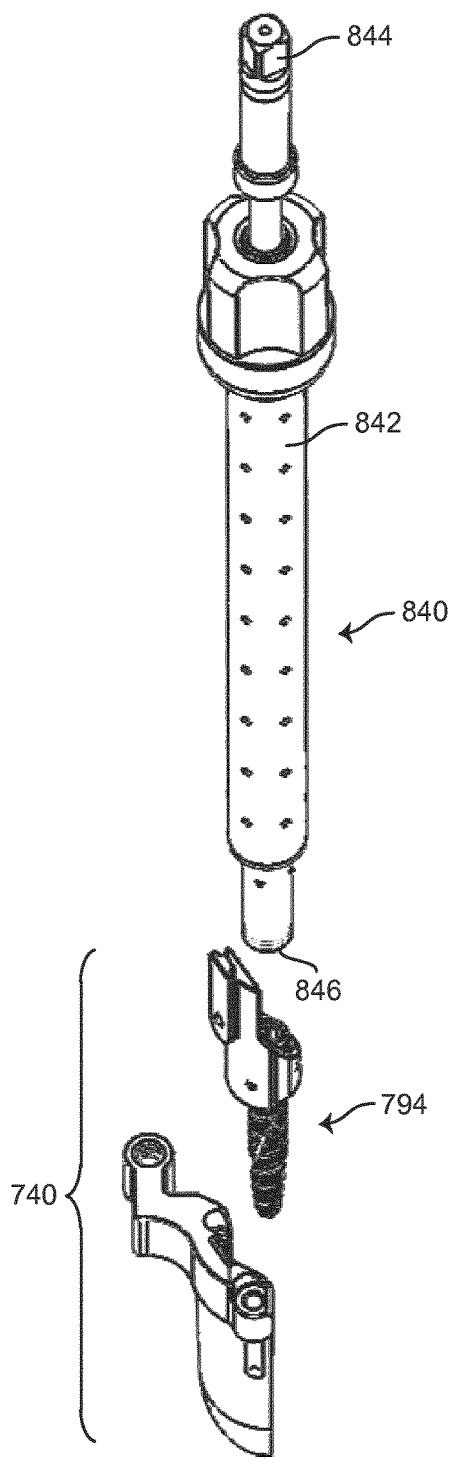
FIGS. 52-54 are views of a driver assembly usable with a spinal retractor according to one embodiment.
Figure 53:
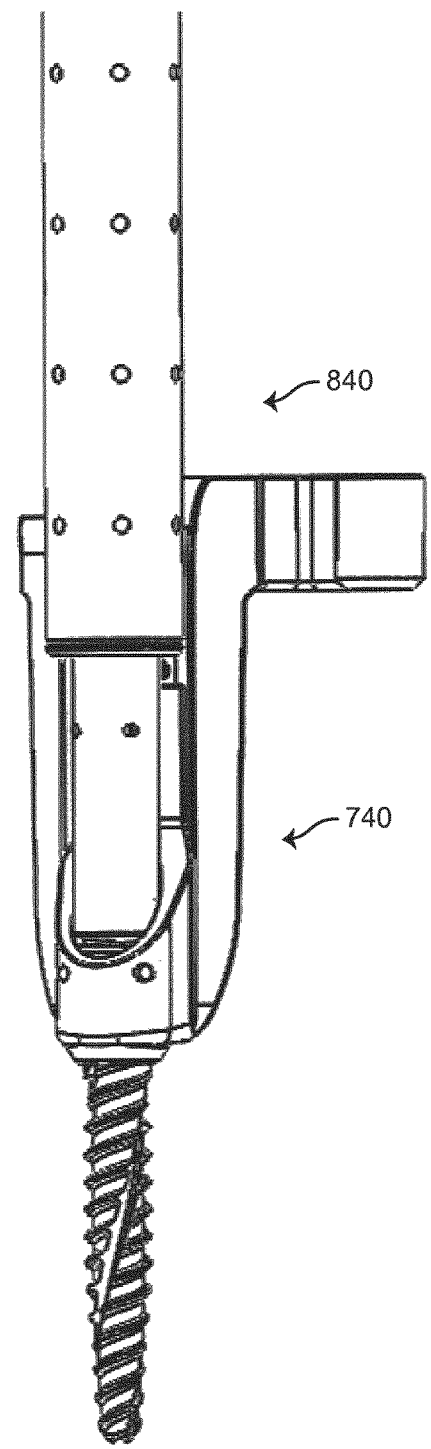
Figure 54:
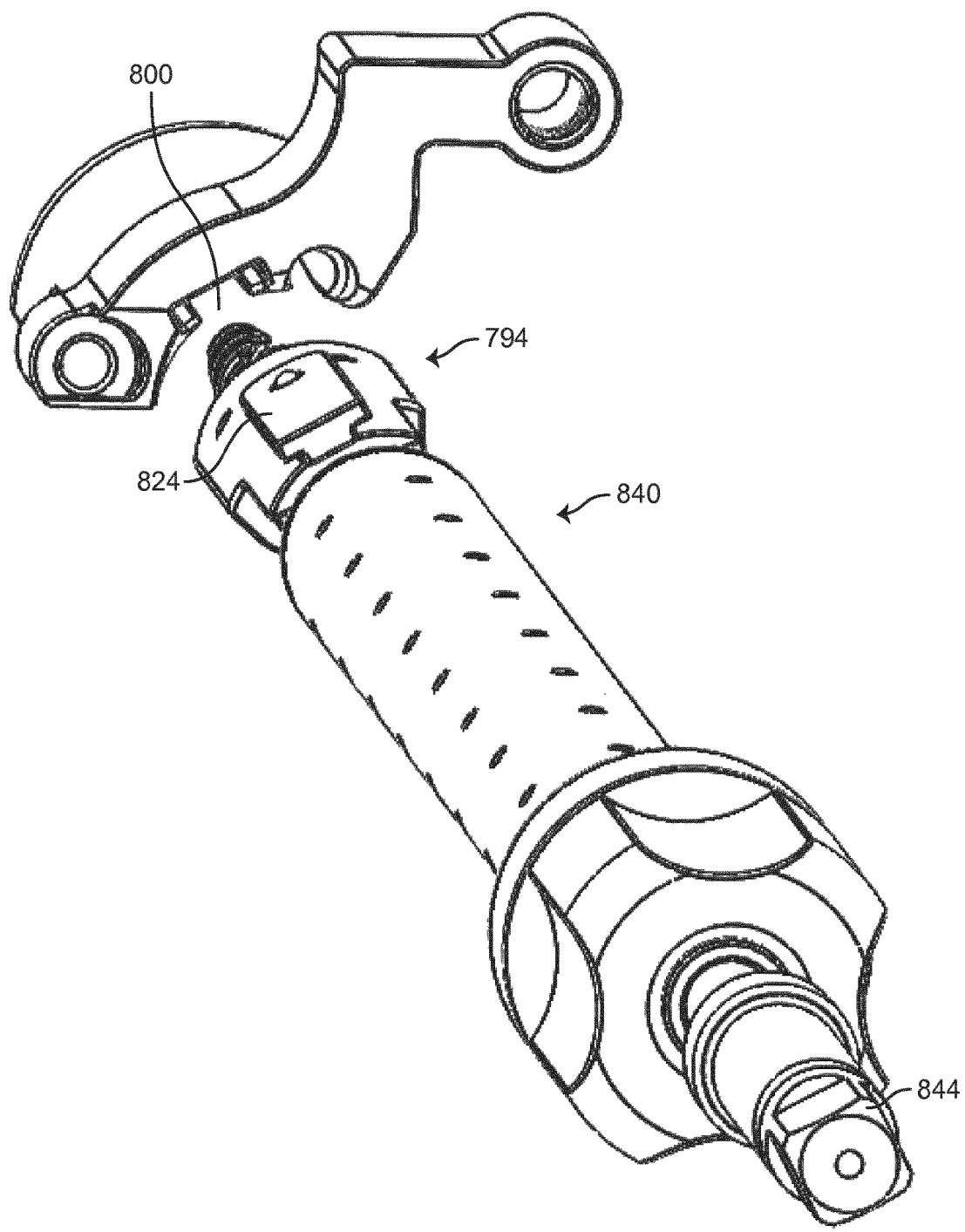

Referring now to FIGS. 52-54, a driver assembly 840 usable to install a blade assembly such as the first side blade assembly 740 is shown according to one embodiment. The driver assembly 840 includes an outer housing 842, a top drive member 844, and a bottom drive member 846. The bottom drive member 846 is configured to mate with the screw 820 of the modular tap assembly 794, and the top drive member 844 is configured to mate with an appropriate tool (e.g., a driver, etc.), such that rotation of the top drive member 844 results in a corresponding rotation of the bottom drive member 846 and the screw 820. In some embodiments, as shown in FIGS. 53-54, the driver assembly 840 is usable when the modular tap assembly 794 is coupled to a blade assembly such as the first side blade assembly 740 or the second side blade assembly 756.

Figures 55, 56:
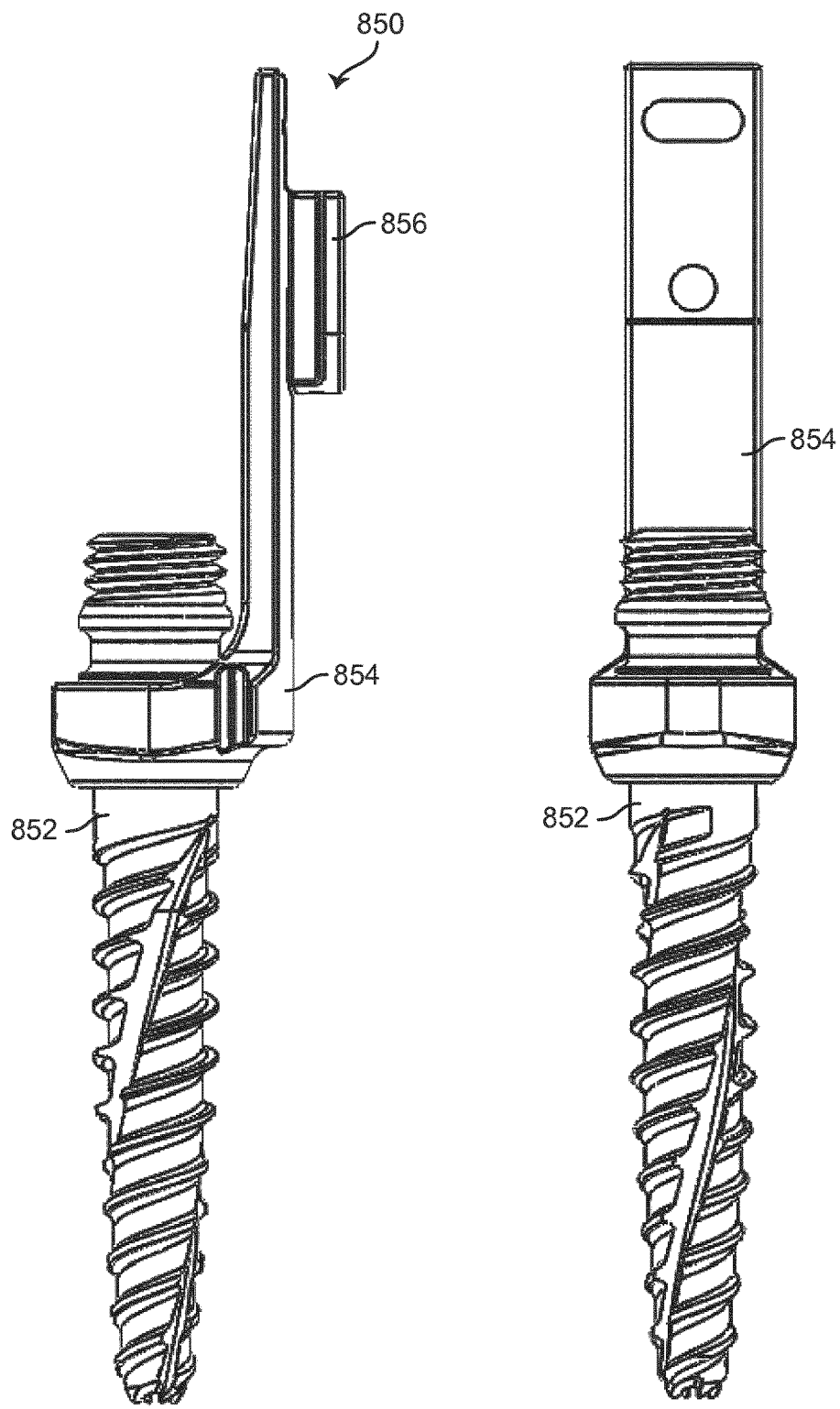
FIGS. 55-57 are views of a modular tap assembly according to an alternative embodiment.
Figure 57:
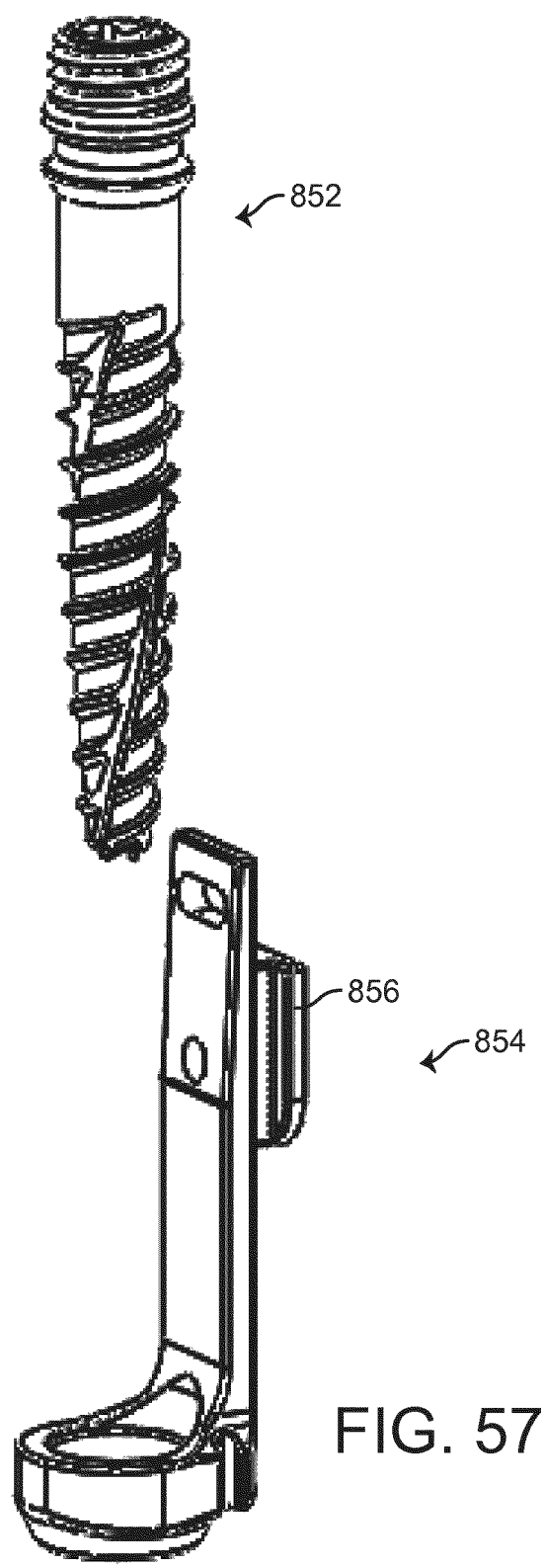

In some embodiments, an alternative modular tap assembly may be used in place of or in combination with the modular tap assembly 794. For example, as shown in FIGS. 55-57, a modular tap assembly 850 includes a tap or screw 852, a sleeve 854, and a rail 856. The modular tap assembly 850 interfaces with the other components described herein in a similar manner as the modular tap assembly 794, and has similar structural features, with the exception that the screw 852 is not translationally fixed relative to the sleeve 854, but rather engages the sleeve 854 as shown in FIG. 57. As such, the screw 842 is slid into sleeve 854 prior to being secured to any bone material.

It should be understood that the spinal retractor shown in FIGS. 33-54 may share any or all of the features described elsewhere herein, including blade extenders/supplemental blades, blade locking features, lighting features extending within channels in the blades, and the like. All such combinations of features are to be understood to be within the scope of the present disclosure.

In one embodiment, in operating a spinal retractor such as one described herein, the retractor is placed into a desired position. A first side assembly, a second side assembly, and a center assembly of the retractor are translated along threaded shafts relative to a frame of the retractor. The side and center assemblies may be translated via manipulation of ball joint assemblies that couple adjustment knobs to the respective threaded shafts.

The spinal retractor shown and described herein may provide various benefits over more traditional designs. The support handle provides a modular, ergonomic handle for improved manipulation of the base or frame to ease alignment of the device, and the adjustment handles provide modular ergonomic handles for translation of the side and center assemblies without the need for additional instrumentation. Further, the adjustment handles stabilize the positions of the adjustment knobs for ease of use. The gear rations of the threaded shafts provide faster translation of components (e.g., twice as fast as certain conventional device) such that each of the side and center assemblies can be completely expanded with 1.5 revolutions of the threaded shafts/adjustment knobs.

Additionally, the frame weight is less compared to more traditional devices (e.g., by 15 percent or more), and the frame geometry is optimized to enable table arm attachment to the center arm assembly while eliminating interference with the base or frame (e.g., in situations when the table arm extends generally parallel to the length of the frame or base). In some embodiments, blade extenders include self-retaining springs to ensure the blade extenders remain captured within the blades, and the blade locking mechanisms provide a spring-activated locking feature requiring only a one quarter turn to lock/unlock the blades. Further, light sources may extend down channels in the blades to provide optimized lighting (e.g., 15 percent or more light output relative to more traditional designs).

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A retractor assembly, comprising;
   an elongated base having a first side including a first plurality of teeth and a first elongated through slot extending along a first direction, and a second side including a second plurality of teeth and a second elongated through slot extending along the first direction;
   a first side arm assembly coupled to the first side of the base and configured to translate along the base in the first direction, the first side arm assembly including:
   a first arm portion including a cavity receiving the first side of the base therethrough, and including a first ratchet mechanism configured to engage the first plurality of teeth;
   a second arm portion coupled to the first arm portion of the first arm assembly and extending along a first longitudinal axis perpendicular to the first direction such that the second arm portion is rotatable about the first longitudinal axis relative to the first arm portion, wherein the second arm portion of the first side arm assembly includes a first recess having a closed superior end closed by a top side of the second arm portion of the first side arm assembly and an inferior open end opening through a bottom side of the second arm portion of the first side arm assembly; and
  a first locking knob extending through the closed superior end of the second arm portion;
a first side blade assembly having a first attachment arm configured to be received in the first recess of the first side arm assembly only from the bottom side of the second arm portion of the first side arm assembly of the retractor assembly such that the first locking knob threadingly engages a locking aperture of the first attachment arm of the first side blade assembly, the first side blade assembly further includes a first tap assembly including a first threaded screw configured to threadingly engage bone;
a second side arm assembly coupled to the second side of the base and configured to translate along the base in the first direction independent from the first side assembly, the second side arm assembly including:
  a first arm portion including a cavity receiving the second side of the base therethrough, and including a second ratchet mechanism configured to engage the second plurality of teeth;
  a second arm portion coupled to the first arm portion of the second side arm assembly and extending along a second longitudinal axis perpendicular to the first direction such that the second arm portion of the second side arm assembly is rotatable about the second longitudinal axis relative to the first arm portion of the second side arm assembly, wherein the second arm portion of the second side arm assembly includes a second recess having a closed superior end closed by a top side of the second arm portion of the second side arm assembly; and an inferior open end opening through a bottom side of the second arm portion of the second side arm assembly; and
  a second locking knob extending through the closed superior end of the second arm portion of the second side arm assembly;
a second side blade assembly having a second attachment arm configured to be received in the second recess of the second side arm assembly only from the bottom side of the second arm portion of the second side arm assembly of the retractor assembly such that the second locking knob threadingly engages a locking aperture of the second attachment arm of the second side blade assembly, the second side blade assembly further includes a second tap assembly including a second threaded screw configured to threadingly engage bone;
a center arm assembly having a first portion removably coupled to a center portion of the base between the first and second sides of the base, and a second portion of the center arm assembly is configured to translate relative to the base and through the first portion of the center arm assembly along a second direction different from the first direction, the second portion of the center arm assembly includes a center recess opening through a top side of the second portion of the center arm assembly;
a center blade assembly having a center attachment arm configured to be removably coupled into the center recess of the second portion of the center arm assembly only from the top side of the second portion of the center arm assembly of the retractor assembly, wherein the center blade assembly includes a second blade received by a first blade coupled to the center arm assembly; and
a locking screw configured to threadingly engage the top side of the second portion of the center arm assembly and having a head including a cutout configured for rotation to be aligned with the center recess to allow coupling the center attachment arm in the center recess of the center arm assembly and configured for rotation to be unaligned with the recess to retain the center attachment arm in the center recess of the center arm assembly.

2. The retractor assembly of claim 1, wherein the first tap assembly includes the first threaded screw rotatably retained within a first sleeve, and wherein the second tap assembly includes the second threaded screw rotatably received within a second sleeve.

3. The retractor assembly of claim 2, wherein the first sleeve includes a first rail configured to be slidably received by the first side blade assembly and the second sleeve includes a second rail configured to be slidably received by the second side blade assembly.

* * * * *